US009694071B2

(12) United States Patent
Weiss et al.

(10) Patent No.: US 9,694,071 B2
(45) Date of Patent: Jul. 4, 2017

(54) COMBINATION OF ANTI-CD20 ANTIBODY AND PI3 KINASE SELECTIVE INHIBITOR

(71) Applicants: TG Therapeutics, Inc., New York, NY (US); Rhizen Pharmaceuticals SA, La Chaux de Fonds (CH); Laboratoire Francais du Fractionnement et des Biotechnologies, Les Ulis (FR)

(72) Inventors: Michael S. Weiss, New York, NY (US); Hari P. Miskin, New York, NY (US); Peter Sportelli, New York, NY (US); Swaroop K. V. S. Vakkalanka, La Chaux de Fonds (CH)

(73) Assignees: TG Therapeutics, Inc., New York, NY (US); Rhizen Pharmaceuticals NA (CH); Laboratoire Francais du Fractionnement et des Biotechnologies (FR)

( * ) Notice: Subject to any disclaimer, the term of this patent is extended or adjusted under 35 U.S.C. 154(b) by 55 days.

(21) Appl. No.: 14/440,139

(22) PCT Filed: Nov. 1, 2013

(86) PCT No.: PCT/US2013/067956
§ 371 (c)(1),
(2) Date: May 1, 2015

(87) PCT Pub. No.: WO2014/071125
PCT Pub. Date: May 8, 2014

(65) Prior Publication Data
US 2015/0290317 A1    Oct. 15, 2015

Related U.S. Application Data

(60) Provisional application No. 61/771,812, filed on Mar. 2, 2013.

(30) Foreign Application Priority Data

Nov. 2, 2012  (IN) .......................... 4595/CHE/2012

(51) Int. Cl.
| A61K 39/395 | (2006.01) |
| A61K 31/519 | (2006.01) |
| C07K 16/28 | (2006.01) |
| A61K 45/06 | (2006.01) |

(52) U.S. Cl.
CPC ........ A61K 39/3955 (2013.01); A61K 31/519 (2013.01); A61K 45/06 (2013.01); C07K 16/2887 (2013.01); C07K 2317/24 (2013.01); C07K 2317/73 (2013.01)

(58) Field of Classification Search
None
See application file for complete search history.

(56) References Cited

U.S. PATENT DOCUMENTS 9,150,579 B2 * 10/2015 Vakkalanka ......... A61K 31/519
2009/0053233 A1 *  2/2009 De Romeuf ....... C07K 16/2896
424/141.1

FOREIGN PATENT DOCUMENTS

| EP | 2000541 | 12/2008 |
| WO | WO2010/014595 | 2/2010 |
| WO | WO2014/006572 | 1/2014 |

OTHER PUBLICATIONS

Smith et al (Toxicological Sciences, 2009, vol. 110, pp. 4-30).*
Birg et al, Blood, 1992, vol. 80, pp. 2584-2593.*
The abstract of Li et al (Zhonghua Xue, 2015, vol. 36, pp. 44-48.*
Dearden, Hematology, 2012, pp. 645-651.*
Abstract of Flinn et al (Journal of Clinical Oncology, 2011, vol. 29, No. 15, May 20 supplement, abstract No. 3064).*
Anonymous, from "reportonbusiness.com: globeinvestor.com" TG Therapeutics, Inc. Announces Poster Presentation for Ublituximab (TGTX-1101) at the 7th Internationall Workshop on Waldenstrom's Macroglobulinemia, Aug. 24, 2012.
Engelman et al. (2006) Nat. Rev. Genet. 7:606-619. The evolution of phosphatidylinositol 3-kinases as regulators of growth and metabolism.
Ihle et al. (2008) Mol. Cancer Ther. 8:1-9. Take your PIK: phosphatidylinositol 3-kinase inhibitors race through the clinic and toward cancer therapy.
Liu et al. (2009) Nature Rev. 8:627-633. Targeting the phosphoinositide 3-kinase pathway in cancer.
Marone et al. (2008) Biochim. Biophys. Acta 1784:159-185. Targeting phosphoinositide 3-kinase—Moving towards therapy.
Phillips et al. (1998) Cancer 83:41-47. Increased Levels of Phosphatidylinositol 3-Kinase Activity in Colorectal Tumors.
Vanhaesebroeck et al. (2005) Trends Biochem. Sci. 30:194-204. Signalling by PI3K isoforms: insights from gene-targeted mice.
Vivanco et al. (2002) Nature Rev. 2:489-501. The Phosphatidylinositol 3-Kinase—AKT Pathway in Human Cancer.
Winiarska et al. (2011) Frontiers Biosci. 16:277-306. Molecular mechanisms of the antitumor effects of anti-CD20 antibodies.
Zhang (2009) mAbs 1:326-331. Ofatumumab.
Deng et al. (2012) Blood 120(21):3725. Poster Abstract: Novel PI3K Inhibitors Demonstrated Marked Cytotoxicity in T Cell Lymphoma Models, Caused Apoptosis and Were Synergistic with a Novel Anti-CD20 Monoclonal Antibody Ublituximab in B Cell Lymphoma Models (Nov. 16, 2012).

(Continued)

*Primary Examiner* — Karen Canella
(74) *Attorney, Agent, or Firm* — Wilson IP Law; M. Lisa Wilson

(57) ABSTRACT

Highly effective combinations of a compound of formula A (a PI3Kδ selective inhibitor) and anti-CD20 antibodies are provided herein for the treatment and amelioration of PI3Kδ and/or CD20 mediated diseases and disorders. In particular, the combination can be used to treat cancers and autoimmune diseases. More particularly, the invention provided for a combination of a compound of formula A, or stereoisomers thereof, and ublituximab for the treatment and/or amerioration of hematological malignancies such as leukemia and lymphoma.

25 Claims, 12 Drawing Sheets

(56) References Cited

OTHER PUBLICATIONS

Figure 1:
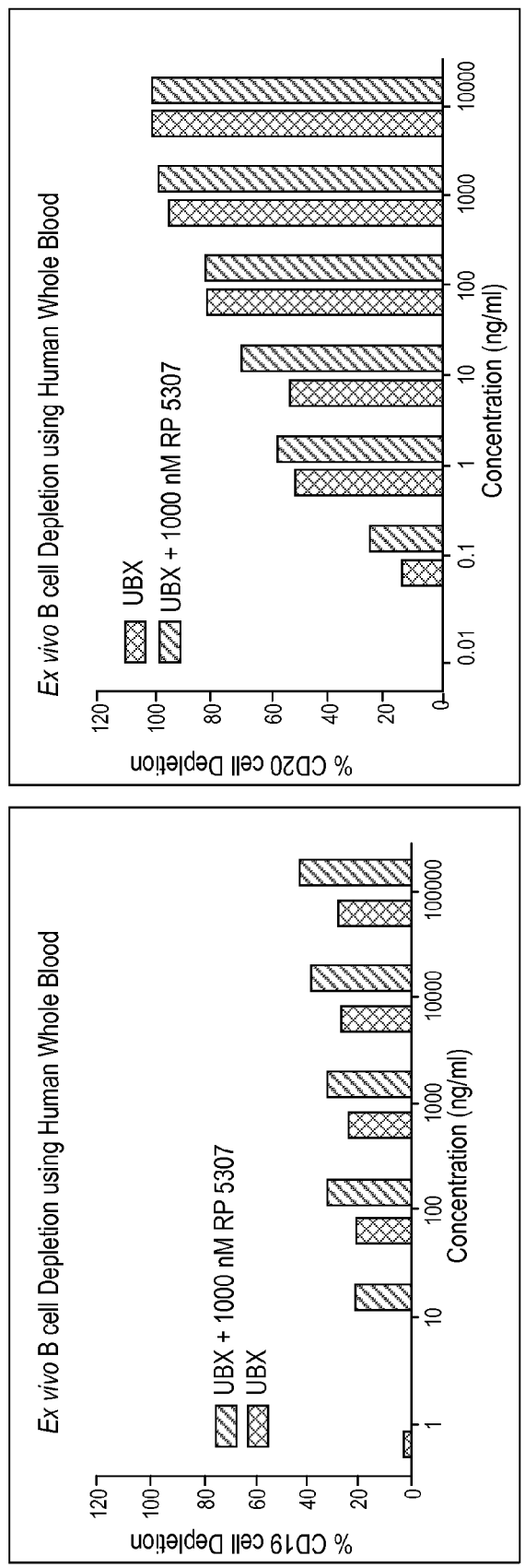

Deng et al. Poster Presentation at ASH Annual Meeting Dec. 8-11, 2012. Novel PI3K Inhibitors Demonstrated Marked Cytotoxicity in T Cell Lymphoma Models, Caused Apoptosis and Were Synergistic with a Novel Anti-CD20 Monoclonal Antibody Ublituximab in B Cell Lymphoma Models.

* cited by examiner

SEQUENCE LISTING

<160> NUMBER OF SEQ ID NOS: 10

<210> SEQ ID NO 1
<211> LENGTH: 8
<212> TYPE: PRT
<213> ORGANISM: Artificial Sequence
<220> FEATURE:
<223> OTHER INFORMATION: antibody fragment

<400> SEQUENCE: 1

Gly Tyr Thr Phe Thr Ser Tyr Asn
1               5

<210> SEQ ID NO 2
<211> LENGTH: 8
<212> TYPE: PRT
<213> ORGANISM: Artificial Sequence
<220> FEATURE:
<223> OTHER INFORMATION: antibody fragment

<400> SEQUENCE: 2

Ile Tyr Pro Gly Asn Gly Asp Thr
1               5

<210> SEQ ID NO 3
<211> LENGTH: 11
<212> TYPE: PRT
<213> ORGANISM: Artificial Sequence
<220> FEATURE:
<223> OTHER INFORMATION: antibody fragment

<400> SEQUENCE: 3

Ala Arg Tyr Asp Tyr Asn Tyr Ala Met Asp Tyr
1               5                   10

<210> SEQ ID NO 4
<211> LENGTH: 118
<212> TYPE: PRT
<213> ORGANISM: Artificial Sequence
<220> FEATURE:
<223> OTHER INFORMATION: antibody fragment

<400> SEQUENCE: 4

Gln Ala Tyr Leu Gln Gln Ser Gly Ala Glu Leu Val Arg Pro Gly Ala
1               5                   10                  15

Ser Val Lys Met Ser Cys Lys Ala Ser Gly Tyr Thr Phe Thr Ser Tyr
            20                  25                  30

Asn Met His Trp Val Lys Gln Thr Pro Arg Gln Gly Leu Glu Trp Ile
        35                  40                  45

Gly Gly Ile Tyr Pro Gly Asn Gly Asp Thr Ser Tyr Asn Gln Lys Phe
    50                  55                  60

Lys Gly Lys Ala Thr Leu Thr Val Gly Lys Ser Ser Thr Ala Tyr
65                  70                  75                  80

Met Gln Leu Ser Ser Leu Thr Ser Glu Asp Ser Ala Val Tyr Phe Cys
                85                  90                  95

Ala Arg Tyr Asp Tyr Asn Tyr Ala Met Asp Tyr Trp Gly Gln Gly Thr
            100                 105                 110

Ser Val Thr Val Ser Ser
        115

<210> SEQ ID NO 5
<211> LENGTH: 330
<212> TYPE: PRT
<213> ORGANISM: Artificial Sequence
<220> FEATURE:
<223> OTHER INFORMATION: antibody fragment

<400> SEQUENCE: 5

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

```
Gly Val His Thr Phe Pro Ala Val Leu Gln Ser Ser Gly Leu Tyr Ser
         50                  55                  60

Leu Ser Ser Val Val Thr Val Pro Ser Ser Ser Leu Gly Thr Gln Thr
 65                  70                  75                  80

Tyr Ile Cys Asn Val Asn His Lys Pro Ser Asn Thr Lys Val Asp Lys
                 85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
            115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
            195                 200                 205

Lys Ala Leu Pro Ala Pro Ile Glu Lys Thr Ile Ser Lys Ala Lys Gly
210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 6
<211> LENGTH: 5
<212> TYPE: PRT
<213> ORGANISM: Artificial Sequence
<220> FEATURE:
<223> OTHER INFORMATION: antibody fragment

<400> SEQUENCE: 6

Ser Ser Val Ser Tyr
1               5

<210> SEQ ID NO 7
<211> LENGTH: 3
<212> TYPE: PRT
<213> ORGANISM: Artificial Sequence
<220> FEATURE:
<223> OTHER INFORMATION: antibody fragment

<400> SEQUENCE: 7

Ala Thr Ser
```

<210> SEQ ID NO 8
<211> LENGTH: 9
<212> TYPE: PRT
<213> ORGANISM: Artificial Sequence
<220> FEATURE:
<223> OTHER INFORMATION: antibody fragment

<400> SEQUENCE: 8

```
Gln Gln Trp Thr Phe Asn Pro Pro Thr
1               5
```

<210> SEQ ID NO 9
<211> LENGTH: 106
<212> TYPE: PRT
<213> ORGANISM: Artificial Sequence
<220> FEATURE:
<223> OTHER INFORMATION: antibody fragment

<400> SEQUENCE: 9

```
Gln Ile Val Leu Ser Gln Ser Pro Ala Ile Leu Ser Ala Ser Pro Gly
1               5                   10                  15
Glu Lys Val Thr Met Thr Cys Arg Ala Ser Ser Val Ser Tyr Met
            20                  25                  30
His Trp Tyr Gln Gln Lys Pro Gly Ser Ser Pro Lys Pro Trp Ile Tyr
        35                  40                  45
Ala Thr Ser Asn Leu Ala Ser Gly Val Pro Ala Arg Phe Ser Gly Ser
    50                  55                  60
Gly Ser Gly Thr Ser Tyr Ser Phe Thr Ile Ser Arg Val Glu Ala Glu
65                  70                  75                  80
Asp Ala Ala Thr Tyr Tyr Cys Gln Gln Trp Thr Phe Asn Pro Pro Thr
                85                  90                  95
Phe Gly Gly Gly Thr Arg Leu Glu Ile Lys
            100                 105
```

<210> SEQ ID NO 10
<211> LENGTH: 106
<212> TYPE: PRT
<213> ORGANISM: Artificial Sequence
<220> FEATURE:
<223> OTHER INFORMATION: antibody fragment

<400> SEQUENCE: 10

```
Thr Val Ala Ala Pro Ser Val Phe Ile Phe Pro Pro Ser Asp Glu Gln
1               5                   10                  15
Leu Lys Ser Gly Thr Ala Ser Val Val Cys Leu Leu Asn Asn Phe Tyr
            20                  25                  30
Pro Arg Glu Ala Lys Val Gln Trp Lys Val Asp Asn Ala Leu Gln Ser
        35                  40                  45
Gly Asn Ser Gln Glu Ser Val Thr Glu Gln Asp Ser Lys Asp Ser Thr
    50                  55                  60
Tyr Ser Leu Ser Ser Thr Leu Thr Leu Ser Lys Ala Asp Tyr Glu Lys
65                  70                  75                  80
His Lys Val Tyr Ala Cys Glu Val Thr His Gln Gly Leu Ser Ser Pro
                85                  90                  95
Val Thr Lys Ser Phe Asn Arg Gly Glu Cys
            100                 105
```

COMBINATION OF ANTI-CD20 ANTIBODY AND PI3 KINASE SELECTIVE INHIBITOR

This application is a national stage filing under 35 U.S. §371 of Intl. Appln. No. PCT/US2013/067956, filed Nov. 1, 2013, which claims priority under 35 U.S.C. §119(e) of provisional application U.S. Ser. No. 61/771,812, filed Mar. 2, 2013, each of which is incorporated herein by reference in its entirety.

INCORPORATION BY REFERENCE OF SEQUENCE LISTING

The Sequence Listing in the ASCII text file, identified by the name 43-101us2_ST25.txt, created Oct. 30, 2013 with a size of 8000 bytes and submitted to the United States Patent and Trademark Office via EFS-Web, is incorporated herein by reference.

FIELD OF THE INVENTION

Highly effective combinations of a compound of formula A (a PI3Kδ selective inhibitor) and anti-CD20 antibodies are provided herein for the treatment and amelioration of PI3Kδ and/or CD20 mediated diseases and disorders. In particular, the combination can be used to treat cancers and autoimmune diseases. More particularly, the invention provided for a combination of a compound of formula A, or stereoisomers thereof, and ublituximab for the treatment and/or amerioration of hematological malignancies such as leukemia and lymphoma.

BACKGROUND OF THE INVENTION

There is considerable evidence indicating that both PI3Kδ enzymes and CD20 contribute individually to tumorigenesis in a wide variety of human cancers and especially in hematological malignancies. The phosphoinositide 3-kinases (PI3Ks) are a family of enzymes that regulate diverse biological functions in every cell type by generating phosphoinositide second-messenger molecules. As the activity of these phosphoinositide second messengers is determined by their phosphorylation state, the kinases and phosphatises that act to modify these lipids are central to the correct execution of intracellular signaling events. PI3Ks phosphorylate lipids at the 3-hydroxyl residue of an inositol ring (Whitman et al., *Nature* 332:664 (1988)) to generate phosphorylated phospholipids (PIP3s) which act as second messengers recruiting kinases with lipid binding domains (including plekstrin homology (PH) regions), such as Akt and phosphoinositide-dependent kinase-1 (PDK1). Binding of Akt to membrane PIP3s causes the translocation of Akt to the plasma membrane, bringing Akt into contact with PDK1, which is responsible for activating Akt. The tumor-suppressor phosphatase, PTEN (Phosphatase and Tensin homolog deleted on chromosome Ten), dephosphorylates PIP3 and therefore acts as a negative regulator of Akt activation. The PI3-kinases Akt and PDK1 are important in the regulation of many cellular processes including cell cycle regulation, proliferation, survival, apoptosis and motility and are significant components of the molecular mechanisms of diseases such as cancer, diabetes and immune inflammation (Vivanco et al., *Nature Rev. Cancer* 2:489 (2002); Phillips et al., *Cancer* 83:41 (1998)).

The PI3Ks family is constituted by four different classes: Classes I, II, III and IV. Classes I-III are lipid kinases and Class IV are serine/threonine protein kinases.

The members of the Class I family of PI3Ks are dimers of a regulatory and a catalytic subunit. The Class I family consists of four isoforms, determined by the 110 kDa catalytic subunits α, β, γ and δ. See Engelman J. A., *Nat Rev Genet* 7:606-619 (2006); Carnero A., *Curr Cancer Drug Targets* 8:187-198 (2008); and Vanhaesebroeck B., *Trends Biochem Sci* 30:194-204 (2005). Class I can be subdivided into two subclasses: Class Ia, formed by the combination of p110 α, β, and δ, and a regulatory subunit (p85, p55 or p50); and Class Ib, formed by p110 γ and p101 regulatory subunits.

Studies regarding PI3K and related protein kinase pathways have been published by various research groups, including, Liu et al., *Nature Reviews Drug Discovery* 8:627-644 (2009); Nathan et al, *Mol. Cancer Ther.* 8(1) (2009); and Marone et al., *Biochimica et Biophysica Acta* 1784:159-185 (2008). Two known PI3K inhibitors, LY294002 and Wortmannin, are non-specific PI3K inhibitors as they do not distinguish the four members of Class I PI3K: α, β, γ, and δ. A number of PI3K inhibitors have entered clinical trials for the treatment of cancers, and various types of cancers, including breast cancer, non-small cell lung cancer (NSCLC), and hematological cancers, are being considered as areas of therapeutic interest.

CD20 is a hydrophobic transmembrane protein with a molecular weight of 35-37 kDa which is present on the surface of mature B lymphocytes. It is expressed during the development of B lymphocyte cells (B cells) as from the early pre-B stage until differentiation into plasmocytes, a stage at which this expression disappears. CD20 is present on both normal B lymphocytes and malignant B cells including most non-Hodgkin's B-cell lymphomas (NHL) and B-type Chronic Lymphocytic Leukemia's (B-CLL). The CD20 antigen is not expressed on haematopoietic stem cells or on plasmocytes.

Anti-CD20 antibodies have been, and continue to be, developed for the treatment of B-cell diseases. Successes have been reported for the anti-CD20 antibody rituximab. However, there are a substantial number of patients who are refractory to treatment with rituximab or who develop resistance in the course of prolonged treatment with rituximab (used as a single agent or even in combination with chemotherapeutic regimens).

Accordingly, there is a need for more effective therapies for the treatment and/or amelioration of diseases or disorders associated with modulation of PI3Kδ enzymes and/or CD20 protein, and in particular for the treatment and or amelioration of B-cell diseases.

BRIEF SUMMARY OF THE INVENTION

The present invention is directed to a combination comprising of a compound of formula (A) that is a PI3Kδ selective inhibitor,

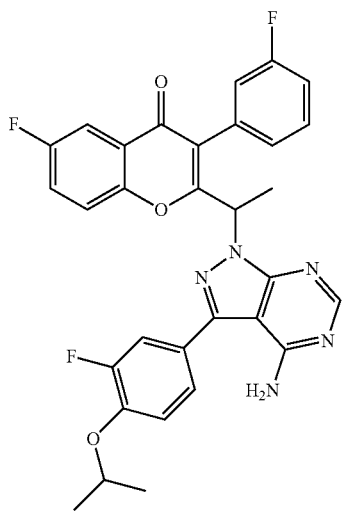

(A)

and a stereoisomer thereof, a tautomer thereof, pharmaceutically acceptable salts, solvates, and prodrugs thereof, and at least one anti-CD20 antibody.

The combination is suitable for use in the treatment of a PI3Kδ enzyme- and/or CD20 protein-associated disease, disorder or condition, e.g., a proliferative disease such as cancer. In particular, the combination is suitable for the treatment and or amelioration of B-cell diseases, e.g., hematological malignancies.

Thus, in some embodiments, methods of inhibiting proliferation of a cell population are provided. In some embodiments, the method comprises contacting the population with a combination comprising (i) a compound of formula A, a stereoisomer thereof, a tautomer thereof, or a pharmaceutically acceptable salt, solvate, or prodrug thereof, (ii) and an anti-CD20 antibody or antigen-binding fragment thereof, wherein the anti-CD20 antibody or fragment binds to the same epitope as ublituximab.

In some embodiments, the method comprises contacting the cell population with a combination comprising (i) a compound of formula A, a stereoisomer thereof, a tautomer thereof, or a pharmaceutically acceptable salt, solvate, or prodrug thereof, and (ii) an anti-CD20 antibody or antigen-binding fragment thereof, wherein the anti-CD20 antibody or fragment exhibits a high affinity to Fc-gammaRIII (CD16).

In some embodiments, the method comprises contacting the cell population with a combination comprising (i) a compound of formula A, a stereoisomer thereof, a tautomer thereof, or a pharmaceutically acceptable salt, solvate, or prodrug thereof, and (ii) an anti-CD20 antibody or antigen-binding fragment thereof, wherein the fucose content of the antibody or fragment is less than 65%.

In some embodiments, the method comprises contacting the cell population with a combination comprising (i) a compound of formula A, a stereoisomer thereof, a tautomer thereof, or a pharmaceutically acceptable salt, solvate, or prodrug thereof, and (ii) an anti-CD20 antibody or antigen-binding fragment thereof, wherein the antibody or fragment comprises the VH CDR1, CDR2 and CDR3 region of sequences SEQ ID NO:1, 2, and 3, and the VL CDR1, CDR2 and CDR3 region of sequences SEQ ID NO:6, 7, and 8. In some embodiments, the anti-CD20 antibody or antigen-binding fragment thereof comprises the VH of SEQ ID NO:4 and the VL of SEQ ID NO:9. In some embodiments, the anti-CD20 antibody is ublituximab.

In some embodiments, the compound of formula A is
(RS)-2-(1-(4-amino-3-(3-fluoro-4-isopropoxyphenyl)-1H-pyrazolo[3,4-d]pyrimidin-1-yl)ethyl)-6-fluoro-3-(3-fluorophenyl)-4H-chromen-4-one;
(S)-2-(1-(4-amino-3-(3-fluoro-4-isopropoxyphenyl)-1H-pyrazolo[3,4-d]pyrimidin-1-yl)ethyl)-6-fluoro-3-(3-fluorophenyl)-4H-chromen-4-one; or
(R)-2-(1-(4-amino-3-(3-fluoro-4-isopropoxyphenyl)-1H-pyrazolo[3,4-d]pyrimidin-1-yl)ethyl)-6-fluoro-3-(3-fluorophenyl)-4H-chromen-4-one.

In some embodiments, the compound of formula A is
(S)-2-(1-(4-amino-3-(3-fluoro-4-isopropoxyphenyl)-1H-pyrazolo[3,4-d]pyrimidin-1-yl)ethyl)-6-fluoro-3-(3-fluorophenyl)-4H-chromen-4-one.

In some embodiments, a method of inhibiting proliferation of a cell population comprises contacting the population with a combination comprising (i) at least one compound selected from the group consisting of 2-(1-(4-amino-3-(3-fluoro-4-isopropoxyphenyl)-1H-pyrazolo[3,4-d]pyrimidin-1-yl)ethyl)-6-fluoro-3-(3-fluorophenyl)-4H-chromen-4-one; (S)-2-(1-(4-amino-3-(3-fluoro-4-isopropoxyphenyl)-1H-pyrazolo[3,4-d]pyrimidin-1-yl)ethyl)-6-fluoro-3-(3-fluorophenyl)-4H-chromen-4-one; and (R)-2-(1-(4-amino-3-(3-fluoro-4-isopropoxyphenyl)-1H-pyrazolo[3,4-d]pyrimidin-1-yl)ethyl)-6-fluoro-3-(3-fluorophenyl)-4H-chromen-4-one, and (ii) at least one anti-CD20 antibody or antigen-binding fragment thereof.

In some embodiments, a method of inhibiting proliferation of a cell population comprises contacting the population with a combination comprising (i) a compound selected from the group consisting of 2-(1-(4-amino-3-(3-fluoro-4-isopropoxyphenyl)-1H-pyrazolo[3,4-d]pyrimidin-1-yl) ethyl)-6-fluoro-3-(3-fluorophenyl)-4H-chromen-4-one; (S)-2-(1-(4-amino-3-(3-fluoro-4-isopropoxyphenyl)-1H-pyrazolo[3,4-d]pyrimidin-1-yl)ethyl)-6-fluoro-3-(3-fluorophenyl)-4H-chromen-4-one; and (R)-2-(1-(4-amino-3-(3-fluoro-4-isopropoxyphenyl)-1H-pyrazolo[3,4-d]pyrimidin-1-yl)ethyl)-6-fluoro-3-(3-fluorophenyl)-4H-chromen-4-one, and (ii) at least one anti-CD20 antibody or antigen-binding fragment thereof, wherein the anti-CD20 antibody or fragment thereof is selected from the group consisting of antibodies and fragments thereof that bind to the same epitope as ublituximab, rituximab, ofatumumab, ocrelizumab, veltuzumab, GA101, AME-133v, PRO131921, tositumomab, hA20, and PRO70769.

In some embodiments, the population is contacted with a composition comprising (i) a compound selected from the group consisting of
2-(1-(4-amino-3-(3-fluoro-4-isopropoxyphenyl)-1H-pyrazolo[3,4-d]pyrimidin-1-yl)ethyl)-6-fluoro-3-(3-fluorophenyl)-4H-chromen-4-one;
(S)-2-(1-(4-amino-3-(3-fluoro-4-isopropoxyphenyl)-1H-pyrazolo[3,4-d]pyrimidin-1-yl)ethyl)-6-fluoro-3-(3-fluorophenyl)-4H-chromen-4-one; and
(R)-2-(1-(4-amino-3-(3-fluoro-4-isopropoxyphenyl)-1H-pyrazolo[3,4-d]pyrimidin-1-yl)ethyl)-6-fluoro-3-(3-fluorophenyl)-4H-chromen-4-one, and
(ii) the anti-CD20 antibody.

In some embodiments, the population is contacted with (i) a first composition comprising a compound selected from the group consisting of
2-(1-(4-amino-3-(3-fluoro-4-isopropoxyphenyl)-1H-pyrazolo[3,4-d]pyrimidin-1-yl)ethyl)-6-fluoro-3-(3-fluorophenyl)-4H-chromen-4-one;

(S)-2-(1-(4-amino-3-(3-fluoro-4-isopropoxyphenyl)-1H-pyrazolo[3,4-d]pyrimidin-1-yl)ethyl)-6-fluoro-3-(3-fluorophenyl)-4H-chromen-4-one; and 1-(4-amino-3-(3-fluoro-4-isopropoxyphenyl)-1H-pyrazolo[3,4-d]pyrimidin-1-yl)ethyl)-6-fluoro-3-(3-fluorophenyl)-4H-chromen-4-one, and (ii) a second composition comprising the anti-CD20 antibody.

In some embodiments, the population comprises B-cells.

In some embodiments, the population is in a human subject.

In some embodiments, the subject has a disease or disorder associated with excessive B-cell proliferation.

In some embodiments, the subject has cancer. In some embodiments, the cancer is a hematological malignancy. In some embodiments, the hematological malignancy is lymphoma or leukemia. In some embodiments, the hematological malignancy is selected from the group consisting of acute lymphocytic leukemia (ALL), acute myeloid leukemia (AML), chronic lymphocytic leukemia (CLL), small lymphocytic lymphoma (SLL), multiple myeloma (MM), non-Hodgkin's lymphoma (NHL), mantle cell lymphoma (MCL), follicular lymphoma, Waldenstrom's macroglobulinemia (WM), B-cell lymphoma and diffuse large B-cell lymphoma (DLBCL). In some embodiments, the cancer overexpresses CD20. In some embodiments, the cancer is refractory to chemotherapy.

In some embodiments, the subject has an autoimmune disease or disorder. In some embodiments, the autoimmune disease or disorder is allergic rhinitis, asthma, chronic obstructive pulmonary disease (COPD), or rheumatoid arthritis.

In some embodiments, the subject is refractory to rituximab.

In some embodiments, the subject has previously been treated with chemotherapy, rituximab, or a combination thereof.

In some embodiments, the (S)-2-(1-(4-amino-3-(3-fluoro-4-isopropoxyphenyl)-1H-pyrazolo[3,4-d]pyrimidin-1-yl)ethyl)-6-fluoro-3-(3-fluorophenyl)-4H-chromen-4-one and the anti-CD20 antibody or fragment are administered sequentially.

In some embodiments, the (S)-2-(1-(4-amino-3-(3-fluoro-4-isopropoxyphenyl)-1H-pyrazolo[3,4-d]pyrimidin-1-yl)ethyl)-6-fluoro-3-(3-fluorophenyl)-4H-chromen-4-one and the anti-CD20 antibody or fragment are administered simultaneously. In some embodiments, the (S)-2-(1-(4-amino-3-(3-fluoro-4-isopropoxyphenyl)-1H-pyrazolo[3,4-d]pyrimidin-1-yl)ethyl)-6-fluoro-3-(3-fluorophenyl)-4H-chromen-4-one and the anti-CD20 antibody or fragment are contained in the same pharmaceutical composition. In some embodiments, the (S)-2-(1-(4-amino-3-(3-fluoro-4-isopropoxyphenyl)-1H-pyrazolo[3,4-d]pyrimidin-1-yl)ethyl)-6-fluoro-3-(3-fluorophenyl)-4H-chromen-4-one, and the anti-CD20 antibody or fragment are in separate pharmaceutical compositions.

In some embodiments, the method further comprises administering at least one additional therapeutic agent to the subject. In some embodiments, the at least one additional therapeutic agent is selected from the group consisting of a proteasome inhibitor, Bortezomib (Velcade®), Carfilzomib (PR-171), PR-047, disulfiram, lactacystin, PS-519, epoxemycin, epoxomycin, aclacinomycin, CEP-1612, MG-132, CVT-63417, PS-341, vinyl sulfone tripeptide inhibitors, ritonavir, PI-083, (+/−)-7-methylomuralide, (−)-7-methylomuralide, lenalidomide, and combinations thereof.

In some embodiments, the method further comprises administering at least two additional therapeutic agents to the subject, wherein the at least two additional therapeutic agents are selected from the group consisting of: a) CHOP (cyclophosphamide, doxorubicin, vincristine, prednisone); b) R-CHOP (rituximab-CHOP); c) hyperCV AD (hyperfractionated cyclophosphamide, vincristine, doxorubicin, dexamethasone, methotrexate, cytarabine); d) R-hyperCV AD (rituximab-hyperCV AD); e) FCM (fludarabine, cyclophosphamide, mitoxantrone); f) R-FCM (rituximab, fludarabine, cyclophosphamide, mitoxantrone); g) bortezomib and rituximab; h) temsirolimus and rituximab; i) temsirolimus and Velcade®; j) Iodine-131 tositumomab (Bexxar®) and CHOP; k) CVP (cyclophosphamide, vincristine, prednisone); l) R-CVP (rituximab-CVP); m) ICE (iphosphamide, carboplatin, etoposide); n) R-ICE (rituximab-ICE); o) FCR (fludarabine, cyclophosphamide, rituximab); p) FR (fludarabine, rituximab); and q) D.T. PACE (Dexamethasone, Thalidomide, Cisplatin, Adriamycin, Cyclophosphamide, Etoposide).

In some embodiments, methods for depleting B-cells are provided. In some embodiments, the method comprises contacting a composition comprising B-cells with (i) at least one compound of formula A selected from the group consisting of 2-(1-(4-amino-3-(3-fluoro-4-isopropoxyphenyl)-1H-pyrazolo[3,4-d]pyrimidin-1-yl)ethyl)-6-fluoro-3-(3-fluorophenyl)-4H-chromen-4-one; (S)-2-(1-(4-amino-3-(3-fluoro-4-isopropoxyphenyl)-1H-pyrazolo[3,4-d]pyrimidin-1-yl)ethyl)-6-fluoro-3-(3-fluorophenyl)-4H-chromen-4-one; and (R)-2-(1-(4-amino-3-(3-fluoro-4-isopropoxyphenyl)-1H-pyrazolo[3,4-d]pyrimidin-1-yl)ethyl)-6-fluoro-3-(3-fluorophenyl)-4H-chromen-4-one, and (ii) at least one anti-CD20 antibody or antigen-binding fragment thereof.

In some embodiments, method for promoting apoptosis are provided. In some embodiments, the methods comprise contacting a B-cell with (i) at least one compound of formula A selected from the group consisting of 2-(1-(4-amino-3-(3-fluoro-4-isopropoxyphenyl)-1H-pyrazolo[3,4-d]pyrimidin-1-yl)ethyl)-6-fluoro-3-(3-fluorophenyl)-4H-chromen-4-one; (S)-2-(1-(4-amino-3-(3-fluoro-4-isopropoxyphenyl)-1H-pyrazolo[3,4-d]pyrimidin-1-yl)ethyl)-6-fluoro-3-(3-fluorophenyl)-4H-chromen-4-one; and (R)-2-(1-(4-amino-3-(3-fluoro-4-isopropoxyphenyl)-1H-pyrazolo[3,4-d]pyrimidin-1-yl)ethyl)-6-fluoro-3-(3-fluorophenyl)-4H-chromen-4-one, and (ii) at least one anti-CD20 antibody or antigen-binding fragment thereof.

In some embodiments, methods for promoting cell-cycle arrest are provided. In some embodiments, the methods comprise contacting a cell with (i) at least one compound of formula A selected from the group consisting of 2-(1-(4-amino-3-(3-fluoro-4-isopropoxyphenyl)-1H-pyrazolo[3,4-d]pyrimidin-1-yl)ethyl)-6-fluoro-3-(3-fluorophenyl)-4H-chromen-4-one; (S)-2-(1-(4-amino-3-(3-fluoro-4-isopropoxyphenyl)-1H-pyrazolo[3,4-d]pyrimidin-1-yl)ethyl)-6-fluoro-3-(3-fluorophenyl)-4H-chromen-4-one; and (R)-2-(1-(4-amino-3-(3-fluoro-4-isopropoxyphenyl)-1H-pyrazolo[3,4-d]pyrimidin-1-yl)ethyl)-6-fluoro-3-(3-fluorophenyl)-4H-chromen-4-one, and (ii) at least one anti-CD20 antibody or antigen-binding fragment thereof.

In some embodiments, the compound of formula A and the anti-CD20 antibody or fragment are delivered sequentially.

In some embodiments, the compound of formula A and the anti-CD20 antibody or fragment are delivered simultaneously. In some embodiments, the compound of formula A and the anti-CD20 antibody or fragment are delivered in the same composition. In some embodiments, the compound of formula A and the anti-CD20 antibody or fragment are delivered in separate compositions.

Kits are also provided herein. In some embodiments, the kit comprises (i) a compound of formula A, a stereoisomer thereof, a tautomer thereof, or a pharmaceutically acceptable salt, solvate, or prodrug thereof, and (ii) instructions for using the compound in combination with an anti-CD20 antibody or antigen-binding fragment thereof, wherein the anti-CD20 antibody or fragment (a) binds to the same epitope as ublituximab, (b) exhibits a high affinity to Fc-gammaRIII (CD16), or (c) or has a fucose content of less than 65%.

In some embodiments, the kit comprises (i) at least one compound selected from the group consisting of
2-(1-(4-amino-3-(3-fluoro-4-isopropoxyphenyl)-1H-pyrazolo[3,4-d]pyrimidin-1-yl)ethyl)-6-fluoro-3-(3-fluorophenyl)-4H-chromen-4-one;
(S)-2-(1-(4-amino-3-(3-fluoro-4-isopropoxyphenyl)-1H-pyrazolo[3,4-d]pyrimidin-1-yl)ethyl)-6-fluoro-3-(3-fluorophenyl)-4H-chromen-4-one; and
(R)-2-(1-(4-amino-3-(3-fluoro-4-isopropoxyphenyl)-1H-pyrazolo[3,4-d]pyrimidin-1-yl)ethyl)-6-fluoro-3-(3-fluorophenyl)-4H-chromen-4-one, and
(ii) instructions for using the compound in combination with an anti-CD20 antibody or antigen-binding fragment thereof.

In some embodiments, the kit further comprises the anti-CD20 antibody or fragment.

In some embodiments, the kit comprises (i) at least one anti-CD20 antibody or antigen-binding fragment thereof and (ii) instructions for using the anti-CD20 antibody or fragment in combination with at least one compound selected from the group consisting of
2-(1-(4-amino-3-(3-fluoro-4-isopropoxyphenyl)-1H-pyrazolo[3,4-d]pyrimidin-1-yl)ethyl)-6-fluoro-3-(3-fluorophenyl)-4H-chromen-4-one;
(S)-2-(1-(4-amino-3-(3-fluoro-4-isopropoxyphenyl)-1H-pyrazolo[3,4-d]pyrimidin-1-yl)ethyl)-6-fluoro-3-(3-fluorophenyl)-4H-chromen-4-one; and
(R)-2-(1-(4-amino-3-(3-fluoro-4-isopropoxyphenyl)-1H-pyrazolo[3,4-d]pyrimidin-1-yl)ethyl)-6-fluoro-3-(3-fluorophenyl)-4H-chromen-4-one,
wherein the anti-CD20 antibody or a fragment thereof (a) binds to the same epitope as ublituximab, (b) exhibits a high affinity to Fc-gammaRIII (CD16), or (c) has a fucose of less than 65%.

In some embodiments, the kit comprises (i) at least one anti-CD20 antibody or antigen-binding fragment thereof and (ii) instructions for using the anti-CD20 antibody or fragment in combination with at least one compound selected from the group consisting of
2-(1-(4-amino-3-(3-fluoro-4-isopropoxyphenyl)-1H-pyrazolo[3,4-d]pyrimidin-1-yl)ethyl)-6-fluoro-3-(3-fluorophenyl)-4H-chromen-4-one;
(S)-2-(1-(4-amino-3-(3-fluoro-4-isopropoxyphenyl)-1H-pyrazolo[3,4-d]pyrimidin-1-yl)ethyl)-6-fluoro-3-(3-fluorophenyl)-4H-chromen-4-one; and,
(R)-2-(1-(4-amino-3-(3-fluoro-4-isopropoxyphenyl)-1H-pyrazolo[3,4-d]pyrimidin-1-yl)ethyl)-6-fluoro-3-(3-fluorophenyl)-4H-chromen-4-one.

In some embodiments, the kit comprises (i) a compound selected from the group consisting of
2-(1-(4-amino-3-(3-fluoro-4-isopropoxyphenyl)-1H-pyrazolo[3,4-d]pyrimidin-1-yl)ethyl)-6-fluoro-3-(3-fluorophenyl)-4H-chromen-4-one;
(S)-2-(1-(4-amino-3-(3-fluoro-4-isopropoxyphenyl)-1H-pyrazolo[3,4-d]pyrimidin-1-yl)ethyl)-6-fluoro-3-(3-fluorophenyl)-4H-chromen-4-one; and
(R)-2-(1-(4-amino-3-(3-fluoro-4-isopropoxyphenyl)-1H-pyrazolo[3,4-d]pyrimidin-1-yl)ethyl)-6-fluoro-3-(3-fluorophenyl)-4H-chromen-4-one, and
(ii) an anti-CD20 antibody or antigen-binding fragment thereof, wherein the anti-CD20 antibody or fragment (a) binds to the same epitope as ublituximab, (b) exhibits a high affinity to Fc-gammaRIII (CD16), or (c) has a fucose content of less than 65%.

In some embodiments, the kit comprises (i) a compound selected from the group consisting of
2-(1-(4-amino-3-(3-fluoro-4-isopropoxyphenyl)-1H-pyrazolo[3,4-d]pyrimidin-1-yl)ethyl)-6-fluoro-3-(3-fluorophenyl)-4H-chromen-4-one;
(S)-2-(1-(4-amino-3-(3-fluoro-4-isopropoxyphenyl)-1H-pyrazolo[3,4-d]pyrimidin-1-yl)ethyl)-6-fluoro-3-(3-fluorophenyl)-4H-chromen-4-one; and
(R)-2-(1-(4-amino-3-(3-fluoro-4-isopropoxyphenyl)-1H-pyrazolo[3,4-d]pyrimidin-1-yl)ethyl)-6-fluoro-3-(3-fluorophenyl)-4H-chromen-4-one, and
(ii) an anti-CD20 antibody or antigen-binding fragment thereof.

In some embodiments, the anti-CD20 antibody or fragment and the compound are contained within the same composition.

In some embodiments, the anti-CD20 antibody or fragment and the compound are in separate compositions.

In some embodiments, the kit further comprises one or more additional active agents.

Pharmaceutical compositions are also provided herein. In some embodiments, the pharmaceutical composition comprises (i) a compound selected from the group consisting of
2-(1-(4-amino-3-(3-fluoro-4-isopropoxyphenyl)-1H-pyrazolo[3,4-d]pyrimidin-1-yl)ethyl)-6-fluoro-3-(3-fluorophenyl)-4H-chromen-4-one;
(S)-2-(1-(4-amino-3-(3-fluoro-4-isopropoxyphenyl)-1H-pyrazolo[3,4-d]pyrimidin-1-yl)ethyl)-6-fluoro-3-(3-fluorophenyl)-4H-chromen-4-one; and
(R)-2-(1-(4-amino-3-(3-fluoro-4-isopropoxyphenyl)-1H-pyrazolo[3,4-d]pyrimidin-1-yl)ethyl)-6-fluoro-3-(3-fluorophenyl)-4H-chromen-4-one, and
(ii) an anti-CD20 antibody or antigen-binding fragment thereof.

In some embodiments, the pharmaceutical composition comprises (i) a compound selected from the group consisting of
2-(1-(4-amino-3-(3-fluoro-4-isopropoxyphenyl)-1H-pyrazolo[3,4-d]pyrimidin-1-yl)ethyl)-6-fluoro-3-(3-fluorophenyl)-4H-chromen-4-one;
(S)-2-(1-(4-amino-3-(3-fluoro-4-isopropoxyphenyl)-1H-pyrazolo[3,4-d]pyrimidin-1-yl)ethyl)-6-fluoro-3-(3-fluorophenyl)-4H-chromen-4-one; and
(R)-2-(1-(4-amino-3-(3-fluoro-4-isopropoxyphenyl)-1H-pyrazolo[3,4-d]pyrimidin-1-yl)ethyl)-6-fluoro-3-(3-fluorophenyl)-4H-chromen-4-one, and
(ii) an anti-CD20 antibody or antigen-binding fragment thereof, wherein the anti-CD20 antibody or fragment (a) binds to the same epitope as ublituximab, (b) exhibits a high affinity to Fc-gammaRIII (CD16), or (c) has a fucose content less than 65%.

BRIEF DESCRIPTION OF THE DRAWINGS/FIGURES

FIG. 1: Bar graphs showing the effect of S-isomer of a compound of formula A and Ublituximab on CD19-positive cell depletion (left) and CD20-positive cell depletion (right) from human whole blood.

Figure 2:
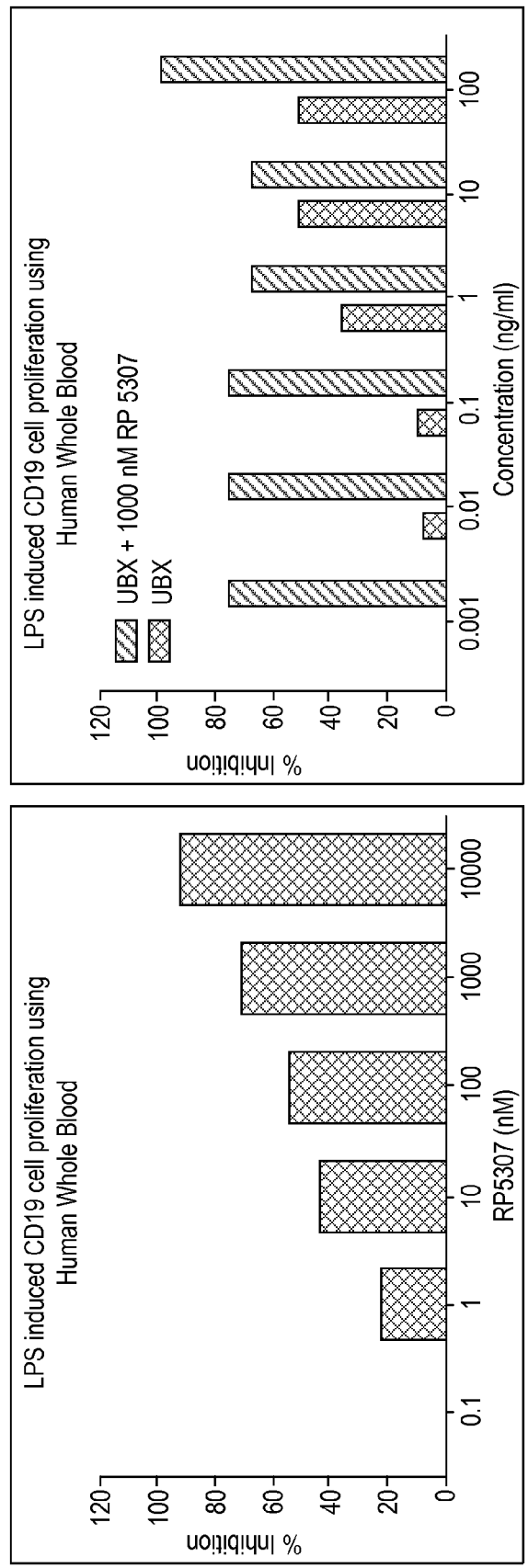

FIG. 2: Bar graphs showing the effect of S-isomer of a compound of formula A and Ublituximab on LPS-induced CD19-positive cell proliferation.

Figure 3:
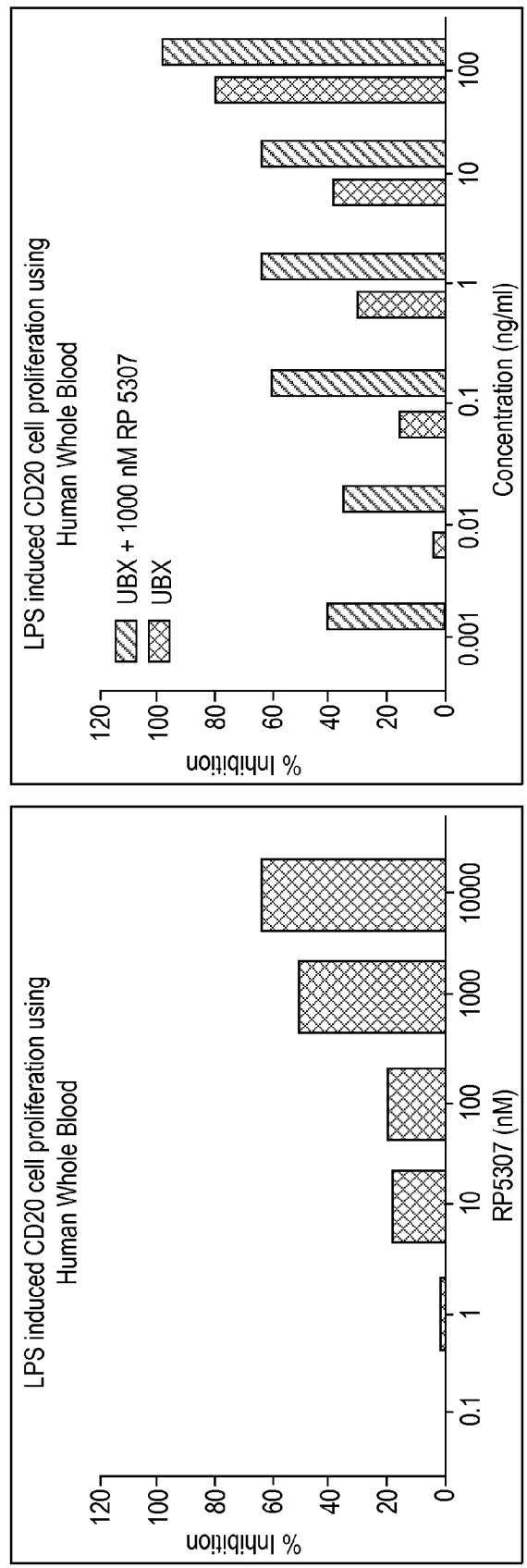

FIG. 3: Bar graphs showing the effect of S-isomer of a compound of formula A and Ublituximab on LPS-induced CD20-positive cell proliferation.

Figure 4:
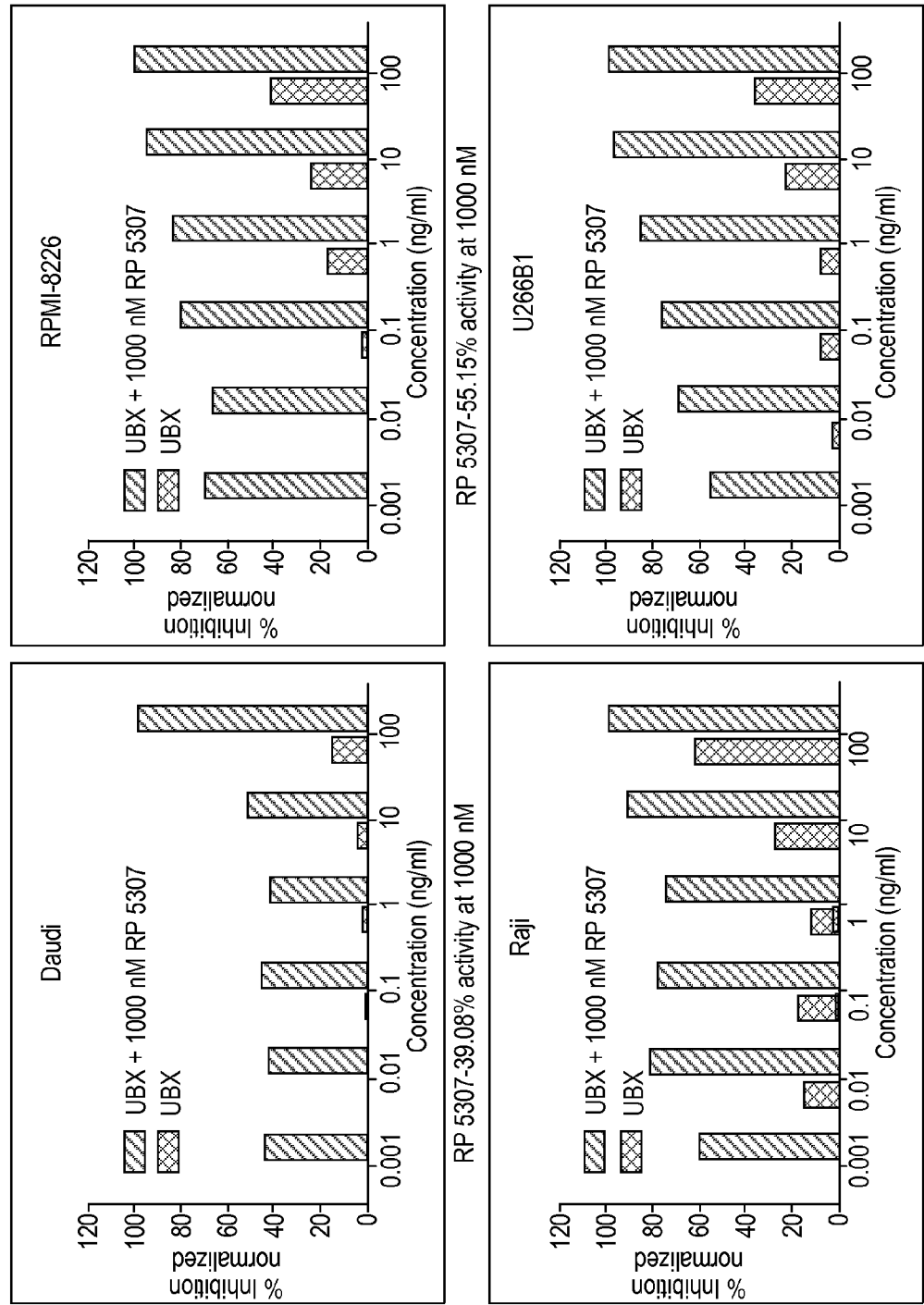

FIG. 4: Bar graphs showing the effect of S-isomer of a compound of formula A and Ublituximab on apoptosis in Daudi, RPMI-8226, Raji, and U266B1 cells.

Figure 5:
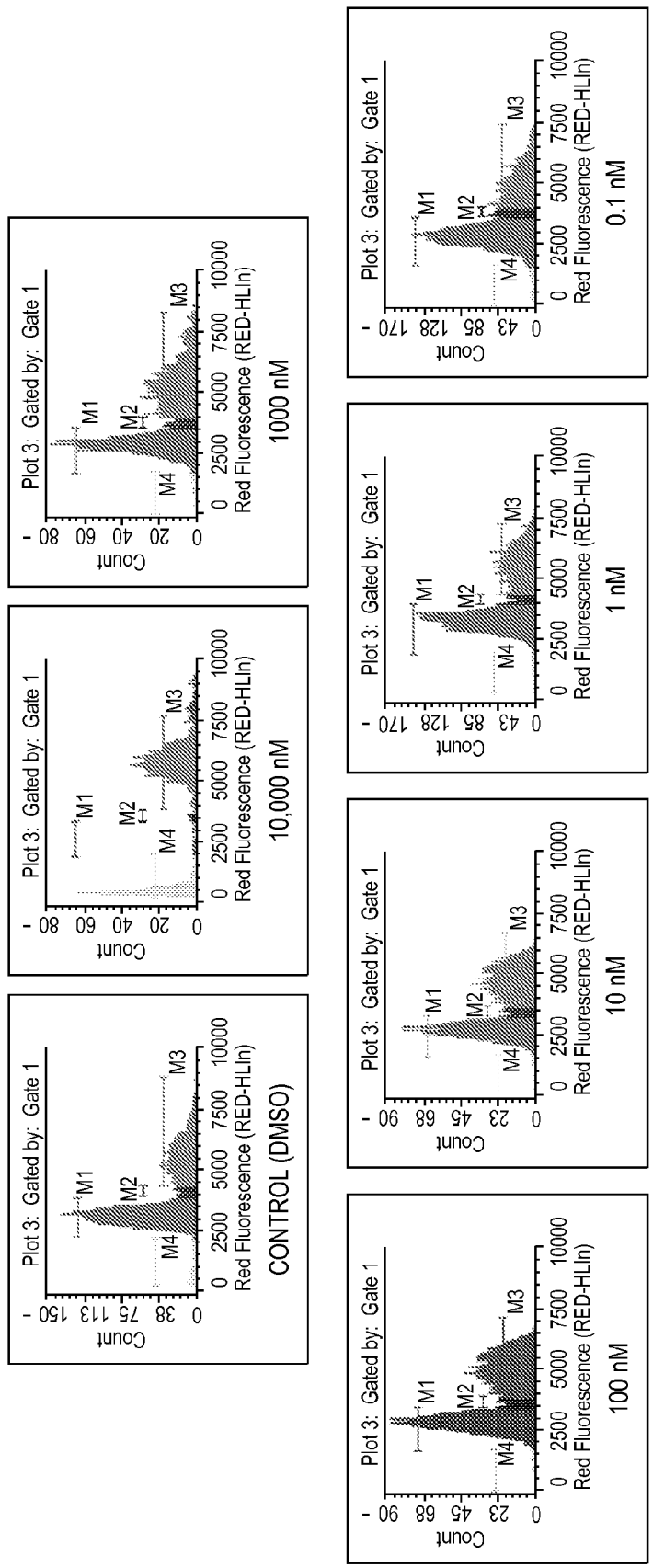

FIG. 5: Histograms showing the effect of S-isomer of a compound of formula A on cell cycle in U226B1 cells.

Figure 6:
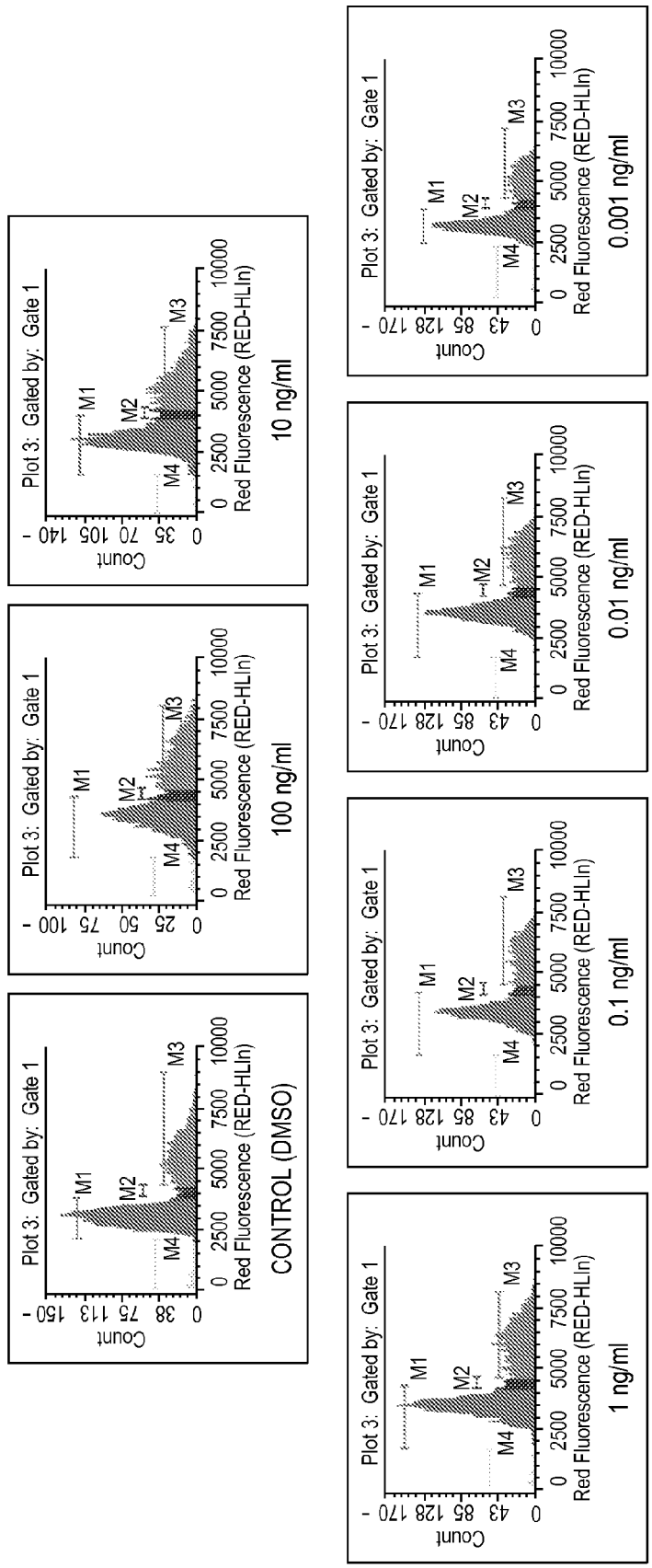

FIG. 6: Histograms showing the effect of the anti-CD20 antibody ublituximab on cell cycle in U226B1 cells.

Figure 7:
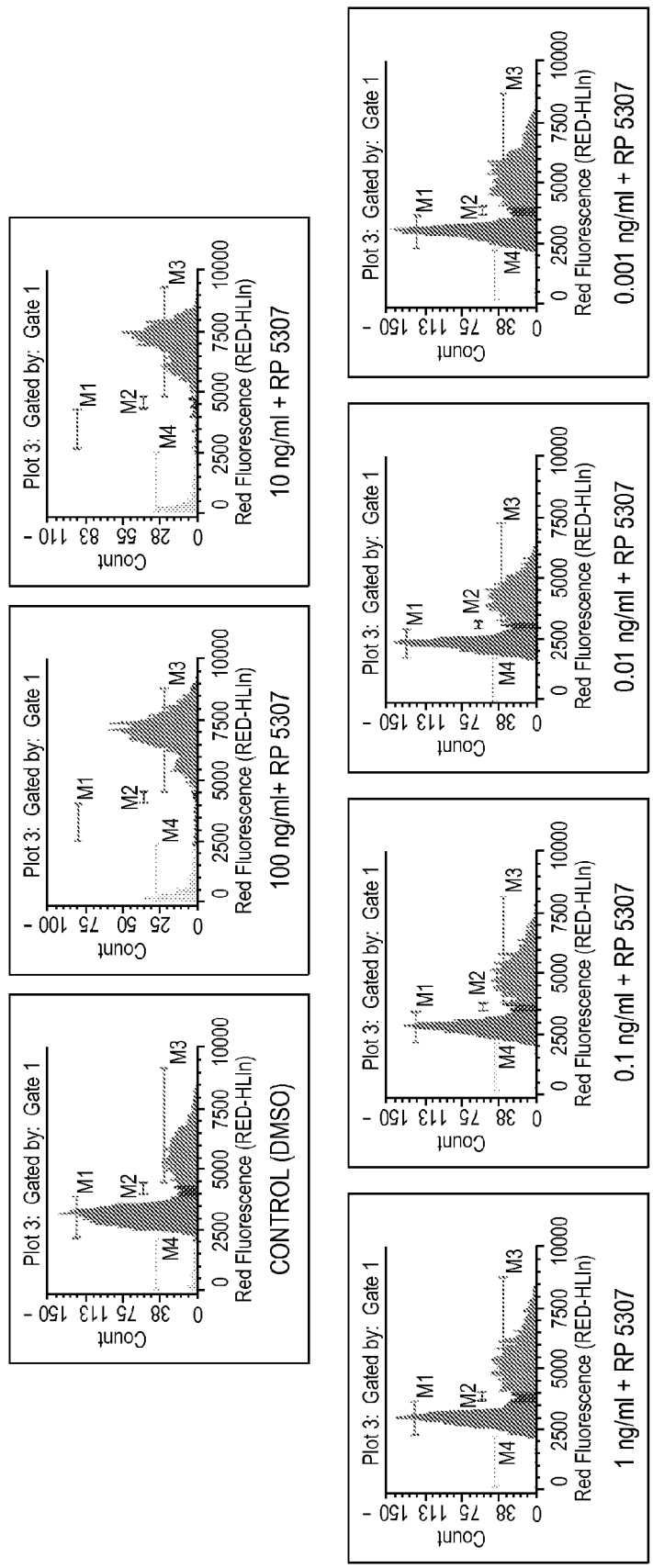

FIG. 7: Histograms showing the effect of S-isomer of a compound of formula A and the anti-CD20 antibody ublituximab on cell cycle in U226B1 cells.

Figure 8:
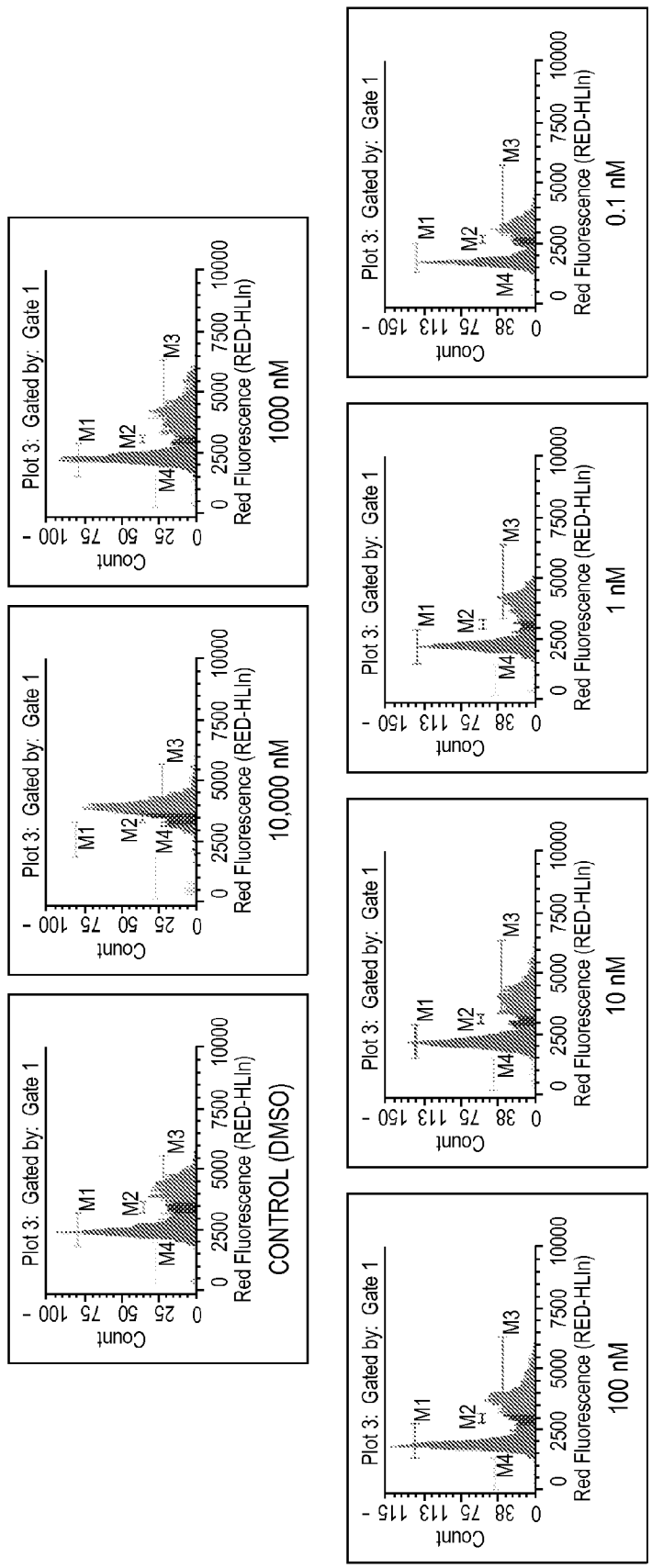

FIG. 8: Histograms showing the effect of S-isomer of a compound of formula A on cell cycle in Raji cells.

Figure 9:
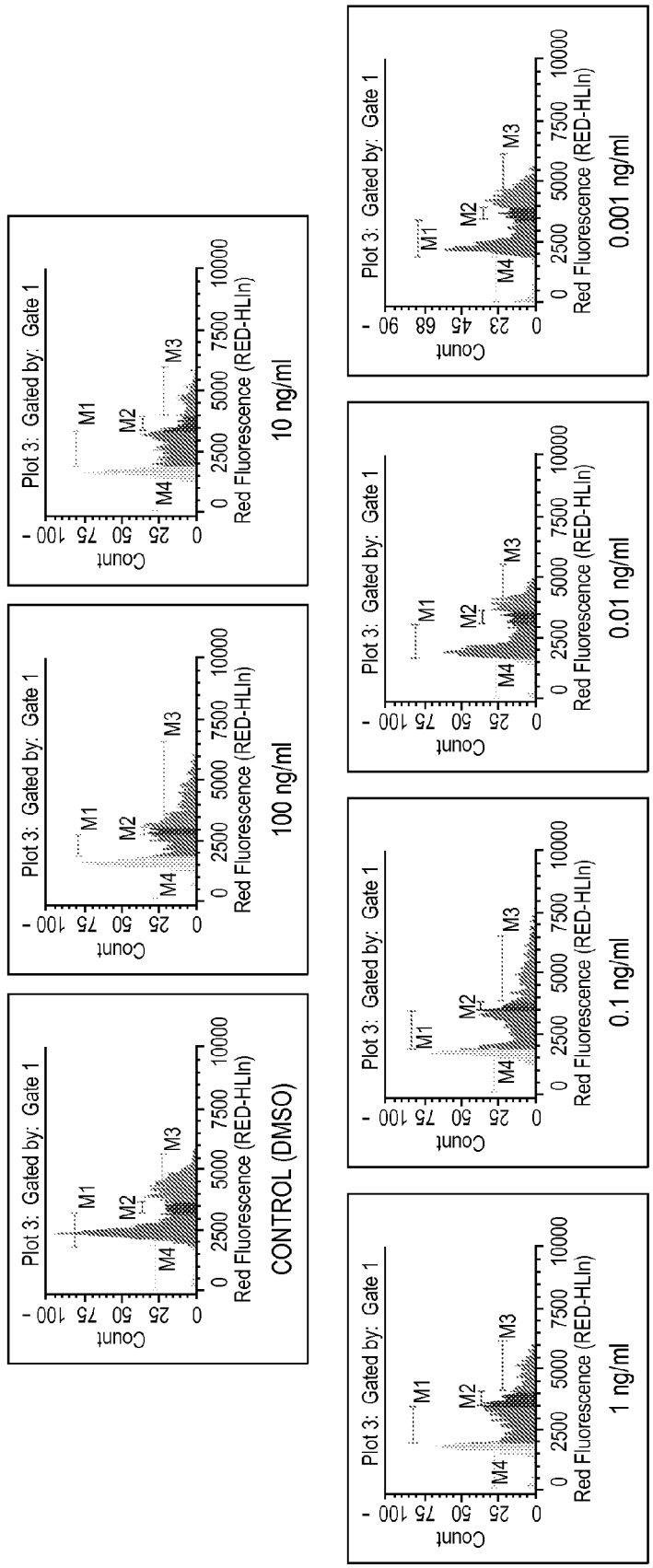

FIG. 9: Histograms showing the effect of the anti-CD20 antibody ublituximab on cell cycle in Raji cells.

Figure 10:
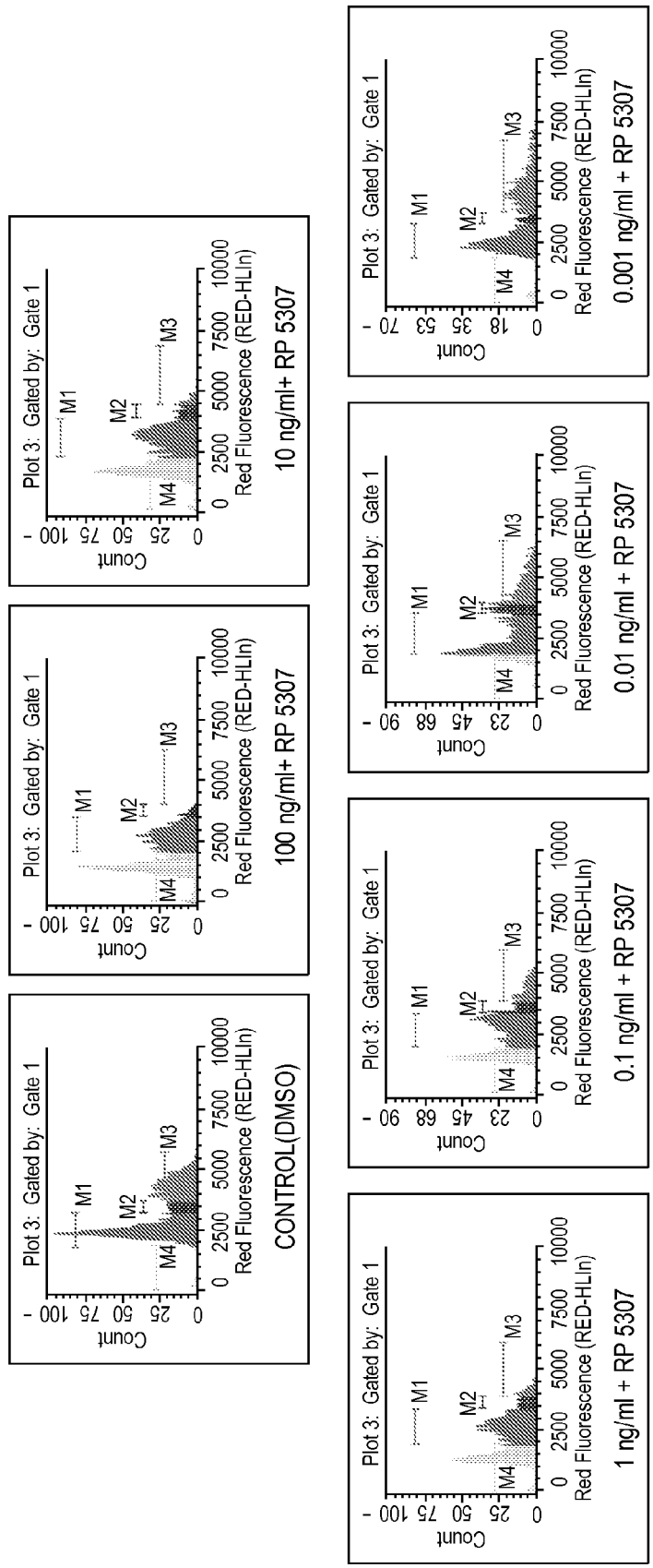

FIG. 10: Histograms showing the effect of S-isomer of a compound of formula A and the anti-CD20 antibody ublituximab on cell cycle in Raji cells.

Figure 11:
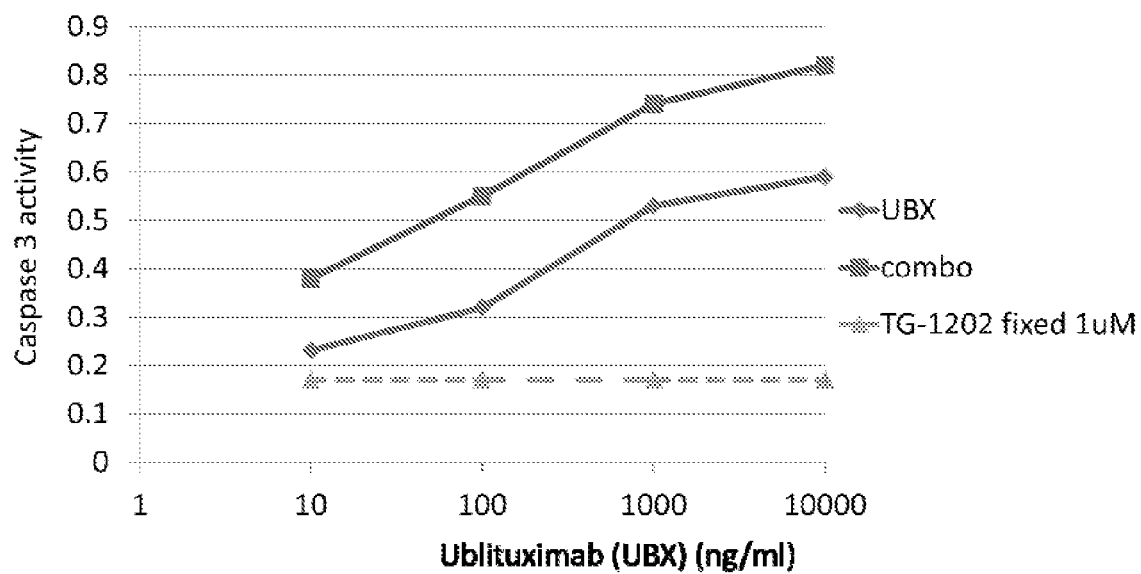

FIG. 11: Plots of caspase 3 activity showing the effect of S-isomer of a compound of formula A and Ublituximab on apoptosis in LY1 cells.

Figure 12:
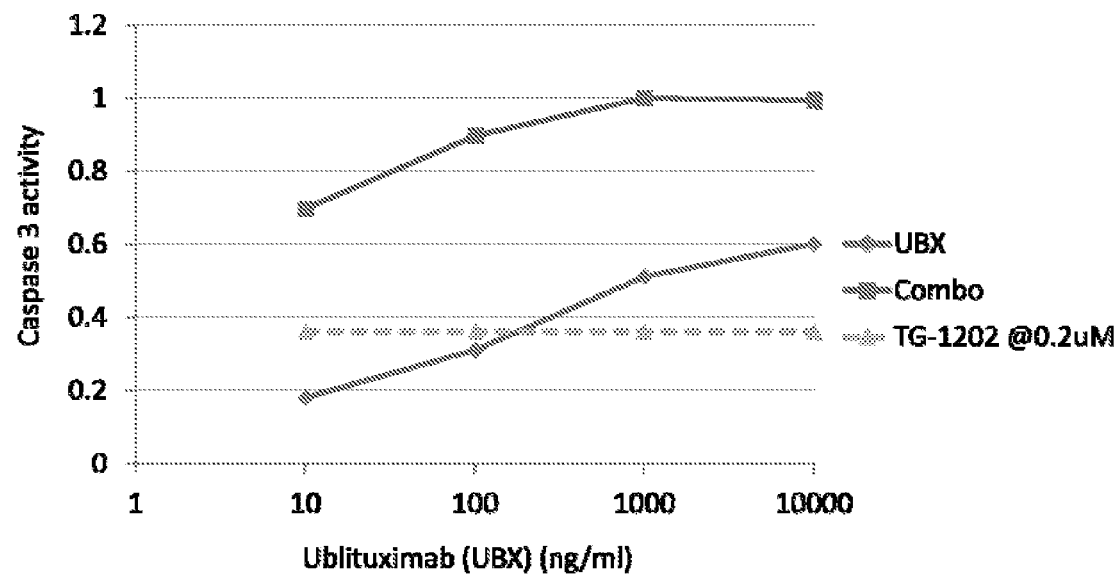

FIG. 12: Plots of caspase 3 activity showing the effect of S-isomer of a compound of formula A and Ublituximab on apoptosis in Raji cells.

DETAILED DESCRIPTION OF THE INVENTION

I. Definitions

To facilitate an understanding of the present invention, a number of terms and phrases are defined below.

The term "CD20" (also known as B lymphocyte CD20 antigen, MS4A1, B lymphocyte surface antigen B1, Bp35, Leukocyte surface antigen Leu-16) refers to any native CD20, unless otherwise indicated. The term "CD20" encompasses "full-length," unprocessed CD20 as well as any form of CD20 that results from processing within the cell. The term also encompasses naturally occurring variants of CD20, e.g., splice variants, allelic variants and isoforms. The CD20 polypeptides described herein can be isolated from a variety of sources, such as from human tissue types or from another source, or prepared by recombinant or synthetic methods. Examples of CD20 sequences include, but are not limited to NCBI reference numbers NP_068769.2 and NP_690605.1.

The term "antibody" means an immunoglobulin molecule that recognizes and specifically binds to a target, such as a protein, polypeptide, peptide, carbohydrate, polynucleotide, lipid, or combinations of the foregoing through at least one antigen recognition site within the variable region of the immunoglobulin molecule. As used herein, the term "antibody" encompasses intact polyclonal antibodies, intact monoclonal antibodies, antibody fragments (such as Fab, Fab', F(ab')2, and Fv fragments), single chain Fv (scFv) mutants, multispecific antibodies such as bispecific antibodies generated from at least two intact antibodies, chimeric antibodies, humanized antibodies, human antibodies, fusion proteins comprising an antigen determination portion of an antibody, and any other modified immunoglobulin molecule comprising an antigen recognition site so long as the antibodies exhibit the desired biological activity. An antibody can be of any of the five major classes of immunoglobulins: IgA, IgD, IgE, IgG, and IgM, or subclasses (isotypes) thereof (e.g., IgG1, IgG2, IgG3, IgG4, IgA1 and IgA2), based on the identity of their heavy-chain constant domains referred to as alpha, delta, epsilon, gamma, and mu, respectively. The different classes of immunoglobulins have different and well known subunit structures and three-dimensional configurations. Antibodies can be naked or conjugated to other molecules such as toxins, radioisotopes, proteins, etc.

A "blocking" antibody or an "antagonist" antibody is one which inhibits or reduces biological activity of the antigen it binds, such as CD20. In a certain embodiment, blocking antibodies or antagonist antibodies substantially or completely inhibit the biological activity of the antigen. Desirably, the biological activity is reduced by 10%, 20%, 30%, 50%, 70%, 80%, 90%, 95%, or even 100%.

The term "anti-CD20 antibody" or "an antibody that binds to CD20" refers to an antibody that is capable of binding CD20 with sufficient affinity such that the antibody is useful as a diagnostic and/or therapeutic agent in targeting CD20. The extent of binding of an anti-CD20 antibody to an unrelated, non-CD20 protein is less than about 10% of the binding of the antibody to CD20 as measured, e.g., by a radioimmunoassay (RIA). In certain embodiments, an antibody that binds to CD20 has a dissociation constant (Kd) of ≤1 µM, ≤100 nM, ≤10 nM, ≤1 nM, or ≤0.1 nM.

The term "antibody fragment" refers to a portion of an intact antibody and refers to the antigenic determining variable regions of an intact antibody. Examples of antibody fragments include, but are not limited to, Fab, Fab', F(ab')2, and Fv fragments, linear antibodies, single chain antibodies, and multispecific antibodies formed from antibody fragments.

A "monoclonal antibody" refers to a homogeneous antibody population involved in the highly specific recognition and binding of a single antigenic determinant, or epitope. This is in contrast to polyclonal antibodies that typically include different antibodies directed against different antigenic determinants. The term "monoclonal antibody" encompasses both intact and full-length monoclonal antibodies as well as antibody fragments (such as Fab, Fab', F(ab')2, Fv), single chain (scFv) mutants, fusion proteins comprising an antibody portion, and any other modified immunoglobulin molecule comprising an antigen recognition site. Furthermore, "monoclonal antibody" refers to such antibodies made in any number of manners including but not limited to by hybridoma, phage selection, recombinant expression, and transgenic animals.

The term "humanized antibody" refers to forms of non-human (e.g., murine) antibodies that are specific immunoglobulin chains, chimeric immunoglobulins, or fragments thereof that contain minimal non-human (e.g., murine) sequences. Typically, humanized antibodies are human immunoglobulins in which residues from the complementary determining region (CDR) are replaced by residues from the CDR of a non-human species (e.g., mouse, rat, rabbit, hamster) that have the desired specificity, affinity, and capability (Jones et al., Nature, 321:522-525 (1986); Riechmann et al., Nature, 332:323-327 (1988); Verhoeyen et al., Science, 239:1534-1536 (1988)). In some instances, the Fv framework region (FR) residues of a human immunoglobulin are replaced with the corresponding residues in an antibody from a non-human species that has the desired specificity, affinity, and capability. The humanized antibody can be further modified by the substitution of additional residues either in the Fv framework region and/or within the replaced non-human residues to refine and optimize antibody specificity, affinity, and/or capability. In general, the humanized antibody will comprise substantially all of at least one, and typically two or three, variable domains containing all or substantially all of the CDR regions that correspond to the non-human immunoglobulin whereas all or substantially all of the FR regions are those of a human immunoglobulin consensus sequence. The humanized antibody can also comprise at least a portion of an immunoglobulin constant region or domain (Fc), typically that of a human immunoglobulin. Examples of methods used to generate humanized antibodies are described in U.S. Pat. No. 5,225,539 or 5,639,641.

A "variable region" of an antibody refers to the variable region of the antibody light chain or the variable region of the antibody heavy chain, either alone or in combination. The variable regions of the heavy and light chain each consist of four framework regions (FR) connected by three complementarity determining regions (CDRs) also known as hypervariable regions. The CDRs in each chain are held together in close proximity by the FRs and, with the CDRs from the other chain, contribute to the formation of the antigen-binding site of antibodies. There are at least two techniques for determining CDRs: (1) an approach based on cross-species sequence variability (i.e., Kabat et al., Sequences of Proteins of Immunological Interest, (5th ed., 1991, National Institutes of Health, Bethesda Md.)); and (2) an approach based on crystallographic studies of antigen-antibody complexes (Al-lazikani et at J. Molec. Biol. 273: 927-948 (1997)). In addition, combinations of these two approaches are sometimes used in the art to determine CDRs.

The Kabat numbering system is generally used when referring to a residue in the variable domain (approximately residues 1-107 of the light chain and residues 1-113 of the heavy chain) (e.g., Kabat et al., Sequences of Immunological Interest. 5th Ed. Public Health Service, National Institutes of Health, Bethesda, Md. (1991)).

The amino acid position numbering as in Kabat, refers to the numbering system used for heavy chain variable domains or light chain variable domains of the compilation of antibodies in Kabat et al., Sequences of Proteins of Immunological Interest, 5th Ed. Public Health Service, National Institutes of Health, Bethesda, Md. (1991). Using this numbering system, the actual linear amino acid sequence can contain fewer or additional amino acids corresponding to a shortening of, or insertion into, a FR or CDR of the variable domain. For example, a heavy chain variable domain can include a single amino acid insert (residue 52a according to Kabat) after residue 52 of H2 and inserted residues (e.g., residues 82a, 82b, and 82c, etc. according to Kabat) after heavy chain FR residue 82. The Kabat numbering of residues can be determined for a given antibody by alignment at regions of homology of the sequence of the antibody with a "standard" Kabat numbered sequence. Chothia refers instead to the location of the structural loops (Chothia and Lesk J. Mol. Biol. 196:901-917 (1987)). The end of the Chothia CDR-H1 loop when numbered using the Kabat numbering convention varies between H32 and H34 depending on the length of the loop (this is because the Kabat numbering scheme places the insertions at H35A and H35B; if neither 35A nor 35B is present, the loop ends at 32; if only 35A is present, the loop ends at 33; if both 35A and 35B are present, the loop ends at 34). The AbM hypervariable regions represent a compromise between the Kabat CDRs and Chothia structural loops, and are used by Oxford Molecular's AbM antibody modeling software.

| Loop | Kabat | AbM | Chothia |
|---|---|---|---|
| L1 | L24-L34 | L24-L34 | L24-L34 |
| L2 | L50-L56 | L50-L56 | L50-L56 |
| L3 | L89-L97 | L89-L97 | L89-L97 |
| H1 | H31-H35B | H26-H35B | H26-H32 . . . 34 |
| | | (Kabat Numbering) | |
| H1 | H31-H35 | H26-H35 | H26-H32 |
| | | (Chothia Numbering) | |
| H2 | H50-H65 | H50-H58 | H52-H56 |
| H3 | H95-H102 | H95-H102 | H95-H102 |

The term "human antibody" means an antibody produced by a human or an antibody having an amino acid sequence corresponding to an antibody produced by a human made using any technique known in the art. This definition of a human antibody includes intact or full-length antibodies, fragments thereof, and/or antibodies comprising at least one human heavy and/or light chain polypeptide such as, for example, an antibody comprising murine light chain and human heavy chain polypeptides.

The term "chimeric antibodies" refers to antibodies wherein the amino acid sequence of the immunoglobulin molecule is derived from two or more species. Typically, the variable region of both light and heavy chains corresponds to the variable region of antibodies derived from one species of mammals (e.g., mouse, rat, rabbit, etc) with the desired specificity, affinity, and capability while the constant regions are homologous to the sequences in antibodies derived from another (usually human) to avoid eliciting an immune response in that species.

The term "epitope" or "antigenic determinant" are used interchangeably herein and refer to that portion of an antigen capable of being recognized and specifically bound by a particular antibody. When the antigen is a polypeptide, epitopes can be formed both from contiguous amino acids and noncontiguous amino acids juxtaposed by tertiary folding of a protein. Epitopes formed from contiguous amino acids are typically retained upon protein denaturing, whereas epitopes formed by tertiary folding are typically lost upon protein denaturing. An epitope typically includes at least 3, and more usually, at least 5 or 8-10 amino acids in a unique spatial conformation.

"Binding affinity" generally refers to the strength of the sum total of noncovalent interactions between a single binding site of a molecule (e.g., an antibody) and its binding partner (e.g., an antigen). Unless indicated otherwise, as used herein, "binding affinity" refers to intrinsic binding affinity which reflects a 1:1 interaction between members of a binding pair (e.g., antibody and antigen). The affinity of a molecule X for its partner Y can generally be represented by the dissociation constant (Kd). Affinity can be measured by common methods known in the art, including those described herein. Low-affinity antibodies generally bind antigen slowly and tend to dissociate readily, whereas high-affinity antibodies generally bind antigen faster and tend to remain bound longer. A variety of methods of measuring binding affinity are known in the art, any of which can be used for purposes of the present invention. Specific illustrative embodiments are described herein.

"Or better" when used herein to refer to binding affinity refers to a stronger binding between a molecule and its binding partner. "Or better" when used herein refers to a stronger binding, represented by a smaller numerical Kd value. For example, an antibody which has an affinity for an antigen of "0.6 nM or better," the antibody's affinity for the antigen is <0.6 nM, i.e., 0.59 nM, 0.58 nM, 0.57 nM etc. or any value less than 0.6 nM.

The phrase "substantially similar," or "substantially the same," as used herein, denotes a sufficiently high degree of similarity between two numeric values (generally one associated with an antibody of the invention and the other associated with a reference/comparator antibody) such that one of skill in the art would consider the difference between the two values to be of little or no biological and/or statistical significance within the context of the biological characteristics measured by said values (e.g., Kd values). The difference between said two values is less than about 50%, less than about 40%, less than about 30%, less than about 20%, or less than about 10% as a function of the value for the reference/comparator antibody.

A polypeptide, antibody, polynucleotide, vector, cell, or composition which is "isolated" is a polypeptide, antibody, polynucleotide, vector, cell, or composition which is in a form not found in nature. Isolated polypeptides, antibodies, polynucleotides, vectors, cells or compositions include those which have been purified to a degree that they are no longer in a form in which they are found in nature. In some embodiments, an antibody, polynucleotide, vector, cell, or composition which is isolated is substantially pure.

As used herein, "substantially pure" refers to material which is at least 50% pure (i.e., free from contaminants), at least 90% pure, at least 95% pure, at least 98% pure, or at least 99% pure.

The terms "cancer" and "cancerous" refer to or describe the physiological condition in mammals in which a population of cells are characterized by unregulated cell growth. Examples of cancer include, but are not limited to, carcinoma, lymphoma, blastoma, sarcoma, and leukemia. More particular examples of such cancers include squamous cell cancer, small-cell lung cancer, non-small cell lung cancer, adenocarcinoma of the lung, squamous carcinoma of the lung, cancer of the peritoneum, hepatocellular cancer, gastrointestinal cancer, pancreatic cancer, glioblastoma, cervical cancer, ovarian cancer, liver cancer, bladder cancer, hepatoma, breast cancer, colon cancer, colorectal cancer, endometrial or uterine carcinoma, salivary gland carcinoma, kidney cancer, liver cancer, prostate cancer, vulval cancer, thyroid cancer, hepatic carcinoma and various types of head and neck cancers.

"Tumor" and "neoplasm" refer to any mass of tissue that result from excessive cell growth or proliferation, either benign (noncancerous) or malignant (cancerous) including pre-cancerous lesions.

The terms "cancer cell," "tumor cell," and grammatical equivalents refer to the total population of cells derived from a tumor or a pre-cancerous lesion, including both non-tumorigenic cells, which comprise the bulk of the tumor cell population, and tumorigenic stem cells (cancer stem cells). As used herein, the term "tumor cell" will be modified by the term "non-tumorigenic" when referring solely to those tumor cells lacking the capacity to renew and differentiate to distinguish those tumor cells from cancer stem cells.

The term "subject" refers to any animal (e.g., a mammal), including, but not limited to humans, non-human primates, rodents, and the like, which is to be the recipient of a particular treatment. Typically, the terms "subject" and "patient" are used interchangeably herein in reference to a human subject.

A cell "population" can refer to a single cell or to multiple cells. The cell or cells can be cells in culture or cells in an organism. For example, a cell population can be in a subject or patient.

The term "pharmaceutical formulation" refers to a preparation which is in such form as to permit the biological activity of the active ingredient to be effective, and which contains no additional components which are unacceptably toxic to a subject to which the formulation would be administered. Such formulation can be sterile.

An "effective amount" of an antibody as disclosed herein is an amount sufficient to carry out a specifically stated purpose. An "effective amount" can be determined empirically and in a routine manner, in relation to the stated purpose.

The term "therapeutically effective amount" refers to an amount of an antibody or other drug effective to "treat" a disease or disorder in a subject or mammal. In the case of cancer, the therapeutically effective amount of the drug can reduce the number of cancer cells; reduce the tumor size; inhibit (i.e., slow to some extent and in a certain embodiment, stop) cancer cell infiltration into peripheral organs; inhibit (i.e., slow to some extent and in a certain embodiment, stop) tumor metastasis; inhibit, to some extent, tumor growth; and/or relieve to some extent one or more of the symptoms associated with the cancer. See the definition herein of "treating." To the extent the drug can prevent growth and/or kill existing cancer cells, it can be cytostatic and/or cytotoxic. A "prophylactically effective amount" refers to an amount effective, at dosages and for periods of time necessary, to achieve the desired prophylactic result. Typically but not necessarily, since a prophylactic dose is used in subjects prior to or at an earlier stage of disease, the prophylactically effective amount will be less than the therapeutically effective amount.

Terms such as "treating" or "treatment" or "to treat" or "alleviating" or "to alleviate" refer to both 1) therapeutic measures that cure, slow down, lessen symptoms of, and/or halt progression of a diagnosed pathologic condition or disorder and 2) prophylactic or preventative measures that prevent and/or slow the development of a targeted pathologic condition or disorder. Thus, those in need of treatment include those already with the disorder; those prone to have the disorder; and those in whom the disorder is to be prevented. In certain embodiments, a subject is successfully "treated" for cancer according to the methods of the present invention if the patient shows one or more of the following: reduction in cachexia, increase in survival time, elongation in time to tumor progression, reduction in tumor mass, reduction in tumor burden and/or a prolongation in time to tumor metastasis, time to tumor recurrence, tumor response, complete response, partial response, stable disease, progressive disease, progression free survival (PFS), overall survival (OS), each as measured by standards set by the National Cancer Institute and the U.S. Food and Drug Administration for the approval of new drugs. See Johnson et al, *J. Clin. Oncol.* 21(7):1404-1411 (2003).

A "combination" of an anti-CD20 antibody and a PI3Kδ selective inhibitor refers to an anti-CD20 antibody or fragment thereof and Compound A as defined herein that are intended to be administered to the same population of cells or to the same subject simultaneously, sequentially, or both simultaneously and sequentially. Thus, by way of example, administration of an anti-CD20 antibody or fragment thereof preceeding or following (e.g., by an hour, day, week, or month) administration of Compound A constitutes administration of a combination of an anti-CD20 antibody or fragment thereof and Compound A. In addition, simultaneous administration of an anti-CD20 antibody or fragment thereof and Compound A also constitutes administration of a combination of the anti-CD20 antibody or fragment thereof and Compound A, regardless of whether the anti-CD20 antibody or fragment thereof and Compound A are administered together in a single pharmaceutical formulation or are administered simultaneously in separate pharmaceutical formulations by either the same or different routes of administration.

A tumor which "does not respond," "responds poorly," or is "refractory" to treatment with an anti-CD20 antibody does not show statistically significant improvement in response to an anti-CD20 antibody treatment when compared to no treatment or treatment with placebo in a recognized animal model or human clinical trial, or which responds to an initial treatment with anti-CD20 antibodies but grows as treatment continues.

The ability of a tumor or cell type to respond to an anti-CD20 antibody can be tested using laboratory cell lines such as Raji or Wil2-S, or patient donor cell lines. In addition, activity can be measured using B-cell depletion assays, e.g., in whole blood from patients.

"Polynucleotide" or "nucleic acid," as used interchangeably herein, refer to polymers of nucleotides of any length, and include DNA and RNA. The nucleotides can be deoxyribonucleotides, ribonucleotides, modified nucleotides or bases, and/or their analogs, or any substrate that can be incorporated into a polymer by DNA or RNA polymerase. A polynucleotide can comprise modified nucleotides, such as methylated nucleotides and their analogs. If present, modification to the nucleotide structure can be imparted before or after assembly of the polymer. The sequence of nucleotides can be interrupted by non-nucleotide components. A polynucleotide can be further modified after polymerization, such as by conjugation with a labeling component. Other types of modifications include, for example, "caps," substitution of one or more of the naturally occurring nucleotides with an analog, internucleotide modifications such as, for example, those with uncharged linkages (e.g., methyl phosphonates, phosphotriesters, phosphoamidates, cabamates, etc.) and with charged linkages (e.g., phosphorothioates, phosphorodithioates, etc.), those containing pendant moieties, such as, for example, proteins (e.g., nucleases, toxins, antibodies, signal peptides, ply-L-lysine, etc.), those with intercalators (e.g., acridine, psoralen, etc.), those containing chelators (e.g., metals, radioactive metals, boron, oxidative metals, etc.), those containing alkylators, those with modified linkages (e.g., alpha anomeric nucleic acids, etc.), as well as unmodified forms of the polynucleotide(s). Further, any of the hydroxyl groups ordinarily present in the sugars can be replaced, for example, by phosphonate groups, phosphate groups, protected by standard protecting groups, or activated to prepare additional linkages to additional nucleotides, or can be conjugated to solid supports. The 5' and 3' terminal OH can be phosphorylated or substituted with amines or organic capping group moieties of from 1 to 20 carbon atoms. Other hydroxyls can also be derivatized to standard protecting groups. Polynucleotides can also contain analogous forms of ribose or deoxyribose sugars that are generally known in the art, including, for example, 2'-O-methyl-, 2'-O-allyl, 2'-fluoro- or 2'-azido-ribose, carbocyclic sugar analogs, alpha-anomeric sugars, epimeric sugars such as arabinose, xyloses or lyxoses, pyranose sugars, furanose sugars, sedoheptuloses, acyclic analogs and abasic nucleoside analogs such as methyl riboside. One or more phosphodiester linkages can be replaced by alternative linking groups. These alternative linking groups include, but are not limited to, embodiments wherein phosphate is replaced by P(O)S ("thioate"), P(S)S ("dithioate"), (O)NR$_2$ ("amidate"), P(O)R, P(O)OR', CO or CH$_2$ ("formacetal"), in which each R or R' is independently H or substituted or unsubstituted alkyl (1-20 C) optionally containing an ether (—O—) linkage, aryl, alkenyl, cycloalkyl, cycloalkenyl or araldyl. Not all linkages in a polynucleotide need be identical. The preceding description applies to all polynucleotides referred to herein, including RNA and DNA.

The term "vector" means a construct, which is capable of delivering, and expressing, one or more gene(s) or sequence(s) of interest in a host cell. Examples of vectors include, but are not limited to, viral vectors, naked DNA or RNA expression vectors, plasmid, cosmid or phage vectors, DNA or RNA expression vectors associated with cationic condensing agents, DNA or RNA expression vectors encapsulated in liposomes, and certain eukaryotic cells, such as producer cells.

The terms "polypeptide," "peptide," and "protein" are used interchangeably herein to refer to polymers of amino acids of any length. The polymer can be linear or branched, it can comprise modified amino acids, and it can be interrupted by non-amino acids. The terms also encompass an amino acid polymer that has been modified naturally or by intervention; for example, disulfide bond formation, glycosylation, lipidation, acetylation, phosphorylation, or any other manipulation or modification, such as conjugation with a labeling component. Also included within the definition are, for example, polypeptides containing one or more analogs of an amino acid (including, for example, unnatural amino acids, etc.), as well as other modifications known in the art. It is understood that, because the polypeptides of this invention are based upon antibodies, in certain embodiments, the polypeptides can occur as single chains or associated chains.

The terms "identical" or percent "identity" in the context of two or more nucleic acids or polypeptides, refer to two or more sequences or subsequences that are the same or have a specified percentage of nucleotides or amino acid residues that are the same, when compared and aligned (introducing gaps, if necessary) for maximum correspondence, not considering any conservative amino acid substitutions as part of the sequence identity. The percent identity can be measured using sequence comparison software or algorithms or by visual inspection. Various algorithms and software are known in the art that can be used to obtain alignments of amino acid or nucleotide sequences. One such non-limiting example of a sequence alignment algorithm is the algorithm described in Karlin et al, *Proc. Natl. Acad. Sci.*, 87:2264-2268 (1990), as modified in Karlin et al., *Proc. Natl. Acad. Sci.*, 90:5873-5877 (1993), and incorporated into the NBLAST and XBLAST programs (Altschul et al., *Nucleic Acids Res.*, 25:3389-3402 (1991)). In certain embodiments, Gapped BLAST can be used as described in Altschul et al., *Nucleic Acids Res.*, 25:3389-3402 (1997). BLAST-2, WU-BLAST-2 (Altschul et al., *Methods in Enzymology*, 266:460-480 (1996)), ALIGN, ALIGN-2 (Genentech, South San Francisco, Calif.) or Megalign (DNASTAR) are additional publicly available software programs that can be used to align sequences. In certain embodiments, the percent identity between two nucleotide sequences is determined using the GAP program in GCG software (e.g., using a NWSgapdna.CMP matrix and a gap weight of 40, 50, 60, 70, or 90 and a length weight of 1, 2, 3, 4, 5, or 6). In certain alternative embodiments, the GAP program in the GCG software package, which incorporates the algorithm of Needleman and Wunsch (J. Mol. Biol. (48):444-453 (1970)) can be used to determine the percent identity between two amino acid sequences (e.g., using either a Blossum 62 matrix or a PAM250 matrix, and a gap weight of 16, 14, 12, 10, 8, 6, or 4 and a length weight of 1, 2, 3, 4, 5). Alternatively, in certain embodiments, the percent identity between nucleotide or amino acid sequences is determined using the algorithm of Myers and Miller (CABIOS, 4:11-17 (1989)). For example, the percent identity can be determined using the ALIGN program (version 2.0) and using a PAM120 with residue table, a gap length penalty of 12 and a gap penalty of 4. Appropriate parameters for maximal alignment by particular alignment software can be determined by one skilled in the art. In certain embodiments, the default parameters of the alignment software are used. In certain embodiments, the percentage identity "X" of a first amino acid sequence to a second sequence amino acid is calculated as 100×(Y/Z), where Y is the number of amino acid residues scored as identical matches in the alignment of the first and second sequences (as aligned by visual inspection or a particular sequence alignment program) and Z is the total number of residues in the second sequence. If the length of a first sequence is longer than the second sequence, the percent identity of the first sequence to the second sequence will be longer than the percent identity of the second sequence to the first sequence.

As a non-limiting example, whether any particular polynucleotide has a certain percentage sequence identity (e.g., is at least 80% identical, at least 85% identical, at least 90% identical, and in some embodiments, at least 95%, 96%, 97%, 98%, or 99% identical) to a reference sequence can, in certain embodiments, be determined using the Bestfit program (Wisconsin Sequence Analysis Package, Version 8 for Unix, Genetics Computer Group, University Research Park, 575 Science Drive, Madison, Wis. 53711). Bestfit uses the local homology algorithm of Smith and Waterman, Advances in Applied Mathematics 2: 482 489 (1981), to find the best segment of homology between two sequences. When using Bestfit or any other sequence alignment program to determine whether a particular sequence is, for instance, 95% identical to a reference sequence according to the present invention, the parameters are set such that the percentage of identity is calculated over the full length of the reference nucleotide sequence and that gaps in homology of up to 5% of the total number of nucleotides in the reference sequence are allowed.

In some embodiments, two nucleic acids or polypeptides of the invention are substantially identical, meaning they have at least 70%, at least 75%, at least 80%, at least 85%, at least 90%, and in some embodiments at least 95%, 96%, 97%, 98%, 99% nucleotide or amino acid residue identity, when compared and aligned for maximum correspondence, as measured using a sequence comparison algorithm or by visual inspection. In certain embodiments, identity exists over a region of the sequences that is at least about 10, about 20, about 40-60 residues in length or any integral value therebetween, or over a longer region than 60-80 residues, at least about 90-100 residues, or the sequences are substantially identical over the full length of the sequences being compared, such as the coding region of a nucleotide sequence for example.

A "conservative amino acid substitution" is one in which one amino acid residue is replaced with another amino acid residue having a similar side chain. Families of amino acid residues having similar side chains have been defined in the art, including basic side chains (e.g., lysine, arginine, histidine), acidic side chains (e.g., aspartic acid, glutamic acid), uncharged polar side chains (e.g., asparagine, glutamine, serine, threonine, tyrosine, cysteine), nonpolar side chains (e.g., glycine, alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). For example, substitution of a phenylalanine for a tyrosine is a conservative substitution. In certain embodiments, conservative substitutions in the sequences of the polypeptides and antibodies of the invention do not abrogate the binding of the polypeptide or antibody containing the amino acid sequence, to the antigen(s), i.e., the FOLR1 to which the polypeptide or antibody binds. Methods of identifying nucleotide and amino acid conservative substitutions which do not eliminate antigen binding are well-known in the art (see, e.g., Brummell et al., *Biochem.* 32: 1180-1 187 (1993); Kobayashi et al. *Protein Eng.* 12(10):879-884 (1999); and Burks et al. *Proc. Natl. Acad. Sci. USA* 94:412-417 (1997)).

All numbers in this disclosure indicating amounts, ratios of materials, physical properties of materials, and/or use are to be understood as modified by the word "about," except as otherwise explicitly indicated. The term "about" when referring to a number or a numerical range means that the number or numerical range referred to is an approximation within experimental variability (or within statistical experimental error), and thus the number or numerical range can vary from, for example, between 1% and 15% of the stated number or numerical range.

The compound of the invention can contain one or more asymmetric centers (chiral centers) and can thus give rise to enantiomers, diastereomers, and other stereoisomeric forms that can be defined, in terms of absolute stereochemistry, as (R)— or (S)—. The present disclosure is meant to encompass all such possible forms, as well as their racemic and resolved forms and mixtures thereof. The individual enantiomers can be separated according to methods known in the art in view of the present disclosure.

As used herein, the term "stereoisomers" is a general term for all isomers of individual molecules that differ only in the orientation of their atoms in space. It includes enantiomers and isomers of compounds with more than one chiral center that are not mirror images of one another (diastereomers).

The term "chiral center" refers to a carbon atom to which four different groups are attached.

The terms "enantiomer" and "enantiomeric" refer to a molecule that cannot be superimposed on its mirror image and hence is optically active wherein the enantiomer rotates the plane of polarized light in one direction and its mirror image compound rotates the plane of polarized light in the opposite direction.

The term "racemic" refers to a mixture of equal parts of enantiomers and which mixture is optically inactive.

The term "resolution" refers to the separation, concentration or depletion of one of the two enantiomeric forms of a molecule.

The present disclosure encompasses solvates of compounds of the invention. Solvates typically do not significantly alter the physiological activity or toxicity of the compounds, and as such may function as pharmacological equivalents. The term "solvate" as used herein is a combination, physical association and/or solvation of a compound of the present disclosure with a solvent molecule, e.g. a disolvate, monosolvate or hemisolvate, where the ratio of solvent molecule to compound of the present disclosure is about 2:1, about 1:1 or about 1:2, respectively. This physical association involves varying degrees of ionic and covalent bonding, including hydrogen bonding. In certain instances, the solvate can be isolated, such as when one or more solvent molecules are incorporated into the crystal lattice of a crystalline solid. Thus, "solvate" encompasses both solution-phase and isolatable solvates. Compounds of the invention can be present as solvated forms with a pharmaceutically acceptable solvent, such as water, methanol, ethanol, and the like, and it is intended that the disclosure includes both solvated and unsolvated forms of compounds of the invention. One type of solvate is a hydrate. A "hydrate" relates to a particular subgroup of solvates where the solvent molecule is water. Solvates typically can function as pharmacological equivalents. Preparation of solvates is known in the art. See, e.g., M. Caira et al., *J. Pharmaceut. Sci.*, 93(3):601-611 (2004); E. C. van Tonder et al., *AAPS Pharm. Sci. Tech.* 5(1): Article 12 (2004); and A. L. Bingham et al., *Chem. Commun.* 603-604 (2001). A typical, non-limiting, process of preparing a solvate would involve dissolving a compound of the invention in a desired solvent (organic, water, or a mixture thereof) at temperatures about 20° C. to about 25° C., then cooling the solution at a rate sufficient to form crystals, and isolating the crystals by known methods, e.g., filtration. Analytical techniques such as infrared spectroscopy can be used to confirm the presence of the solvent in a crystal of the solvate.

The term "prodrug" refers to a compound, which is an inactive precursor of a compound, converted into its active form in the body by normal metabolic processes. Prodrug design is discussed generally in Hardma, et al. (Eds.), *Goodman and Gilman's The Pharmacological Basis of Therapeutics*, 9th ed., pp. 11-16 (1996). A thorough discussion is provided in Higuchi, et al., *Prodrugs as Novel Delivery Systems*, Vol. 14, ASCD Symposium Series, and in Roche (ed.), *Bioreversible Carriers in Drug Design*, American Pharmaceutical Association and Pergamon Press (1987). To illustrate, prodrugs can be converted into a pharmacologically active form through hydrolysis of, for example, an ester or amide linkage, thereby introducing or exposing a functional group on the resultant product. The prodrugs can be designed to react with an endogenous compound to form a water-soluble conjugate that further enhances the pharmacological properties of the compound, for example, increased circulatory half-life. Alternatively, prodrugs can be designed to undergo covalent modification on a functional group with, for example, glucuronic acid, sulfate, glutathione, amino acids, or acetate. The resulting conjugate can be inactivated and excreted in the urine, or rendered more potent than the parent compound. High molecular weight conjugates also can be excreted into the bile, subjected to enzymatic cleavage, and released back into the circulation, thereby effectively increasing the biological half-life of the originally administered compound. Prodrugs of the compounds of the invention are intended to be covered within the scope of this invention.

The instant invention also includes the compounds which differ only in the presence of one or more isotopically enriched atoms, for example, replacement of hydrogen with deuterium or tritium, or the replacement of a carbon by $^{13}$C- or $^{14}$C-enriched carbon. The compounds of the present invention may also contain unnatural proportions of atomic isotopes at one or more of atoms that constitute such compounds. For example, the compounds may be radiolabeled with radioactive isotopes, such as for example tritium ($^3$H), iodine-125 ($^{125}$I) or carbon-14 ($^{14}$C). All isotopic variations of the compounds of the present invention, whether radioactive or not, are encompassed within the scope of the present invention.

The present disclosure further encompasses salts of the compounds of the invention, including non-toxic pharmaceutically acceptable salts. Examples of pharmaceutically acceptable addition salts include inorganic and organic acid addition salts and basic salts. The pharmaceutically acceptable salts include, but are not limited to, metal salts such as sodium salt, potassium salt, cesium salt and the like; alkaline earth metals such as calcium salt, magnesium salt and the like; organic amine salts such as triethylamine salt, pyridine salt, picoline salt, ethanolamine salt, triethanolamine salt, dicyclohexylamine salt, N,N'-dibenzylethylenediamine salt and the like; inorganic acid salts such as hydrochloride, hydrobromide, phosphate, sulphate and the like; organic acid salts such as citrate, lactate, tartrate, maleate, fumarate, mandelate, acetate, dichloroacetate, trifluoroacetate, oxalate, formate, succinates, palmoates, benzoates, salicylates, ascorbates, glycerophosphates, ketoglutarates and the like; sulfonates such as methanesulfonate, benzenesulfonate, p-toluenesulfonate and the like; salts of natural amino acids such as glycine, alanine, valine, leucine, isoleucine, norleucine, tyrosine, cystine, cysteine, methionine, proline, hydroxy proline, histidine, omithine, lysine, arginine, and serine; and salts of non-natural amino acids such as D-isomers or substituted amino acids; salts of guanidine; and salts of substituted guanidine wherein the substituents are selected from nitro, amino, alkyl, alkenyl, alkynyl, ammonium or substituted ammonium salts and aluminum salts.

The term "selective inhibitor" as applied to a biologically active agent refers to the agent's ability to selectively reduce the target signaling activity as compared to off-target signaling activity, via direct or indirect interaction with the target.

The term "PI3Kδ selective inhibitor" refers to Compound A as defined herein, which selectively inhibits the activity of the PI3K δ isoform more effectively than other isoforms of the PI3K family (α, β, and γ). For instance, a compound of formula A can be a compound that exhibits a 50% inhibitory concentration ($IC_{50}$) with respect to the δ type PI3-kinase that is at least 20-fold lower than the inhibitor's $IC_{50}$ with respect to the rest of the other PI3K isoforms (i.e., α, β, and γ).

Inhibition of PI3K δ may be of therapeutic benefit in treatment of various conditions, e.g., conditions characterized by an inflammatory response including but not limited to autoimmune diseases, allergic diseases, and arthritic diseases. Importantly, inhibition of PI3K δ function does not appear to affect biological functions such as viability and fertility.

"Inflammatory response" as used herein is characterized by redness, heat, swelling and pain (i.e., inflammation) and typically involves tissue injury or destruction. An inflammatory response is usually a localized, protective response elicited by injury or destruction of tissues, which serves to destroy, dilute or wall off (sequester) both the injurious agent and the injured tissue. Inflammatory responses are notably associated with the influx of leukocytes and/or leukocyte (e.g., neutrophil) chemotaxis. Inflammatory responses can result from infection with pathogenic organisms and viruses, noninfectious means such as trauma or reperfusion following myocardial infarction or stroke, immune responses to foreign antigens, and autoimmune diseases. Inflammatory responses amenable to treatment with the methods and compounds according to the invention encompass conditions associated with reactions of the specific defense system as well as conditions associated with reactions of the non-specific defense system.

The therapeutic methods of the invention include methods for the treatment of conditions associated with inflammatory cell activation. "Inflammatory cell activation" refers to the induction by a stimulus (including, but not limited to, cytokines, antigens or auto-antibodies) of a proliferative cellular response, the production of soluble mediators (including but not limited to cytokines, oxygen radicals, enzymes, prostanoids, or vasoactive amines), or cell surface expression of new or increased numbers of mediators (including, but not limited to, major histocompatibility antigens or cell adhesion molecules) in inflammatory cells (including, but not limited to, monocytes, macrophages, T lymphocytes, B lymphocytes, granulocytes (polymorphonuclear leukocytes including neutrophils, basophils, and eosinophils) mast cells, dendritic cells, Langerhans cells, and endothelial cells). It will be appreciated by persons skilled in the art that the activation of one or a combination of these phenotypes in these cells can contribute to the initiation, perpetuation, or exacerbation of an inflammatory condition.

The term "autoimmune disease" as used herein refers to any group of disorders in which tissue injury is associated with humoral or cell-mediated responses to the body's own constituents.

The term "transplant rejection" as used herein refers to an immune response directed against grafted tissue (including organs or cells, e.g., bone marrow, characterized by a loss of function of the grafted and surrounding tissues, pain, swelling, leukocytosis, and thrombocytopenia).

The term "allergic disease" as used herein refers to any symptoms, tissue damage, or loss of tissue function resulting from allergy.

The term "arthritic disease" as used herein refers to any disease that is characterized by inflammatory lesions of the joints attributable to a variety of etiologies.

The term "dermatitis" as used herein refers to any of a large family of diseases of the skin that are characterized by inflammation of the skin attributable to a variety of etiologies.

The term "synergistic effect," as used herein, refers to a greater-than-additive therapeutic effect produced by a combination of compounds wherein the therapeutic effect obtained with the combination exceeds the additive effects that would otherwise result from individual administration the compounds alone. Embodiments of the invention include methods of producing a synergistic effect in the treatment of hematological cancer, wherein said effect is at least 5%, at least 10%, at least 20%, at least 30%, at least 40%, at least 50%, at least 60%, at least 70%, at least 80%, at least 90%, at least 100%, at least 200%, at least 500%, or at least 1000% greater than the corresponding additive effect.

"Therapeutic synergy," as used herein, means that a combination of an anti-CD20 antibody with Compound A produce a therapeutic effect in treatment which is greater than the additive effects of the anti-CD20 antibody the PI3Kδ selective inhibitor when each is used alone.

As used in the present disclosure and claims, the singular forms "a," "an," and "the" include plural forms unless the context clearly dictates otherwise.

It is understood that wherever embodiments are described herein with the language "comprising," otherwise analogous embodiments described in terms of "consisting of" and/or "consisting essentially of" are also provided.

II. PI3Kδ Selective Inhibitor

As provided herein the PI3Kδ selective inhibitor used in combination with anti-CD20 antibodies and antigen-binding fragments thereof is a compound of formula A:

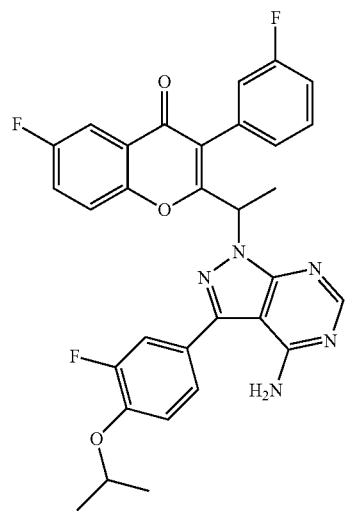

(A)

and a stereoisomer thereof, a tautomer thereof, pharmaceutically acceptable salts, solvates, and prodrugs thereof.

In one embodiment, Compound A used in combination with anti-CD20 antibodies and antigen-binding fragments thereof, is (S)-2-(1-(4-amino-3-(3-fluoro-4-isopropoxyphenyl)-1H-pyrazolo[3,4-d]pyrimidin-1-yl)ethyl)-6-fluoro-3-(3-fluorophenyl)-4H-chromen-4-one, pharmaceutically acceptable salts, solvates, and prodrugs thereof. This stereoisomer is also referred to herein as "S-isomer of a compound of formula A," "S-isomer," "TGR-1202" and "RP 5307."

In another embodiment, Compound A used in combination with anti-CD20 antibodies and antigen-binding fragments thereof, is (R)-2-(1-(4-amino-3-(3-fluoro-4-isopropoxyphenyl)-1H-pyrazolo[3,4-d]pyrimidin-1-yl)ethyl)-6-fluoro-3-(3-fluorophenyl)-4H-chromen-4-one, pharmaceutically acceptable salts, solvates, and prodrugs thereof.

The chemical structures of these compounds are shown below:

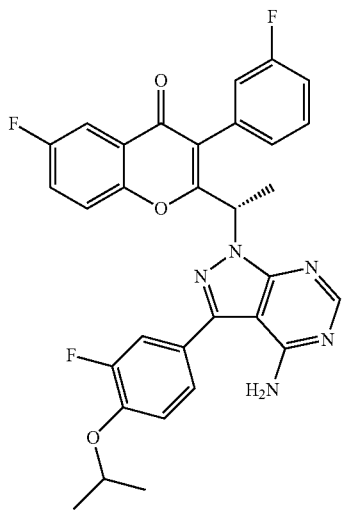

S-isomer

-continued

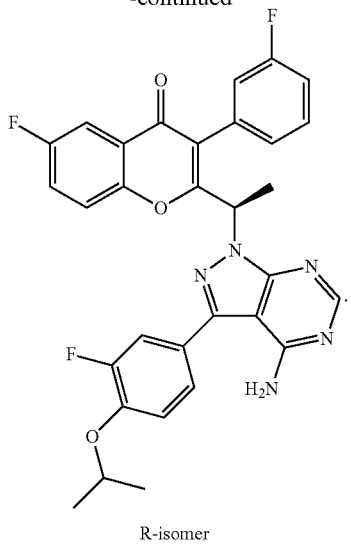

R-isomer

III. Anti-CD20 Antibodies

CD20 is a tetraspanning transmembrane phospho-protein that is expressed predominantly in pre-B cells and in mature peripheral B cells in humans and mice. In humans, CD20 is also strongly and homogeneously expressed on most mature B-cell malignancies.

As provided herein, anti-CD20 antibodies and antigen-binding fragments thereof can be used in combination with PI3Kδ selective inhibitor.

A number of anti-CD20 antibodies are known, including for example, ublituximab rituximab, ofatumumab (HuMax; Intracel), ocrelizumab, veltuzumab, GA101 (obinutuzumab), AME-133v (Applied Molecular Evolution), ocaratuzumab (Mentrik Biotech), PRO131921, tositumomab, ibritumomab-tiuxetan, hA20 (Immunomedics, Inc.), BLX-301 (Biolex Therapeutics), Reditux (Dr. Reddy's Laboratories), and PRO70769 (described in WO2004/056312).

Ublituximab (Utuxin™, LFB-R603, TG20, EMAB603) is a monoclonal antibody that targets a specific and unique epitope on CD20 and that has been bioengineered for enhanced clinical activity and potency.

Rituximab is a genetically engineered chimeric murine/human monoclonal antibody directed against the CD20 antigen. Rituximab is the antibody called "C2B8" in U.S. Pat. No. 5,736,137. The amino acid sequence of rituximab antibody and exemplary methods for its production via recombinant expression in Chinese Hamster Ovary (CHO) cells are disclosed in U.S. Pat. No. 5,736,137, which is herein incorporated by reference in its entirety.

Ofatumumab is an anti-CD20 IgG1κ human monoclonal antibody. Studies indicate that ofatumumab dissociates from CD20 at a slower rate compared to the rituximab and binds a membrane-proximal epitope. Zhang et al., Mabs 1: 326-331 (2009). Epitope mapping has indicated that ofatumumab binds an epitope located closer to the N-terminus of CD20 compared to the location targeted by rituximab and includes an extracellular loop of the antigen. Id.

Thus, in some embodiments, the anti CD-20 antibody or fragment thereof is selected from the group consisting of antibodies that bind to the same epitope as ublituximab rituximab, ofatumumab, ocrelizumab, veltuzumab, GA101, AME-133v, PRO131921, tositumomab, hA20, or PRO70769. In some embodiments, the anti-CD20 antibody or fragment thereof is ublituximab rituximab, ofatumumab, ocrelizumab, veltuzumab, GA101, AME-133v, PRO131921, tositumomab, hA20, PRO70769, or a fragment thereof.

In some embodiments, the anti-CD20 antibody or fragment thereof binds to the same epitope as ublituximab. In some embodiments, the anti-CD20 antibody or fragment thereof binds to a sequence comprising amino acids N153-S179 of CD20. In some embodiments, the anti-CD20 antibody or fragment thereof binds to a discontinuous epitope in amino acids N153-S179 of CD20.

In some embodiments, the anti-CD20 antibody or fragment thereof binds to CD20 with an affinity characterized by a dissociation constant KD of less than about $10^{-7}$ M, less than about $10^{-8}$ M or less than about $10^{-9}$ M. In some embodiments, the anti-CD20 antibody or fragment thereof binds to CD20 with an affinity characterized by a dissociation constant KD of $10^{-10}$ to $10^{-9}$ M. In some embodiments the anti-CD20 antibody or fragment thereof binds to CD20 with an affinity characterized by a dissociation constant KD of $0.7 \times 10^{-9}$ M. As used in the context of antibody binding dissociation constants, the term "about" allows for the degree of variation inherent in the methods utilized for measuring antibody affinity. For example, depending on the level of precision of the instrumentation used, standard error based on the number of samples measured, and rounding error, the term "about 10-2 M" might include, for example, from 0.05 M to 0.005 M.

In some embodiments, the anti-CD20 antibody exhibits a high affinity to Fc-gammaRIII (CD16). In some embodiments, as a result of their high affinity for the Fc region of the antibody to CD16, such antibodies are not displaced by IgG polyclonal antibodies, especially by IgG present in blood serum. In some embodiments the antibody binds to CD16 (e.g., expressed on a macrophage) with an affinity of at least $2 \times 10^6$ $M^{-1}$, at least $2 \times 10^7$ $M^{-1}$, $2 \times 10^8 M^{-1}$ or $2 \times 10^7$ $M^{-1}$, e.g., as determined by Scatchard analysis or BIAcore technology (Label-free surface plasmon resonance based technology).

In some embodiments, the anti-CD20 antibody exhibits a glycosylation pattern characterized by low fucose content in its Fc region. For example, in some embodiments, a composition comprises anti-CD20 antibodies in which the antibodies comprise N-glycoside-linked sugar chains bound on the Fc-gamma glycosylation site (Asn 297, EU numbering), wherein among the N-glycoside-linked sugar chains of all the antibodies of the composition, the fucose content is less than 65%, less than 60%, less than 55%, less than 50%, less than 45%, or less than 40%. In some embodiments, among the N-glycoside-linked sugar chains of all the antibodies of the composition, the fucose content is 15 to 45% or 20 to 40%.

In some embodiments, the anti-CD20 antibody exhibits potent in vitro antibody-dependent cellular cytotoxicity (ADCC). In some embodiments, the anti-CD20 antibody produces an ADCC plateau of at least about 10%, at least about 15%, at least about 20%, at least about 25%, or at least about 30% at a concentration of 50 ng/ml using natural killer (NK) cells from healthy donors. Techniques for measuring ADCC are known in the art and provided, for example, in de Romeauf et al., British Journal of Haematology 140: 635-643 (2008). In some embodiments, the anti-CD20 antibody produces an ADCC plateau at about 35% at a concentration of 50 ng/ml using NK cells from healthy donors.

In some embodiments, the anti-CD20 antibody can decrease NF-kappa-B activity. In some embodiments, the anti-CD20 antibody can decrease SNAIL expression. In some embodiments, the anti-CD20 antibody can increase RKIP activity. In some embodiments, the anti-CD20 antibody can increase PTEN activity. In some embodiments, the anti-CD20 antibody can increase sensitization of a cell to TRAIL-apoptosis.

In some embodiments, the anti-CD20 antibody is Fc-gamma-RIIIA (CD16) optimized. Antibodies capable of activating type III Fc receptors and having a particular glycan structure have been described, for example, in U.S. Pat. No. 7,931,895, which is herein incorporated by reference in its entirety. Thus, in some embodiments, the anti-CD20 antibody is modified on Asn 297 (EU numbering) with N-glycosylations of the bi-antennary and/or oligomannoside type as described in U.S. Pat. No. 7,931,895. Methods of producing antibodies with strong affinity for receptor CD16 of the effector cells of the immune system are provided, for example, in U.S. Published Application No. 2005/0271652, which is herein incorporated by reference in its entirety.

In some embodiments, the anti-CD20 antibody has high ADCC activity. Methods of producing antibodies with high ADCC activity are provided, for example, in U.S. Pat. No. 7,713,524, which is herein incorporated by reference in its entirety.

Ublituximab comprises the antibody sequences provided below:

```
Variable heavy chain CDR1:
                                                                (SEQ ID NO: 1)
Gly Tyr Thr Phe Thr Ser Tyr Asn Variable heavy chain CDR2:
                                                                (SEQ ID NO: 2)
Ile Tyr Pro Gly Asn Gly Asp Thr Variable heavy chain CDR3:
                                                                (SEQ ID NO: 3)
Ala Arg Tyr Asp Tyr Asn Tyr Ala Met Asp Tyr Variable heavy chain:
                                                                (SEQ ID NO: 4)
Gln Ala Tyr Leu Gln Gln Ser Gly Ala Glu Leu Val Arg Pro Gly Ala Ser Val Lys Met Ser Cys Lys Ala Ser Gly Tyr Thr Phe Thr Ser Tyr Asn Met His Trp Val Lys Gln Thr Pro Arg Gln Gly Leu Glu Trp Ile Gly Gly Ile Tyr Pro Gly Asn Gly Asp Thr Ser Tyr Asn Gln Lys Phe Lys Gly Lys Ala Thr Leu Thr Val Gly Lys Ser Ser Ser Thr Ala Tyr Met Gln Leu Ser Ser Leu Thr Ser Glu Asp Ser Ala Val Tyr Phe Cys Ala Arg Tyr Asp Tyr Asn Tyr Ala Met Asp Tyr Trp Gly Gln Gly Thr Ser Val Thr Val Ser Ser Constant heavy chain:
                                                                (SEQ ID NO: 5)
Ala Ser Thr Lys Gly Pro Ser Val Phe Pro Leu Ala Pro Ser Ser Lys Ser Thr Ser Gly Gly Thr Ala Ala Leu Gly Cys Leu Val Lys Asp Tyr Phe Pro Glu Pro Val Thr Val Ser Trp Asn Ser Gly Ala Leu Thr Ser Gly Val His Thr Phe Pro Ala Val Leu Gln Ser Ser Gly Leu Tyr Ser Leu Ser Ser Val Val Thr Val Pro Ser Ser Ser Leu Gly Thr Gln Thr Tyr Ile Cys Asn Val Asn His Lys Pro Ser Asn Thr Lys Val Asp Lys Lys Val Glu Pro Lys Ser Cys Asp Lys Thr His Thr Cys Pro Pro Cys Pro Ala Pro Glu Leu Leu Gly Gly Pro Ser Val Phe Leu Phe Pro Pro Lys Pro Lys Asp Thr Leu Met Ile Ser Arg Thr Pro Glu Val Thr Cys Val Val Val Asp Val Ser His Glu Asp Pro Glu Val Lys Phe Asn Trp Tyr Val Asp Gly Val Glu Val His Asn Ala Lys Thr Lys Pro Arg Glu Glu Gln Tyr Asn Ser Thr Tyr Arg Val Val Ser Val Leu Thr Val Leu His Gln Asp Trp Leu Asn Gly Lys Glu Tyr Lys Cys Lys Val Ser Asn Lys Ala Leu Pro Ala Pro Ile Glu Lys Thr Ile Ser Lys Ala Lys Gly Gln Pro Arg Glu Pro Gln Val Tyr Thr Leu Pro Pro Ser Arg Asp Glu Leu Thr Lys Asn Gln Val Ser Leu Thr Cys Leu Val Lys Gly Phe Tyr Pro Ser Asp Ile Ala Val Glu Trp Glu Ser Asn Gly Gln Pro Glu Asn Asn Tyr Lys Thr Thr Pro Pro Val Leu Asp Ser Asp Gly Ser Phe Phe Leu Tyr Ser Lys Leu Thr Val Asp Lys Ser Arg Trp Gln Gln Gly Asn Val Phe Ser Cys Ser Val Met His Glu Ala Leu His Asn His Tyr Thr Gln Lys Ser Leu Ser Leu Ser Pro Gly Lys
```

-continued

Variable light chain CDR1:
(SEQ ID NO: 6)
Ser Ser Val Ser Tyr

Variable light chain CDR2:
(SEQ ID NO: 7)
Ala Thr Ser

Variable light chain CDR3:
(SEQ ID NO: 8)
Gln Gln Trp Thr Phe Asn Pro Pro Thr

Variable light chain:
(SEQ ID NO: 9)
Gln Ile Val Leu Ser Gln Ser Pro Ala Ile Leu Ser Ala Ser Pro Gly Glu Lys Val Thr Met Thr Cys Arg Ala Ser Ser Ser Val Ser Tyr Met His Trp Tyr Gln Gln Lys Pro Gly Ser Ser Pro Lys Pro Trp Ile Tyr Ala Thr Ser Asn Leu Ala Ser Gly Val Pro Ala Arg Phe Ser Gly Ser Gly Ser Gly Thr Ser Tyr Ser Phe Thr Ile Ser Arg Val Glu Ala Glu Asp Ala Ala Thr Tyr Tyr Cys Gln Gln Trp Thr Phe Asn Pro Pro Thr Phe Gly Gly Gly Thr Arg Leu Glu Ile Lys Constant light chain:
(SEQ ID NO: 10)
Thr Val Ala Ala Pro Ser Val Phe Ile Phe Pro Pro Ser Asp Glu Gln Leu Lys Ser Gly Thr Ala Ser Val Val Cys Leu Leu Asn Asn Phe Tyr Pro Arg Glu Ala Lys Val Gln Trp Lys Val Asp Asn Ala Leu Gln Ser Gly Asn Ser Gln Glu Ser Val Thr Glu Gln Asp Ser Lys Asp Ser Thr Tyr Ser Leu Ser Ser Thr Leu Thr Leu Ser Lys Ala Asp Tyr Glu Lys His Lys Val Tyr Ala Cys Glu Val Thr His Gln Gly Leu Ser Ser Pro Val Thr Lys Ser Phe Asn Arg Gly Glu Cys Thus, in some embodiments, an isolated antibody or antigen-binding fragment, variant, or derivative thereof comprises, consists essentially of, or consists of an immunoglobulin heavy chain variable domain (VH domain), wherein at least one (i.e., one, two, or three) of the CDRs of the VH domain has an amino acid sequence that is at least 80%, 85%, 90%, 95%, 96%, 97%, 98%, 99%, or identical to the CDR1, CDR2 or CDR3 region of sequences SEQ ID NO:1, 2, or 3, wherein an antibody or antigen-binding fragment thereof comprising the VH domain can specifically or preferentially bind to CD20.

In another embodiment, an isolated antibody or antigen-binding fragment, variant, or derivative thereof comprises, consists essentially of, or consists of an immunoglobulin heavy chain variable domain (VH domain), wherein at least one (i.e., one, two, or three) of the CDRs of the VH domain has an amino acid sequence identical, except for 1, 2, 3, 4, or 5 conservative amino acid substitutions, to the CDR1, CDR2 or CDR3 region of sequences SEQ ID NO:1, 2, or 3, wherein an antibody or antigen-binding fragment, variant, or derivative thereof comprising the VH domain can specifically or preferentially bind to CD20.

In another embodiment, an isolated antibody or antigen-binding fragment, variant, or derivative thereof comprises, consists essentially of, or consists of a VH domain that has an amino acid sequence that is at least 80%, 85%, 90%, 91%, 92%, 93%, 94%, 95%, 96%, 97%, 98%, 99%, or 100% identical to a VH amino acid sequence of SEQ ID NO:4, wherein an antibody or antigen-binding fragment, variant, or derivative thereof comprising the VH domain can specifically or preferentially bind to CD20.

In another embodiment, an isolated antibody or antigen-binding fragment, variant, or derivative thereof comprises, consists essentially of, or consists of a heavy chain that has an amino acid sequence that is at least 80%, 85%, 90%, 91%, 92%, 93%, 94%, 95%, 96%, 97%, 98%, 99%, or 100% identical to a heavy chain amino acid sequence comprising SEQ ID NOs: 4 and 5, wherein an antibody or antigen-binding fragment, variant, or derivative thereof comprising the heavy chain can specifically or preferentially bind to CD20.

In some embodiments, an isolated antibody or antigen-binding fragment, variant, or derivative thereof comprises, consists essentially of, or consists of an immunoglobulin light chain variable domain (VL domain), wherein at least one (i.e., one, two, or three) of the CDRs of the VL domain has an amino acid sequence that is at least 80%, 85%, 90%, 95%, 96%, 97%, 98%, 99%, or identical to the CDR1, CDR2 or CDR3 region of sequences SEQ ID NO:6, 7, or 8, wherein an antibody or antigen-binding fragment thereof comprising the VL domain can specifically or preferentially bind to CD20.

In another embodiment, an isolated antibody or antigen-binding fragment, variant, or derivative thereof comprises, consists essentially of, or consists of an immunoglobulin light chain variable domain (VL domain), wherein at least one (i.e., one, two, or three) of the CDRs of the VL domain has an amino acid sequence identical, except for 1, 2, 3, 4, or 5 conservative amino acid substitutions, to the CDR1, CDR2 or CDR3 region of SEQ ID NO:6, 7, or 8, wherein an antibody or antigen-binding fragment, variant, or derivative thereof comprising the VL domain can specifically or preferentially bind to CD20.

In another embodiment, an isolated antibody or antigen-binding fragment, variant, or derivative thereof comprises, consists essentially of, or consists of a VL domain that has an amino acid sequence that is at least 80%, 85%, 90%, 91%, 92%, 93%, 94%, 95%, 96%, 97%, 98%, 99%, or 100% identical to a VL amino acid sequence of SEQ ID NO:9, wherein an antibody or antigen-binding fragment, variant, or derivative thereof comprising the VL domain can specifically or preferentially bind to CD20.

In another embodiment, an isolated antibody or antigen-binding fragment, variant, or derivative thereof comprises, consists essentially of, or consists of a light chain that has an amino acid sequence that is at least 80%, 85%, 90%, 91%, 92%, 93%, 94%, 95%, 96%, 97%, 98%, 99%, or 100% identical to a heavy chain amino acid sequence comprising SEQ ID NOs: 9 and 10, wherein an antibody or antigen-binding fragment, variant, or derivative thereof comprising the light chain can specifically or preferentially bind to CD20.

In some embodiments, an isolated antibody or antigen-binding fragment, variant, or derivative thereof comprises, consists essentially of, or consists of an immunoglobulin heavy chain variable domain (VH domain) and an immunoglobulin light chain variable domain (VL domain), wherein at least one (i.e., one, two, or three) of the CDRs of the VH domain has an amino acid sequence that is at least 80%, 85%, 90%, 95%, 96%, 97%, 98%, 99%, or identical to the CDR1, CDR2 or CDR3 region of sequences SEQ ID NO:1, 2, or 3, wherein at least one (i.e., one, two, or three) of the CDRs of the VL domain has an amino acid sequence that is at least 80%, 85%, 90%, 95%, 96%, 97%, 98%, 99%, or identical to the CDR1, CDR2 or CDR3 region of sequences SEQ ID NO:6, 7, or 8, and wherein an antibody or antigen-binding fragment thereof comprising the VH domain and VL can specifically or preferentially bind to CD20.

In another embodiment, an isolated antibody or antigen-binding fragment, variant, or derivative thereof comprises, consists essentially of, or consists of an immunoglobulin heavy chain variable domain (VH domain), and an immunoglobulin light chain variable domain (VL domain), wherein at least one (i.e., one, two, or three) of the CDRs of the VH domain has an amino acid sequence identical, except for 1, 2, 3, 4, or 5 conservative amino acid substitutions, to the CDR1, CDR2 or CDR3 region of sequences SEQ ID NO:1, 2, or 3, wherein at least one (i.e., one, two, or three) of the CDRs of the VL domain has an amino acid sequence identical, except for 1, 2, 3, 4, or 5 conservative amino acid substitutions, to the CDR1, CDR2 or CDR3 region of SEQ ID NO:6, 7, or 8, and wherein an antibody or antigen-binding fragment, variant, or derivative thereof comprising the VH and VL can specifically or preferentially bind to CD20.

In some embodiments, the anti-CD20 antibody or antigen-binding fragment, variant, or derivative thereof comprises the VH CDR1, CDR2 and CDR3 region of sequences SEQ ID NO:1, 2, and 3, and the VL CDR1, CDR2 and CDR3 region of sequences SEQ ID NO:6, 7, and 8.

In another embodiment, an isolated antibody or antigen-binding fragment, variant, or derivative thereof comprises, consists essentially of, or consists of a VH domain and a VL domain, wherein the VH has an amino acid sequence that is at least 80%, 85%, 90%, 91%, 92%, 93%, 94%, 95%, 96%, 97%, 98%, 99%, or 100% identical to a VH amino acid sequence of SEQ ID NO:4, wherein the VL domain that has an amino acid sequence that is at least 80%, 85%, 90%, 91%, 92%, 93%, 94%, 95%, 96%, 97%, 98%, 99%, or 100% identical to a VL amino acid sequence of SEQ ID NO:9, and wherein an antibody or antigen-binding fragment, variant, or derivative thereof comprising the VH and VL domain can specifically or preferentially bind to CD20.

In some embodiments, the anti-CD20 antibody or antigen-binding fragment thereof comprises the VH of SEQ ID NO:4 and the VL of SEQ ID NO:9.

In some embodiments, the anti-CD20 antibody or antigen-binding fragment thereof binds to the same epitope as an antibody comprising the VH of SEQ ID NO:4 and the VL of SEQ ID NO:9.

In another embodiment, an isolated antibody or antigen-binding fragment, variant, or derivative thereof comprises, consists essentially of, or consists of a heavy chain and a light chain, wherein the heavy chain has an amino acid sequence that is at least 80%, 85%, 90%, 91%, 92%, 93%, 94%, 95%, 96%, 97%, 98%, 99%, or 100% identical to a heavy chain amino acid sequence comprising SEQ ID NOs: 4 and 5, wherein the light chain that has an amino acid sequence that is at least 80%, 85%, 90%, 91%, 92%, 93%, 94%, 95%, 96%, 97%, 98%, 99%, or 100% identical to a heavy chain amino acid sequence comprising SEQ ID NOs: 9 and 10, and wherein an antibody or antigen-binding fragment, variant, or derivative thereof comprising the heavy chain can specifically or preferentially bind to CD20.

In some embodiments, the anti-CD20 antibody or antigen-binding fragment thereof comprises a heavy chain comprising SEQ ID NOs: 4 and 5 and a light chain comprising SEQ ID NOs: 9 and 10.

In some embodiments, the anti-CD20 antibody or antigen-binding fragment thereof binds to the same epitope as an antibody comprising SEQ ID NO:4 and SEQ ID NO:5.

In some embodiments, the anti-CD20 antibody is ublituximab.

In some embodiments, the antibody is EMAB603 (see WO2006/064121, which is herein incorporated by reference in its entirety), produced by the clone R603-12D11, deposited to the Collection Nationale des Cultures de Microorganismes under the accession number CNCM I-3529.

In some embodiments, the anti-CD20 antibody is produced in the rat hybridoma YB2/0 cell line (cell YB2/3HL.P2.G11.16Ag.20, registered at the American Type Culture Collection under ATCC number CRL-1662).

The precise chemical structure of an antibody capable of specifically binding CD20 and retaining the desired activity depends on a number of factors. As ionizable amino and carboxyl groups are present in the molecule, a particular polypeptide can be obtained as an acidic or basic salt, or in neutral form. All such preparations that retain their biological activity when placed in suitable environmental conditions are included in the definition of anti-CD20 antibodies as used herein. Further, the primary amino acid sequence of the antibody can be augmented by derivatization using sugar moieties (glycosylation) or by other supplementary molecules such as lipids, phosphate, acetyl groups and the like. It can also be augmented by conjugation with saccharides. Certain aspects of such augmentation are accomplished through post-translational processing systems of the producing host; other such modifications can be introduced in vitro. In any event, such modifications are included in the definition of an anti-CD20 antibody used herein so long as the desired properties of the anti-CD20 antibody are not destroyed. It is expected that such modifications can quantitatively or qualitatively affect the activity, either by enhancing or diminishing the activity of the polypeptide, in the various assays. Further, individual amino acid residues in the chain can be modified by oxidation, reduction, or other derivatization, and the polypeptide can be cleaved to obtain fragments that retain activity. Such alterations that do not destroy the desired properties (e.g., binding specificity for CD20) do not remove the polypeptide sequence from the definition of anti-CD20 antibodies of interest as used herein.

The art provides substantial guidance regarding the preparation and use of polypeptide variants. In preparing variants of an anti-CD20 binding molecule, e.g., an antibody or antigen-binding fragment, variant, or derivative thereof, one of skill in the art can readily determine which modifications to the native protein's nucleotide or amino acid sequence will result in a variant that is suitable for use as a therapeutically active component of a pharmaceutical composition.

It is possible to introduce mutations only in framework regions or only in CDR regions of an antibody molecule. Introduced mutations can be silent or neutral missense mutations, i.e., have no, or little, effect on an antibody's ability to bind antigen. These types of mutations can be useful to optimize codon usage, or improve a hybridoma's antibody production. Alternatively, non-neutral missense mutations can alter an antibody's ability to bind antigen. The location of most silent and neutral missense mutations is likely to be in the framework regions, while the location of most non-neutral missense mutations is likely to be in CDR, though this is not an absolute requirement. One of skill in the art would be able to design and test mutant molecules with desired properties such as no alteration in antigen-binding activity or alteration in binding activity (e.g., improvements in antigen-binding activity or change in antibody specificity). Following mutagenesis, the encoded protein can routinely be expressed and the functional and/or biological activity of the encoded protein, (e.g., ability to immunospecifically bind at least one epitope of a CD20 polypeptide) can be determined using techniques described herein or by routinely modifying techniques known in the art.

In certain embodiments, the anti-CD20 antibodies comprise at least one optimized complementarity-determining region (CDR). By "optimized CDR" is intended that the CDR has been modified and optimized sequences selected based on the sustained or improved binding affinity and/or anti-CD20 activity that is imparted to an anti-CD20 antibody comprising the optimized CDR. "Anti-CD20 activity" can include, e.g., activity which modulates one or more of the following activities associated with CD20, e.g., the ability to induce apoptosis of B-cells, the ability to induce ADCC against B-cells (e.g., CLL cells), the ability to inhibit NF-kappaB activity, the ability to inhibit Snail expression, the ability to de-repress RKIP, the ability to de-repress PTEN, the ability to sensitize a tumor cell to TRAIL-apoptosis or any other activity associated with CD20. Such activities are described, for example, in Baritaki et al., *International Journal of Oncology* 38: 1683-1694 (2011), which is herein incorporated by reference in its entirety. The modifications can involve replacement of amino acid residues within the CDR such that an anti-CD20 antibody retains specificity for the CD20 antigen and has improved binding affinity and/or improved anti-CD20 activity.

In certain anti-CD20 antibodies, or antigen-binding fragments thereof, at least a fraction of one or more of the constant region domains has been deleted or otherwise altered so as to provide desired biochemical characteristics such as reduced effector functions, the ability to non-covalently dimerize, increased ability to localize at the site of a tumor, reduced serum half-life, or increased serum half-life when compared with a whole, unaltered antibody of approximately the same immunogenicity. For example, certain antibodies are domain deleted antibodies which comprise a polypeptide chain similar to an immunoglobulin heavy chain, but which lack at least a portion of one or more heavy chain domains. For instance, in certain antibodies, one entire domain of the constant region of the modified antibody will be deleted, for example, all or part of the CH2 domain will be deleted.

In certain anti-CD20 antibodies or antigen-binding fragments thereof, the Fc portion can be mutated to decrease effector function using techniques known in the art. For example, modifications of the constant region can be used to modify disulfide linkages or oligosaccharide moieties that allow for enhanced localization due to increased antigen specificity or antibody flexibility. The resulting physiological profile, bioavailability and other biochemical effects of the modifications can easily be measured and quantified using well know immunological techniques without undue experimentation.

In certain embodiments, an anti-CD20 antibody or antigen-binding fragment thereof will not elicit a deleterious immune response in the animal to be treated, e.g., in a human. In one embodiment, anti-CD20 antibodies or antigen-binding fragments thereof can be modified to reduce their immunogenicity using art-recognized techniques. For example, antibodies can be humanized, primatized, deimmunized, or chimeric antibodies can be made. These types of antibodies are derived from a non-human antibody, typically a murine or primate antibody, that retains or substantially retains the antigen-binding properties of the parent antibody, but which is less immunogenic in humans. This can be achieved by various methods, including (a) grafting the entire non-human variable domains onto human constant regions to generate chimeric antibodies; (b) grafting at least a part of one or more of the non-human complementarity determining regions (CDRs) into a human framework and constant regions with or without retention of critical framework residues; or (c) transplanting the entire non-human variable domains, but "cloaking" them with a human-like section by replacement of surface residues. Such methods are disclosed in Morrison et al., *Proc. Natl. Acad. Sci.* 81:6851-6855 (1984); Morrison et al., *Adv. Immunol.* 44:65-92 (1988); Verhoeyen et al., *Science* 239:1534-1536 (1988); Padlan, *Molec. Immun.* 28:489-498 (1991); Padlan, *Molec. Immun.* 31:169-217 (1994), and U.S. Pat. Nos. 5,585,089, 5,693,761, 5,693,762, and 6,190,370, all of which are hereby incorporated by reference in their entirety.

Modified forms of antibodies or antigen-binding fragments thereof can be made from whole precursor or parent antibodies using techniques known in the art.

Anti-CD20 antibodies or antigen-binding fragments thereof can be made or manufactured using techniques that are known in the art. In certain embodiments, antibody molecules or fragments thereof are "recombinantly produced," i.e., are produced using recombinant DNA technology. Anti-CD20 antibodies or fragments thereof can be generated by any suitable method known in the art including generation of polyclonal antibodies or preparation of monoclonal antibodies, e.g., through hybridoma or phage display.

A variety of host-expression vector systems can be utilized to express antibody molecules. The host cell can be co-transfected with two expression vectors, the first vector encoding a heavy chain derived polypeptide and the second vector encoding a light chain derived polypeptide. The two vectors can contain identical selectable markers which enable equal expression of heavy and light chain polypeptides. Alternatively, a single vector can be used which encodes both heavy and light chain polypeptides. In such situations, the light chain is advantageously placed before the heavy chain to avoid an excess of toxic free heavy chain (Proudfoot, Nature 322:52 (1986); Kohler, Proc. Natl. Acad. Sci. USA 77:2197 (1980)). The host cell can also be transfected with a single vector encoding a heavy chain derived polypeptide and a light chain derived polypeptide. The coding sequences for the heavy and light chains can comprise cDNA or genomic DNA.

The expression vector or vectors can be transferred to a host cell by conventional techniques and the transfected cells are then cultured by conventional techniques to produce an antibody. Thus, host cells containing a polynucleotide encoding an antibody, or a heavy or light chain thereof, operably linked to a heterologous promoter are provided. In certain embodiments for the expression of double-chained antibodies, vectors encoding both the heavy and light chains can be co-expressed in the host cell for expression of the entire immunoglobulin molecule.

Host-expression systems represent vehicles by which the coding sequences of interest can be produced and subsequently purified, but also represent cells which can, when transformed or transfected with the appropriate nucleotide coding sequences, express a CD20 antibody in situ. These include but are not limited to microorganisms such as bacteria (e.g., *E. coli, B. subtilis*) transformed with recombinant bacteriophage DNA, plasmid DNA or cosmid DNA expression vectors containing antibody coding sequences; yeast (e.g., *Saccharomyces, Pichia*) transformed with recombinant yeast expression vectors containing antibody coding sequences; insect cell systems infected with recombinant virus expression vectors (e.g., baculovirus) containing antibody coding sequences; plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing antibody coding sequences; or mammalian cell systems (e.g., COS, CHO, BLK, 293, 3T3 cells) harboring recombinant expression constructs containing promoters derived from the genome of mammalian cells (e.g., metallothionein promoter) or from mammalian viruses (e.g., the adenovirus late promoter; the vaccinia virus 7.5K promoter). Bacterial cells such as *Escherichia coli*, or eukaryotic cells, e.g., for the expression of whole recombinant antibody molecules, are used for the expression of a recombinant antibody molecule. For example, mammalian cells such as Chinese hamster ovary cells (CHO), in conjunction with a vector such as the major intermediate early gene promoter element from human cytomegalovirus is an effective expression system for antibodies (Foecking et al., Gene 45:101 (1986); Cockett et al., Bio/Technology 8:2 (1990)). In some embodiments, the anti-CD20 antibody is produced in a host cell that is not a CHO cell.

Once an antibody has been recombinantly expressed, it can be purified by any method known in the art for purification of an immunoglobulin molecule, for example, by chromatography (e.g., ion exchange, affinity, particularly by affinity for the specific antigen after Protein A, and sizing column chromatography), centrifugation, differential solubility, or by any other standard technique for the purification of proteins.

In some embodiments, the anti-CD20 antibody is produced by a rat hybridoma cell line. In some embodiments, the anti-CD20 antibody is produced in YB2/0 (ATCC CRL-1662)

IV. Pharmaceutical Compositions

A compound of formula A and anti-CD20 antibodies can be administered in any order or at any interval as determined by one of skill in the art. For example, a compound of formula A and anti-CD20 antibody can be administered sequentially (in any order), simultaneously, or via any combination of sequential and simultaneous administrations. A compound of formula A and anti-CD20 antibody can be administered in the same pharmaceutical compositions or in separate pharmaceutical compositions.

Administration of combination, whether simultaneous, sequential (in any order) or both, can be performed according to any number of desired intervals of minutes (e.g., 0-60 minutes), hours (e.g., 0-24 hours), days (e.g., 0-7 days), and/or weeks (e.g., 0-52 weeks) as can be decided and determined by one of skill in the art. The dosing can also vary over time, for example, starting with a once weekly dose for a period of time (e.g., for 1, 2, 3, 4, 5, or 6 weeks) followed by dosing once every two weeks, once every three weeks, once every four weeks, once every five weeks, or once every six weeks.

The Compound of formula A and anti-CD20 antibodies can be formulated into pharmaceutical compositions for administration to mammals, including humans. The pharmaceutical compositions comprise pharmaceutically acceptable carriers, including, e.g., ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

The compositions can be administered by any suitable method, e.g., parenterally, intraventricularly, orally, by inhalation spray, topically, rectally, nasally, buccally, vaginally or via an implanted reservoir. In some embodiments, the Compound of formula A is administered orally. The term "parenteral" as used herein includes subcutaneous, intravenous, intramuscular, intra-articular, intra-synovial, intrasternal, intrathecal, intrahepatic, intralesional and intracranial injection or infusion techniques.

Parenteral formulations can be a single bolus dose, an infusion or a loading bolus dose followed with a maintenance dose. These compositions can be administered at specific fixed or variable intervals, e.g., once a day, or on an "as needed" basis. In some embodiments, the anti-CD20 antibody is administered intravenously (IV).

Certain pharmaceutical compositions can be orally administered in an acceptable dosage form including, e.g., capsules, tablets, aqueous suspensions or solutions. Certain pharmaceutical compositions also can be administered by nasal aerosol or inhalation. Such compositions can be prepared as solutions in saline, employing benzyl alcohol or other suitable preservatives, absorption promoters to enhance bioavailability, and/or other conventional solubilizing or dispersing agents.

A specific dosage and treatment regimen for any particular patient will depend upon a variety of factors, including the particular therapeutic agents used, the patient's age, body weight, general health, sex, and diet, and the time of administration, rate of excretion, drug combination, and the severity of the particular disease being treated. Judgment of such factors by medical caregivers is within the ordinary skill in the art. The amount will also depend on the individual patient to be treated, the route of administration, the type of formulation, the characteristics of the compound used, the severity of the disease, and the desired effect. The amount used can be determined by pharmacological and pharmacokinetic principles well known in the art.

In some embodiments, the anti-CD20 antibody is administered at a dose of less than 187.5 mg/m$^2$, 75 mg/m$^2$, 37.5 mg/m$^2$, 15 mg/m$^2$, 7.5 mg/m$^2$, 3.75 mg/m$^2$. In some embodiments, the dose administered can be 187.5 mg/m$^2$ to 75 mg/m$^2$, 75 mg/m$^2$ to 37.5 mg/m$^2$, 75 mg/m$^2$ to 15 mg/m$^2$, 75 mg/m$^2$ to 7.5 mg/m$^2$, or 75 mg/m$^2$ to 3.75 mg/m$^2$.

In some embodiments, a compound of formula A is administered at a dose range of 10 to 2500 mg/day, 10 to 1500 mg/day, 50 to 1000 mg/day, 100 to 750 mg mg/day, 150 to 500 mg/day per day. In some embodiments, the dose administered can be 200 to 400 mg per day. In some embodiments, the dose administered can be 500, 1000, 1500, 2000 or 2500 mg/day.

Supplementary active compounds also can be incorporated into the compositions. For example, an anti-CD20 antibody and a Compound of formula A can be coformulated with and/or coadministered with one or more additional therapeutic agents, such as anti-cancer agents.

V. Kits

The present invention provides kits that comprise a compound of formula A, anti-CD20 antibodies, other agents and that can be used to perform the methods described herein, and combinations thereof. In certain embodiments, a kit comprises at least one purified antibody against CD20 in one or more containers and instructions for using the antibody in combination with a compound of formula A. In certain embodiments, a kit comprises a compound of formula A and instructions for using the inhibitor in combination with an anti-CD20 antibody. In certain embodiments, a kit comprises at least one anti-CD20 antibody and a compound of formula A.

Pharmaceutical kits comprising one or more containers filled with one or more of the ingredients of the pharmaceutical compounds and compositions of the present invention, including, a compound of formula A and/or one or more anti-CD20 antibodies are also provided herein. Such kits can also include, for example, other compounds and/or compositions, a device(s) for administering the compounds and/or compositions, and written instructions in a form prescribed by a governmental agency regulating the manufacture, use or sale of pharmaceuticals or biological products One skilled in the art will readily recognize that the disclosed antibodies and a compound of formula A described herein can be readily incorporated into one of the established kit formats which are well known in the art.

Further provided are kits comprising a (a) a compound of formula A, an anti-CD20 antibody, or a combination thereof and (b) an additional anti-cancer agent. In certain embodiments, the additional anti-cancer agent is a chemotherapeutic agent.

VI. Methods of Using Combinations of a Compound of Formula A and Anti-CD20 Antibodies Combinations of a compound of formula A and anti-CD20 antibodies can be used in methods of treating diseases or disorders in a subject.

Thus, uses of a compound of formula A in the manufacture of a medicament for the treatment of a proliferative disorder wherein the a compound of formula A is to be administered in combination (e.g., sequentially or simultaneously) with an anti-CD20 antibody are provided. In addition, uses of an anti-CD20 antibody in the manufacture of a medicament for the treatment of a proliferative disorder wherein the anti-CD20 antibody is to be administered in combination (e.g., sequentially or simultaneously) with a compound of formula A are also provided.

The invention further provides a method of inhibiting PI3Kδ isoform and/or CD20 in a patient by administering to a patient an effective amount of a combination of the present invention.

The invention further provides a method of treating, preventing, and/or inhibiting a PI3Kδ mediated disease, disorder or condition and/or a CD20 mediated disease, disorder, or condition (such as cancer or other proliferative disease or disorder) in a patient by administering to the a patient an effective amount of a combination of the present invention.

The invention further provides a method of treating a PI3Kδ isoform and/or CD20 associated disease, disorder or condition in a patient by administering to the patient an effective amount of a combination of the present invention. In one embodiment, the amount of the compound administered in a combination is sufficient to treat a PI3Kδ isoform and/or CD20 associated disease, disorder or condition by selective inhibition of PI3K δ and/or CD20

The invention further provides a method for treating a proliferative disease by administering to a patient in need of such treatment an effective amount of at least one compound of formula A and antibody of the present invention. In one embodiment, the amount of the compound administered in combination is sufficient to treat the proliferative disease by selective inhibition of PI3K δ and/or inhibition of CD20.

The invention further provides a method for treating a proliferative disease by administering to a patient in need of such treatment an effective amount of a combination of the present invention, in further combination (simultaneously or sequentially) with at least one other anti-cancer agent. In one embodiment, the amount of the compound A administered is sufficient to treat (or facilitate treatment of) the proliferative disease by selective inhibition of PI3K δ.

The combinations of the present invention are useful in the treatment of a variety of cancers, including, but not limited to, the following:

carcinoma, including that of the bladder, breast, colon, kidney, liver, lung (including small cell lung cancer), esophagus, gall bladder, uterus, ovary, testes, larynx, oral cavity, gastrointestinal tract (e.g., esophagus, stomach, pancreas), brain, cervix, thyroid, prostate, blood, and skin (including squamous cell carcinoma);

hematopoietic tumors of lymphoid lineage, including leukemia, acute lymphocytic leukemia, acute lymphoblastic leukemia, B-cell lymphoma, T-cell lymphoma, Hodgkin's lymphoma, non-Hodgkins lymphoma, hairy cell lymphoma and Burkett's lymphoma;

hematopoietic tumors of myeloid lineage, including acute and chronic myelogenous leukemias, myelodysplastic syndrome and promyelocytic leukemia;

tumors of mesenchymal origin, including fibrosarcoma and rhabdomyosarcoma;

tumors of the central and peripheral nervous system, including astrocytoma, neuroblastoma, glioma and schwannomas; and other tumors, including melanoma, seminoma, teratocarcinoma, osteosarcoma, xenoderoma pigmentosum, keratoctanthoma, thyroid follicular cancer and Kaposi's sarcoma.

The combinations of the present invention as modulators of apoptosis are useful in the treatment, prevention, and inhibition of cancer (including, but not limited to, those types mentioned herein above).

The combinations of the present invention are useful in the chemoprevention of cancer. Chemoprevention involves inhibiting the development of invasive cancer by blocking the initiating mutagenic event, blocking the progression of pre-malignant cells that have already suffered an insult, or inhibiting tumor relapse. The compounds are also useful in inhibiting tumor angiogenesis and metastasis. One embodiment of the invention is a method of inhibiting tumor angiogenesis or metastasis in a patient by administering an effective amount of one or more compounds of the present invention.

The invention further provides a method of treating an immune system-related disease (e.g., an autoimmune disease), a disease or disorder involving inflammation (e.g., asthma, chronic obstructive pulmonary disease, rheumatoid arthritis, inflammatory bowel disease, glomerulonephritis, neuroinflammatory diseases, multiple sclerosis, uveitis and disorders of the immune system), cancer or other proliferative disease, a hepatic disease or disorder, or a renal disease or disorder. The method includes administering an effective amount of a combination of the present invention.

Examples of immune disorders which can be treated by the compounds of the present invention include, but are not limited to, psoriasis, rheumatoid arthritis, vasculitis, inflammatory bowel disease, dermatitis, osteoarthritis, asthma, inflammatory muscle disease, allergic rhinitis, vaginitis, interstitial cystitis, scleroderma, osteoporosis, eczema, allogeneic or xenogeneic transplantation (organ, bone marrow, stem cells and other cells and tissues) graft rejection, graft-versus-host disease, lupus erythematosus, inflammatory disease, type I diabetes, pulmonary fibrosis, dermatomyositis, Sjogren's syndrome, thyroiditis (e.g., Hashimoto's and autoimmune thyroiditis), myasthenia gravis, autoimmune hemolytic anemia, multiple sclerosis, cystic fibrosis, chronic relapsing hepatitis, primary biliary cirrhosis, allergic conjunctivitis and atopic dermatitis.

The invention further provides a method of treating leukemia in a patient by administering a therapeutically effective amount of a combination of the present invention. For example, the methods of the present invention are effective for treating chronic lymphocytic leukemia (CLL), non-Hodgkin lymphoma (NHL), acute myeloid leukemia (AML), multiple myeloma (MM), small lymphocytic lymphoma (SLL), and indolent non-Hodgkin's lymphoma (I-NHL).

In the aforementioned methods of treatment, one or more additional active agents can be administered with the combinations of the present invention. For example, the combination of the present invention are useful in combining (administered together or sequentially) with known anti-cancer treatments such as radiation therapy or with one or more cytostatic, cytotoxic or anticancer agents, such as, for example, DNA interactive agents, such as cisplatin or doxorubicin; topoisomerase II inhibitors, such as etoposide; topoisomerase I inhibitors such as CPT-11 or topotecan; tubulin interacting agents, such as paclitaxel, docetaxel or the epothilones (for example ixabepilone), either naturally occurring or synthetic; hormonal agents, such as tamoxifen; thymidilate synthase inhibitors, such as 5-fluorouracil; and anti-metabolites, such as methotrexate; other tyrosine kinase inhibitors such as Iressa and OSI-774; angiogenesis inhibitors; EGF inhibitors; VEGF inhibitors; CDK inhibitors; SRC inhibitors; c-Kit inhibitors; Her1/2 inhibitors and monoclonal antibodies directed against growth factor receptors such as erbitux (EGF) and herceptin (Her2); and other protein kinase modulators. The additional active agent can also be a proteasome inhibitor, Bortezomib (Velcade®), Carfilzomib (PR-171), PR-047, disulfiram, lactacystin, PS-519, eponemycin, epoxomycin, aclacinomycin, CEP-1612, MG-132, CVT-63417, PS-341, vinyl sulfone tripeptide inhibitors, ritonavir, PI-083, (+/−)-7-methylomuralide, (−)-7-methylomuralide, lenalidomide (Revlimid®), or a combination thereof.

The combinations of the present invention are also useful in combining (administered together or sequentially) with one or more steroidal anti-inflammatory drugs, non-steroidal anti-inflammatory drugs (NSAIDs) or immune selective anti-inflammatory Derivatives (ImSAIDs).

In a particular embodiment, the cancer is a hematological malignancy and/or solid tumor. In another particular embodiment, the hematological malignancy is leukemia or lymphoma.

In some embodiments, lymphoma is a mature (peripheral) B-cell neoplasm. In specific embodiments, the mature B-cell neoplasm is selected from the group consisting of B-cell chronic lymphocytic leukemia/small lymphocytic lymphoma; B-cell prolymphocytic leukemia; Lymphoplasmacytic lymphoma; Marginal zone lymphoma, such as Splenic marginal zone B-cell lymphoma (+/−villous lymphocytes), Nodal marginal zone lymphoma (+/−monocytoid B-cells), and Extranodal marginal zone B-cell lymphoma of mucosa-associated lymphoid tissue (MALT) type; Hairy cell leukemia; Plasma cell myeloma/plasmacytoma; Follicular lymphoma, follicle center; Mantle cell lymphoma; Diffuse large cell B-cell lymphoma (including Mediastinal large B-cell lymphoma, Intravascular large B-cell lymphoma, and Primary effusion lymphoma); and Burkitt's lymphoma/Burkitt's cell leukemia.

In some embodiments, lymphoma is selected from the group consisting of multiple myeloma (MM) and non-Hodgkin's lymphoma (NHL), mantle cell lymphoma (MCL), follicular lymphoma, Waldenstrom's macroglobulinemia (WM) or B-cell lymphoma and diffuse large B-cell lymphoma (DLBCL).

In a further particular embodiment, leukemia is selected from the group consisting of acute lymphocytic leukemia/acute lymphoblastic leukemia (ALL), acute myeloid leukemia (AML), chronic lymphocytic leukemia (CLL), and small lymphocytic lymphoma (SLL). In some embodiments, Non-Hodgkin's Lymphoma (NHL) is aggressive NHL or indolent NHL. Examples of aggressive NHL includes B-cell neoplasms, diffuse large B-cell lymphoma, T/NK cell neoplasms, anaplastic large cell lymphoma, peripheral T-cell lymphomas, precursor B-lymphoblastic leukemia/lymphoma, precursor T-lymphoblastic leukemia/lymphoma, Burkitt's lymphoma, Adult T-cell lymphoma/leukemia (HTLV1+), primary CNS lymphoma, mantle cell lymphoma, polymorphic post-transplantation lymphoproliferative disorder (PTLD), AIDS-related lymphoma, true histiocytic lymphoma, and blastic NK-cell lymphoma. The most common type of aggressive NHL is diffuse large cell lymphoma. Non-limiting examples of indolent NHL include follicular lymphoma, small lymphocytic lymphoma, marginal zone lymphoma (such as extranodal marginal zone lymphoma (also called mucosa associated lymphoid tissue—MALT lymphoma), nodal marginal zone B-cell lymphoma (monocytoid B-cell lymphoma), splenic marginal zone lymphoma), and lymphoplasmacytic lymphoma (Waldenstrom's macroglobulinemia). In some embodiments, a subject has aggressive NHL or indolent NHL.

In some embodiments, a patient has a condition selected from the group consisting of mantle cell lymphoma (MCL), diffuse large B cell lymphoma (DLBCL), follicular lymphoma (FL), acute lymphocytic leukemia (ALL), acute myeloid leukemia (AML), chronic lymphocytic leukemia (CLL), and small lymphocytic lymphoma (SLL), multiple myeloma (MM), and marginal zone lymphoma.

In some embodiments, a patient has a relapsed or refractory condition. In a particular embodiment, the subject is refractory to chemotherapy treatment, or in relapse after treatment with chemotherapy.

In some embodiments, the cancer is resistant to treatment with rituximab. In some embodiments, the cancer shows a reduced response to treatment with rituximab. In some embodiments, the subject has previously been treated with rituximab.

In a particular embodiment, the methods comprise reducing the level of NF-kappa-B activity, reducing SNAIL expression, increasing RKIP activity, increasing PTEN activity, increasing tumor sensitivity to TRAIL-apoptosis, reducing the level of PI3K δ activity or a combination thereof in a patient.

In a particular embodiment, the combination of the compound of formula A and the anti-CD20 antibody depletes B-cells from human whole blood. In some embodiments, the combination of the compound of formula A and the anti-CD20 antibody depletes B-cells from human whole blood to a greater extent than either the compound of formula A or the anti-CD20 antibody alone depletes B-cells from human whole blood. In some embodiments, the combination of the compound of formula A and the anti-CD20 antibody depletes B-cells from human whole blood to a greater extent than the sum of the depletion by the compound of formula A and the depletion by the anti-CD20 antibody.

In some embodiments, a compound of formula A and anti-CD20 antibody are used in a method of treating a disease or disorder associated with excessive B-cell proliferation, wherein the method comprises administration of a compound of formula A and the anti-CD20 antibody to a subject in need thereof. In some embodiments, a compound of formula A and anti-CD20 antibody are used in a method of treating a disease or disorder associated with excessive B-cell activity, wherein the method comprises administration of a compound of formula A and the anti-CD20 antibody to a subject in need thereof. In some embodiments, a compound of formula A and anti-CD20 antibody are used in a method of treating a disease or disorder associated with excessive number of B-cells, wherein the method comprises administration of a compound of formula A and the anti-CD20 antibody to a subject in need thereof.

A compound of formula A can be prepared using the general synthetic methods as disclosed in International Patent Application Publication No. WO 2011/055215 A2 and U.S. Patent Application Publication No. 2011/0118257 A1, and specific compound preparation is as disclosed in Indian provisional patent application 2693/CHE/2012 filed 4 Jul. 2012, U.S. provisional patent application U.S. Ser. No. 61/691,586 filed 21 Aug. 2012, PCT/US2013/055434 filed 2 Jul. 2013 and U.S. Ser. No. 13/933,856 filed 2 Jul. 2013. The entirety of each of these applications and publications is incorporated herein by reference.

EXAMPLES

Synthesis of Compound of Formula A

Unless otherwise stated, purification implies column chromatography using silica gel as the stationary phase and a mixture of petroleum ether (boiling at 60-80° C.) and ethyl acetate or dichloromethane and methanol of suitable polarity as the mobile phases. The term "RT" refers to ambient temperature (25-28° C.).

Intermediate 1: 2-(1-bromoethyl)-6-fluoro-3-(3-fluorophenyl)-4H-chromen-4-one

Step-1

[1-(5-Fluoro-2-hydroxyphenyl)-2-(3-fluorophenyl)ethanone]: 3-Fluorophenylacetic acid (7.33 g, 47.56 mmoles) was dissolved in 25 ml dichloromethane. To this mixture, oxalylchloride (7.54 g, 59.46 mmoles) and DMF (3 drops) were added at 0° C. and stirred for 30 min. The solvent was evaporated and dissolved in 25 ml dichloromethane. To this mixture, 4-fluoroanisole (5.00 g, 39.64 mmoles) was added and cooled to 0° C. At 0° C. $AlCl_3$ (7.95 g, 59.46 mmoles) was added and the reaction mixture was warmed to RT and stirred for 12 hours. The reaction mixture was quenched by the addition of 2N HCl, extracted with ethyl acetate, dried over sodium sulphate and concentrated. The crude product was purified by column chromatography with ethyl acetate: petroleum ether to afford the title compound as colorless solid (4.5 g, 45% yield). $^1$H-NMR (δ ppm, DMSO-$D_6$, 400 MHz): δ 11.34 (s, 1H), 7.75 (dd, J=9.4, 3.1 Hz, 1H), 7.42 (m, 2H), 7.12 (m, 3H), 7.05 (dd, J=9.0, 4.5 Hz, 1H), 4.47 (s, 2H).

Step-2

[2-Ethyl-6-fluoro-3-(3-fluorophenyl)-4H-chromen-4-one]: 1-(5-Fluoro-2-hydroxyphenyl)-2-(3-fluorophenyl)ethanone obtained from Step-1 (3.00 g, 12.08 mmoles) was placed in a round bottom flask and to this triethylamine (25 ml) and propionic anhydride (4.92 g, 37.82 mmoles) were added, and the mixture was refluxed for 24 hours. After cooling to RT, the reaction mixture was acidified by the addition of 1N HCl solution, extracted with ethyl acetate, washed with sodium bicarbonate solution, dried with sodium sulphate and concentrated. The crude product was purified by column chromatography with ethyl acetate: petroleum ether to afford the title compound as off-yellow solid (1.80 g, 52% yield). $^1$H-NMR (δ ppm, DMSO-$D_6$, 400 MHz): δ 7.80 (m, 1H), 7.76 (m, 2H), 7.51 (dd, J=8.0, 6.4 Hz), 7.22 (m, 1H), 7.18 (m, 2H), 2.56 (q, J=7.6 Hz, 2H), 1.20 (t, J=7.6 Hz, 3H).

Step-3:

To a solution of 2-Ethyl-6-fluoro-3-(3-fluorophenyl)-4H-chromen-4-one obtained from Step-2 (1.80 g, 6.28 mmoles) in carbon tetrachloride (20 ml), N-bromosuccinimide (1.11 g, 6.28 mmoles) was added and heated to 80° C. Azobisisobutyronitrile (10 mg) was added to the reaction mixture at 80° C. After 12 hours, the reaction mixture was cooled to RT, diluted with dichloromethane and washed with water. The organic layer was dried over sodium sulphate and concentrated under reduced pressure to afford the crude title compound as yellow solid (1.25 g, 55% yield). $^1$H-NMR (δ ppm, DMSO-$D_6$, 400 MHz): δ 7.91 (dd, J=9.2, 4.3 Hz, 1H), 7.81 (dt, J=8.2, 2.8 Hz, 1H), 7.74 (dd, J=8.3, 3.1 Hz, 1H), 7.57 (m, 1H), 7.32 (dt, J=8.5, 2.4 Hz, 1H), 7.19 (m, 2H), 5.00 (q, J=6.8 Hz, 1H), 1.97 (d, J=6.8 Hz, 3H).

Intermediate 2: 6-fluoro-3-(3-fluorophenyl)-2-(1-hydroxyethyl)-4H-chromen-4-one

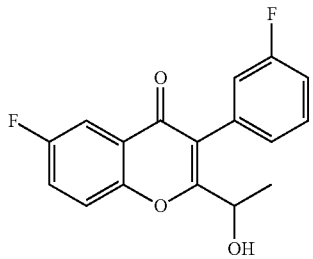 [SMILES: CC(O)c1oc2ccc(F)cc2c(=O)c1-c1cccc(F)c1]

To a solution of Intermediate 1 (15.0 g, 40.84 mmol) in DMSO (150 ml), n-butanol (7.5 ml) was added and heated to 120° C. for 3 hours. The reaction mixture was cooled to RT, quenched with water and extracted with ethyl acetate. The organic layer was dried over sodium sulphate and concentrated under reduced pressure. The crude product was purified by column chromatography with ethyl acetate: petroleum ether to afford the title compound as an off-white solid (7.90 g, 64%). $^1$H-NMR (δ ppm, CDCl$_3$, 400 MHz): 7.85 (dd, J=8.1, 3 Hz, 1H), 7.54 (dd, J=9.2, 4.2 Hz, 1H), 7.47-7.37 (m, 2H), 7.15-6.98 (m, 3H), 4.74 (quintet, J=6.8 Hz, 1H), 2.23 (d, J=7.4 Hz, 1H), 1.54 (d, J=6.6 Hz, 3H).

Intermediate 3: 2-acetyl-6-fluoro-3-(3-fluorophenyl)-4H-chromen-4-one

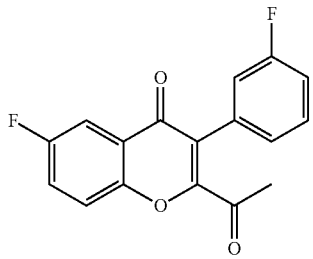 [SMILES: CC(=O)c1oc2ccc(F)cc2c(=O)c1-c1cccc(F)c1]

DMSO (5.60 ml, 79.14 mmol) was added to dichloromethane (40 ml), and cooled to −78° C., followed by oxalyl chloride (3.40 ml, 39.57 mmol). After 10 min., intermediate 2 (6.00 g, 19.78 mmol) in dichloromethane (54 ml) was added dropwise and stirred for 20 min. Triethylamine (12 ml) was added and stirred for 1 hour. The reaction mixture was quenched with water and extracted with dichloromethane. The organic layer was dried over sodium sulphate and concentrated under reduced pressure. The crude product was purified by column chromatography with ethyl acetate:petroleum ether to afford the title compound as a yellow solid (4.2 g, 71%) which was used as such in the next step.

Intermediate 4: (S)-6-fluoro-3-(3-fluorophenyl)-2-(1-hydroxyethyl)-4H-chromen-4-one

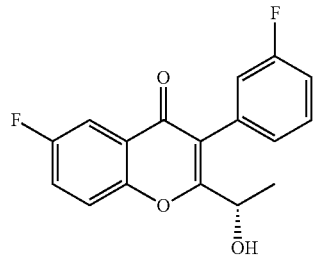 [SMILES: C[C@H](O)c1oc2ccc(F)cc2c(=O)c1-c1cccc(F)c1]

To intermediate 3 (2.00 g, 6.66 mmol), R-Alpine borane (0.5 M in THF, 20 ml) was added and heated to 60° C. for 20 hours. The reaction mixture quenched with 2N HCl, and extracted with ethyl acetate. The organic layer was dried over sodium sulphate and concentrated under reduced pressure. The crude product was purified by column chromatography with ethyl acetate:petroleum ether to afford the title compound as an off-white solid (1.51 g, 75%). Enantiomeric excess: 94.2%, enriched in the fast eluting isomer (retention time: 8.78 min.) as determined by HPLC on a chiralpak AD-H column.

Intermediate 5: (R)-1-(6-fluoro-3-(3-fluorophenyl)-4-oxo-4H-chromen-2-yl)ethyl 4-chlorobenzoate

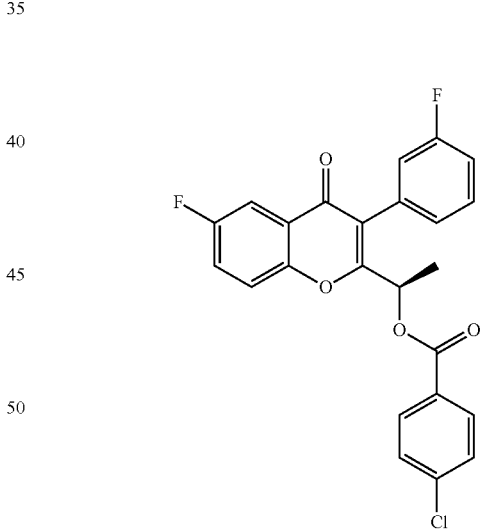

To a solution of intermediate 4 (1.45 g, 4.78 mmol) in THF (15 ml), 4-chlorobenzoic acid (0.748 g, 4.78 mmol) and triphenylphosphine (1.88 g, 7.17 mmol) were added and heated to 45° C. followed by diisopropylazodicarboxylate (1.4 ml, 7.17 mmol). After 1 hour, the reaction mixture was concentrated and the residue was purified by column chromatography with ethyl acetate:petroleum ether to afford the title compound as an off-white solid (1.81 g, 86%) which was used without purification in the next step.

Intermediate 6: (R)-6-fluoro-3-(3-fluorophenyl)-2-(1-hydroxyethyl)-4H-chromen-4-one

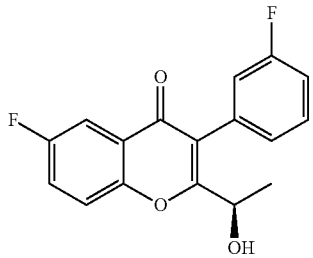 [SMILES: C[C@@H](O)c1oc2ccc(F)cc2c(=O)c1-c1cccc(F)c1]

Method A

Intermediate 5 (1.75 g, 3.96 mmol) in methanol (17 ml) was cooled to 10° C., potassium carbonate (0.273 g, 1.98 mmol) was added and stirred for 30 min. The reaction mixture was concentrated, acidified with 2N HCl solution, extracted with ethyl acetate, dried over sodium sulphate and concentrated under reduced pressure. The crude product was purified by column chromatography with ethyl acetate: petroleum ether to afford the title compound as a yellow solid (1.05 g, 87% yield). Enantiomeric excess: 93.6%, enriched in the late eluting isomer (retention time: 11.12 min.) as determined by HPLC on a chiralpak AD-H column.

Method B

Step-1

[(R)-2-(1-(benzyloxy)ethyl)-6-fluoro-3-(3-fluorophenyl)-4H-chromen-4-one]: To 1-(5-fluoro-2-hydroxyphenyl)-2-(3-fluorophenyl)ethanone (11.00 g, 44.31 mmol) in dichloromethane, HATU (33.7 g, 88.63 mmol) and R-(+)2-benzyloxypropionic acid (9.58 g, 53.17 mmol) were added and stirred for 10 min. Triethylamine (66.7 ml, 0.47 mol) was added dropwise and stirred at RT for 24 hours. The reaction mixture was quenched with water, extracted with dichloromethane, dried over sodium sulphate and concentrated under reduced pressure. The crude product was purified by column chromatography with ethyl acetate:petroleum ether to afford the title compound as a yellow solid (10.5 g, 60% yield). $^1$H-NMR (δ ppm, CDCl$_3$, 400 MHz): 7.85 (dd, J=8.1, 3 Hz, 1H), 7.58 (dd, J=9.1, 4.1 Hz, 1H), 7.47-7.39 (m, 1H), 7.39-7.34 (m, 1H), 7.28-7.20 (m, 3H), 7.20-7.14 (m, 2H), 7.16-7.07 (m, 1H), 6.99-6.89 (m, 2H), 4.50-4.31 (m, 3H), 1.56 (d, J=6.4 Hz, 3H).

Step-2:

(R)-2-(1-(benzyloxy)ethyl)-6-fluoro-3-(3-fluorophenyl)-4H-chromen-4-one obtained in Step-1 (10.5 g, 26.69 mmol) in dichloromethane (110 ml) was cooled to 0° C., aluminium chloride (5.35 g, 40.03 mmol) was added portionwise and stirred at RT for 6 hours. The reaction mixture was quenched with 2N HCl solution, extracted with dichloromethane, dried over sodium sulphate and concentrated under reduced pressure. The crude product was purified by column chromatography with ethyl acetate:petroleum ether to afford intermediate 6 a yellow solid (6.1 g, 76% yield). Enantiomeric excess: 97.7%, enriched in the late eluting isomer (retention time: 11.12 min.) as determined by HPLC on a chiralpak AD-H column.

Intermediate 7: 4-bromo-2-fluoro-1-isopropoxybenzene

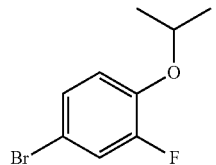

To a solution of 4-bromo-3-fluorophenol (10 g, 52.35 mmol) in THF (100 ml), isopropyl alcohol (4.8 ml, 62.62 mmol) and triphenylphosphine (20.6 g, 78.52 mmol) were added and heated to 45° C. followed by diisopropylazodicarboxylate (15.4 ml, 78.52 mmol). The mixture was refluxed for 1 hour, concentrated and the residue was purified by column chromatography with ethyl acetate:petroleum ether to afford the title compound as a colorless liquid (13.1 g, 99% yield), which was used without purification in the next step.

Intermediate 8: 2-(3-fluoro-4-isopropoxyphenyl)-4,4,5,5-tetramethyl-1,3,2-dioxaborolane

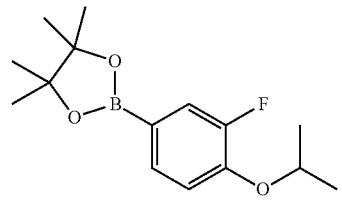 [SMILES: CC(C)Oc1ccc(B2OC(C)(C)C(C)(C)O2)cc1F]

Potassium acetate (10.52 g, 107.2 mmol) and bis(pinacolato)diboron (15 g, 58.96 mmol) were added to a solution of intermediate 7 (10.52 g, 107.2 mmol) in dioxane (125 ml), and the solution was degassed for 30 min. [1,1'-Bis(diphenylphosphino)ferrocene]dichloro palladium(II) CH$_2$Cl$_2$ (4.4 g, 5.36 mmol) was added under nitrogen atmosphere and heated to 80° C. After 12 hours, the reaction mixture was filtered through celite and concentrated. The crude product was purified by column chromatography with ethyl acetate: petroleum ether to afford the title compound as a yellow oil (13.9 g, 99%) which was used without purification in the next step.

Intermediate 9: 3-(3-fluoro-4-isopropoxyphenyl)-1H-pyrazolo[3,4-d]pyrimidin-4-amine

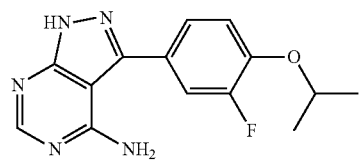 [SMILES: CC(C)Oc1ccc(-c2n[nH]c3ncnc(N)c23)cc1F]

To a solution of 3-iodo-1H-pyrazolo[3,4-d]pyrimidin-4-amine (11.0 g, 42.14 mmol) in DMF (110 ml), ethanol (55 ml) and water (55 ml), intermediate 8 (23.4 g, 84.28 mmol) and sodium carbonate (13.3 g, 126.42 mmol) were added and degassed for 30 min. Tetrakis(triphenylphosphine)palladium(0) (2.4 g, 2.10 mmol) was added under nitrogen atmosphere and heated to 80° C. After 12 hours, the reaction mixture was filtered through celite, concentrated and extracted with ethyl acetate. The organic layer was dried over sodium sulphate and concentrated under reduced pressure. The crude product was triturated with diethyl ether, filtered and dried under vacuum to afford the title compound as light brown solid (3.2 g, 26% yield) which is used as such for the next step.

(RS)-2-(1-(4-amino-3-(3-fluoro-4-isopropoxyphenyl)-1H-pyrazolo[3,4-d]pyrimidin-1-yl)ethyl)-6-fluoro-3-(3-fluorophenyl)-4H-chromen-4-one To a solution of intermediate 9 (0.080 g, 0.293 mmol) in DMF (2 ml), potassium carbonate (0.081 g, 0.587 mmol) was added and stirred at RT for 10 min. To this mixture intermediate 1 (0.215 g, 0.587 mmol) was added and stirred for 12 hours. The reaction mixture was diluted with water and extracted with ethyl acetate. The organic layer was dried over sodium sulphate and concentrated under reduced pressure. The crude product was purified by column chromatography with methanol:dichloromethane to afford the title compound as a pale yellow solid (0.045 g). MP: 175-177° C. $^1$H-NMR (δ ppm, DMSO-D$_6$, 400 MHz): δ 8.20 (s, 1H), 7.85 (dd, J=81, 3.0 Hz, 1H), 7.48-7.33 (m, 5H), 7.14 (t, J=8.3 Hz, 1H), 7.02 (m, 2H), 6.90 (m, 1H), 6.10 (q, J=7.1 Hz, 1H), 5.42 (s, 2H), 4.64 (quintet, J=6.0 Hz, 1H), 1.99 (d, J=7.1 Hz, 3H), 1.42 (d, J=6.1 Hz, 6H).

(S)-2-(1-(4-amino-3-(3-fluoro-4-isopropoxyphenyl)-1H-pyrazolo[3,4-d]pyrimidin-1-yl)ethyl)-6-fluoro-3-(3-fluorophenyl)-4H-chromen-4-one ("S-isomer")

To a solution of intermediate 9 (0.134 g, 0.494 mmol) in THF (2.0 ml), intermediate 6 (0.150 g, 0.494 mmol) and triphenylphosphine (0.194 g, 0.741 mml) were added and stirred at RT for 5 min. Diisopropylazodicarboxylate (0.15 ml, 0.749 mmol) was added heated to 45° C. After 2 hours, the reaction mixture was quenched with water and extracted with ethyl acetate. The organic layer was dried over sodium sulphate and concentrated under reduced pressure. The crude product was purified by column chromatography with ethyl acetate:petroleum ether to afford the title compound as an off-white solid (0.049 g, 20% yield). MP: 139-142° C. Mass: 571.7 (M$^+$). Enantiomeric excess: 89.8% as determined by HPLC on a chiralpak AD-H column, enriched in the fast eluting isomer (retention time=10.64 min.).

(R)-2-(1-(4-amino-3-(3-fluoro-4-isopropoxyphenyl)-1H-pyrazolo[3,4-d]pyrimidin-1-yl)ethyl)-6-fluoro-3-(3-fluorophenyl)-4H-chromen-4-one To a solution of intermediate 8 (0.284 g, 0.989 mmol) in THF (5.0 ml), intermediate 4 (0.250 g, 0.824 mmol) and tris(4-methoxy)phenylphosphine (0.435 g, 1.23 mml) were added and stirred at RT for 5 min. Diisopropylazodicarboxylate (0.25 ml, 1.23 mmol) was added stirred at RT. After 12 hours, the reaction mixture was quenched with water and extracted with ethyl acetate. The organic layer was dried over sodium sulphate and concentrated under reduced pressure. The crude product was purified by column chromatography with ethyl acetate:petroleum ether to afford the title compound as an off-white solid (0.105 g, 22% yield). MP: 145-148° C. Mass: 571.7 (M$^+$). Enantiomeric excess: 95.4% as determined by HPLC on a chiralpak AD-H column, enriched in the late eluting isomer (retention time=14.83 min.).

Biological Evaluation

Combination of a Compound of Formula A and Anti-CD20 Antibody

Example 1

S-Isomer of a Compound of Formula A and Ublituximab Combinations Deplete B Cells from Whole Blood A flow cytometry assay was used to compare the ability of S-isomer of compound of formula A, Ublituximab (Ubx), and combinations thereof to deplete B cells from human whole blood (HWB). In this assay, 50 µl of HWB sample was treated with either S-isomer of a compound of formula A (1000 nM), UBX (100 µg/ml to 0.1 µg/ml), or UBX in combination with S-isomer of a compound of formula A at 1000 nM and incubated for 24 hrs at 37° C. and 5% CO$_2$. 20 µl of treated sample was taken in a 1.5 ml centrifuge tube and labeled with CD45 FITC and CD19 PE or CD20 FITC antibody and incubated in the dark for 1 hour at RT. 1 ml of red blood cell (RBC) lysing solution was added, and tubes were centrifuged at 3000 rpm for 10 minutes. The supernatant was aspirated, and 250 µl of PBS was added to the pellet. The tubes were vortexed, and 5000 events were acquired on a Guava® easyCyte™ flow cytometer and analyzed with Incyte Software.

Gated population of CD45-positive cells were further analyzed for CD19. The number of cells that were positive for CD45 and CD19 was calculated, and the data was expressed as the percentage of CD19 positive cells in the population. CD20-positive populations were gated with fluorescence positive minus unlabeled cells, and the data was expressed as the percentage of CD20-positive cells in the population. The loss of CD19/CD20 population from control was calculated and expressed as % depletion with respect to control.

The results are shown in FIG. 1. S-isomer of a compound of formula A is not cytotoxic to B-cells at concentrations up to 10 µM. Therefore, a reduction in CD19-positive or CD20-positive HWB B-cells was not observed with 1 µM S-isomer of a compound of formula A. The UBX anti-CD20 antibody resulted in only 20-30% depletion of B-cells at doses from 1 to 100,000 ng/ml, but it caused a dose-dependent reduction in CD20+ B-cells. Combination of 1000 nM S-isomer of a compound of formula A with 10 ng/ml UBX resulted in the potentiation of CD19+ cell depletion, and combination of 1000 nM S-isomer of a compound of formula A with 0.1-10 ng/ml concentrations UBX resulted in a modest additive effect on CD20+ cell depletion. These results demonstrate that the combination of S-isomer of a compound of formula A (1000 nM) with UBX (10 ng/ml) displayed potentiation of CD19-positive cell depletion and a modest effect on CD20-positive cell depletion.

Example 2

S-Isomer of a Compound of Formula A and UBX Combinations Effect LPS-Induced B Cell Proliferation Flow cytometry was used to study the effect of S-isomer of a compound of formula A, Ubx, and combinations thereof on LPS-induced proliferation of CD19 and CD20 cells in HWB. In these experiments, 250 µl of diluted (1:3.5 with RPMI-HG Media) HWB sample was treated with either S-isomer of a compound of formula A (10 µM to 0.1 µM), UBX (100 µg/ml to 0.1 µg/ml) or UBX with S-isomer of a compound of formula A at 1000 nM for 15 minutes followed by 20 µg/ml LPS induction and incubated for 72 hrs at 37° C. and 5% $CO_2$. 20 µl of treated sample was taken in a 1.5 ml centrifuge tube and labeled with CD20 FITC and CD19 PE antibody and incubated in the dark for 1 hour at RT. 1 ml of RBC lysing solution was added and tubes were centrifuged at 3000 rpm for 10 minutes. Supernatant was aspirated, and 250 µl of PBS was added to the pellet. Tubes were vortexed, and 5000 events were acquired on a Guava® easyCyte™ flow cytometer and analyzed with Incyte Software.

Gated population of lymphocytes positive cells were further analyzed for CD19 and CD20. Cells positive for CD19 and/or CD20 were calculated, and data were expressed as the percentage positive cells in the population. The loss of positive population from control with LPS induction was calculated and expressed as % inhibition with respect to control.

The results are shown in FIGS. 2 and 3. S-isomer of a compound of formula A (1 µM) caused a dose-dependent inhibition of LPS induced CD19+ B-cell proliferation using HWB (~60%). Addition of 1 µM S-isomer of a compound of formula A to different concentrations of UBX did not increase the response beyond ~60% as a result of the minimal effect of UBX on CD19+ cells. However, an additive effect of the combination on CD19+ cell proliferation was noticed at the 100 ng/ml concentration of UBX.

In contrast to its effect on CD19+ cell proliferation, S-isomer of a compound of formula A displayed ~40% inhibition of CD20+ cells at 1 µM. An additive effect of the combination of 1 µM S-isomer of a compound of formula A with UBX was evident, especially for the 0.1 ng/ml dose.

Example 3

S-Isomer of a Compound Formula A and UBX Combinations Increase Apoptosis in Cancer Cells In order to determine the effect of S-isomer of a compound of formula A, UBX, and combinations thereof on apoptosis in cancer cells, an in situ caspase-3 kit (Millipore) was used. Cells were plated in a 6 well plate at a concentration of $0.5 \times 10^6$ cells/ml, treated with either S-isomer of a compound of formula A (1000 nM), UBX (100 µg/ml to 0.1 µg/ml), or UBX with S-isomer of a compound of formula A at 1000 nM, and incubated for 24 hrs at 37° C. and 5% $CO_2$. The cells were then transferred to microfuge tubes to receive 10 µl of freshly prepared FLICA™ reagent and incubated for 1 hour at 37° C. and 5% $CO_2$ away from light. After extensive washes with wash buffer, test samples were adjusted to equalize the number of cells in PBS. 100 µl of each cell suspension was transferred to black 96-well plates in duplicates, and the fluorescence was read at an excitation wavelength of 490 nm and an emission wavelength of 520 nm in a plate reader. The fluorescence intensity for a DMSO control was subtracted from that of test compounds. Data was expressed as a percent of the maximum response (100%) and plotted accordingly.

The results are shown in FIG. 4. UBX displayed a limited ability to induce Caspase-3 activity in the cell lines tested. Caspase-3 activity was increase by 40-75% by incubating cell lines with 1 µM S-isomer of a compound of formula A.

A synergistic effect of the combination was noticed at 100 ng/ml UBX concentration in Daudi cells while an additive effect was seen in RPMI-8226, Raji, and U226B1 cell lines at higher concentrations (10 & 100 ng/ml) of UBX.

Example 4

S-Isomer of a Compound of Formula A and UBX Combination Causes Cell Cycle Arrest A cell cycle assay reagent (Millipore) was used to determine the effect of S-isomer of a compound of formula A, UBX, and combinations thereof on the cell cycle in cancerous cells. In these experiments, cells were plated in a 6-well plate at a concentration of $0.5 \times 10^6$ cells/ml, treated with either S-isomer of a compound of formula A (10 µM to 0.1 µM), UBX (100 µg/ml to 0.1 µg/ml), or UBX with S-isomer of a compound of formula A at 1000 nM, and incubated for 72 hrs at 37° C. and 5% $CO_2$. The cells were transferred to microfuge tubes to receive 50 µl of cell cycle reagent and incubated for 30 minutes at RT away from light. Cells were then diluted with 300-400 µl PBS, and a minimum of 10,000 events were acquired on a Guava® easyCyte™ flow cytometer. The data was analyzed with Express Pro software and the percentage of the cell population in different cell cycle stages with respect to control was presented in histograms.

FIGS. 5-10 show the results obtained with U266B1, and Raji cells. In addition, Tables 1-12 below provide the quantitative results obtained using U266B1, DB, Raji, and Daudi cells.

TABLE 1

U266B1 Cells - 72 h Incubation with a Compound of Formula A

| Treatment | G0/G1 | S | G2/M | Sub G0 |
|---|---|---|---|---|
| Control | 60.22 | 4.29 | 31.72 | 3.01 |
| 10,000 nM | 2.00 | 0.94 | 64.31 | 28.88 |
| 1000 nM | 47.80 | 4.69 | 47.13 | 0.88 |
| 100 nM | 48.69 | 5.49 | 45.76 | 0.75 |
| 10 nM | 55.33 | 5.38 | 39.28 | 0.76 |
| 1 nM | 57.73 | 4.87 | 36.19 | 0.94 |
| 0.1 nM | 59.26 | 6.55 | 30.71 | 2.75 |

TABLE 2

U266B1 Cells - 72 h Incubation with UBX Anti-CD20 Antibody

| Treatment | G0/G1 | S | G2/M | Sub G0 |
|---|---|---|---|---|
| Control | 60.22 | 4.29 | 31.72 | 3.01 |
| 100 ng/ml | 52.95 | 7.91 | 39.65 | 1.95 |
| 10 ng/ml | 56.85 | 6.34 | 37.86 | 0.78 |
| 1 ng/ml | 58.81 | 7.07 | 36.07 | 0.51 |
| 0.1 ng/ml | 57.53 | 7.63 | 35.64 | 1.35 |
| 0.01 ng/ml | 59.32 | 6.57 | 35.48 | 0.74 |
| 0.001 ng/ml | 60.79 | 6.00 | 30.49 | 1.34 |

TABLE 3

U266B1 Cells - 72 h Incubation with UBX + a Compound of Formula A (1000 nM)

| Treatment | G0/G1 | S | G2/M | Sub G0 |
|---|---|---|---|---|
| Control | 60.22 | 4.29 | 31.72 | 3.01 |
| 100 ng/ml + Comp. A | 1.25 | 0.68 | 84.46 | 12.76 |
| 10 ng/ml + Comp. A | 1.68 | 1.20 | 84.97 | 11.70 |
| 1 ng/ml + Comp. A | 47.97 | 3.81 | 46.37 | 0.63 |

TABLE 3-continued

U266B1 Cells - 72 h Incubation with UBX +
a Compound of Formula A (1000 nM)

| Treatment | G0/G1 | S | G2/M | Sub G0 |
|---|---|---|---|---|
| 0.1 ng/ml + Comp. A | 47.31 | 4.28 | 46.47 | 0.50 |
| 0.01 ng/ml + Comp. A | 47.48 | 3.84 | 46.51 | 0.56 |
| 0.001 ng/ml + Comp. A | 47.09 | 3.97 | 47.05 | 0.59 |

TABLE 4

DB Cells - 72 h Incubation with a Compound of Formula A

| Treatment | G0/G1 | S | G2/M | Sub G0 |
|---|---|---|---|---|
| Control | 54.30 | 8.00 | 36.38 | 0.48 |
| 10,000 nM | 1.40 | 0.89 | 94.87 | 2.06 |
| 1000 nM | 0.75 | 0.42 | 92.79 | 5.36 |
| 100 nM | 41.21 | 6.96 | 50.22 | 0.43 |
| 10 nM | 47.22 | 4.98 | 46.85 | 0.55 |
| 1 nM | 50.61 | 6.53 | 41.44 | 0.54 |
| 0.1 nM | 54.37 | 4.84 | 39.41 | 0.84 |

TABLE 5

DB Cells - 72 h Incubation with UBX Anti-CD20 Antibody

| Treatment | G0/G1 | S | G2/M | Sub G0 |
|---|---|---|---|---|
| Control | 54.30 | 8.00 | 36.38 | 0.48 |
| 100 ng/ml | 45.98 | 7.66 | 46.55 | 0.67 |
| 10 ng/ml | 49.52 | 10.07 | 40.56 | 0.56 |
| 1 ng/ml | 51.36 | 6.46 | 40.07 | 0.52 |
| 0.1 ng/ml | 56.34 | 12.34 | 38.40 | 1.10 |
| 0.01 ng/ml | 54.99 | 7.73 | 34.79 | 0.73 |
| 0.001 ng/ml | 54.38 | 9.45 | 34.02 | 0.59 |

TABLE 6

DB Cells - 72 h Incubation with
UBX + a Compound of Formula A

| Treatment | G0/G1 | S | G2/M | Sub G0 |
|---|---|---|---|---|
| Control | 54.30 | 8.00 | 36.38 | 0.48 |
| 100 ng/ml + Comp. A | 0.48 | 0.32 | 93.78 | 5.91 |
| 10 ng/ml + Comp. A | 0.70 | 0.99 | 93.34 | 4.79 |
| 1 ng/ml + Comp. A | 0.31 | 0.74 | 92.65 | 6.00 |
| 0.1 ng/ml + Comp. A | 0.44 | 0.63 | 92.84 | 5.83 |
| 0.01 ng/ml + Comp. A | 0.09 | 0.84 | 93.97 | 4.30 |
| 0.001 ng/ml + Comp. A | 0.06 | 0.17 | 94.48 | 5.31 |

TABLE 7

Raji Cells - 72 h Incubation with a Compound of Formula A

| Treatment | G0/G1 | S | G2/M | Sub G0 |
|---|---|---|---|---|
| Control | 54.10 | 9.08 | 33.54 | 2.14 |
| 10,000 nM | 10.12 | 23.17 | 58.09 | 4.90 |
| 1000 nM | 52.04 | 3.92 | 41.21 | 1.29 |
| 100 nM | 52.81 | 6.72 | 37.80 | 1.04 |
| 10 nM | 55.96 | 5.80 | 34.81 | 1.06 |
| 1 nM | 56.93 | 5.51 | 34.13 | 1.89 |
| 0.1 nM | 56.54 | 8.38 | 33.63 | 1.32 |

TABLE 8

Raji Cells - 72 h Incubation with UBX Anti-CD20 Antibody

| Treatment | G0/G1 | S | G2/M | Sub G0 |
|---|---|---|---|---|
| Control | 54.10 | 9.08 | 33.54 | 2.14 |
| 100 ng/ml | 22.19 | 11.05 | 33.74 | 34.78 |
| 10 ng/ml | 45.01 | 8.15 | 12.90 | 31.86 |
| 1 ng/ml | 39.72 | 14.82 | 15.35 | 27.32 |
| 0.1 ng/ml | 41.11 | 8.93 | 22.00 | 23.73 |
| 0.01 ng/ml | 54.54 | 12.65 | 25.08 | 5.51 |
| 0.001 ng/ml | 50.52 | 10.61 | 33.66 | 4.35 |

TABLE 9

Raji Cells - 72 h Incubation with UBX +
a Compound of Formula A (1000 nM)

| Treatment | G0/G1 | S | G2/M | Sub G0 |
|---|---|---|---|---|
| Control | 54.10 | 9.08 | 33.54 | 2.14 |
| 100 ng/ml + Comp. A | 44.19 | 3.20 | 0.21 | 51.17 |
| 10 ng/ml + Comp. A | 46.93 | 5.98 | 3.20 | 42.80 |
| 1 ng/ml + Comp. A | 46.35 | 6.75 | 5.98 | 40.10 |
| 0.1 ng/ml + Comp. A | 44.85 | 9.72 | 13.00 | 30.88 |
| 0.01 ng/ml + Comp. A | 50.11 | 12.22 | 24.04 | 13.51 |
| 0.001 ng/ml + Comp. A | 49.23 | 5.16 | 38.21 | 4.73 |

TABLE 10

Daudi Cells - 72 h Incubation with a Compound of Formula A

| Treatment | G0/G1 | S | G2/M | Sub G0 |
|---|---|---|---|---|
| Control | 50.91 | 11.10 | 28.51 | 10.81 |
| 10,000 nM | 2.53 | 21.92 | 65.03 | 5.01 |
| 1000 nM | 48.27 | 7.91 | 40.10 | 2.22 |
| 100 nM | 47.39 | 11.33 | 38.05 | 1.30 |
| 10 nM | 46.84 | 12.55 | 37.79 | 1.68 |
| 1 nM | 48.11 | 13.27 | 36.75 | 0.74 |
| 0.1 nM | 49.56 | 14.13 | 33.23 | 0.34 |

TABLE 11

Daudi Cells - 72 h Incubation with UBX Anti-CD20 Antibody

| Treatment | G0/G1 | S | G2/M | Sub G0 |
|---|---|---|---|---|
| Control | 50.91 | 11.10 | 28.51 | 10.81 |
| 100 ng/ml | 43.66 | 9.28 | 28.55 | 19.55 |
| 10 ng/ml | 40.92 | 13.23 | 28.08 | 17.77 |
| 1 ng/ml | 40.52 | 17.54 | 26.99 | 14.95 |
| 0.1 ng/ml | 37.40 | 17.06 | 32.42 | 13.42 |
| 0.01 ng/ml | 36.24 | 19.15 | 37.83 | 6.77 |
| 0.001 ng/ml | 38.12 | 17.90 | 41.95 | 2.03 |

TABLE 12

Daudi Cells - 72 h Incubation with UBX +
a Compound of Formula A (1000 nM)

| Treatment | G0/G1 | S | G2/M | Sub G0 |
|---|---|---|---|---|
| Control | 50.91 | 11.10 | 28.51 | 10.81 |
| 100 ng/ml + Comp. A | 38.37 | 8.43 | 12.95 | 40.24 |
| 10 ng/ml + Comp. A | 49.56 | 8.47 | 9.80 | 32.17 |
| 1 ng/ml + Comp. A | 51.73 | 8.75 | 11.81 | 26.26 |
| 0.1 ng/ml + Comp. A | 56.23 | 7.25 | 11.60 | 24.80 |
| 0.01 ng/ml + Comp. A | 55.87 | 6.17 | 17.00 | 22.02 |
| 0.001 ng/ml + Comp. A | 36.58 | 17.03 | 35.74 | 10.64 |

These results demonstrate that of cells contacted with S-isomer of a compound of formula A, resulted in a dose-dependent G2/M arrest. In addition, treatment with UBX for 72 hours caused a modest G2/M arrest in Diffuse Large B-cell Lymphoma (DB) and U266B1 cells, while it increased the number of Sub G0 cells in Raji and Daudi cells. Combination with 1 μM S-isomer of a compound of formula A accentuated the UBX response across the cell-lines tested.

Example 5

S-Isomer of a Compound Formula A and UBX Combinations Synergistically Increase Apoptosis in Cancer Cells In order to determine the effect of S-isomer of a compound of formula A, UBX, and combinations thereof on apoptosis in cancer cells, an in situ caspase-3 kit (Millipore) was used. Cells were plated in a 6 well plate at a concentration of 0.5×10$^6$ cells/ml, treated with either S-isomer of a compound of formula A (200-5000 nM), UBX (10,000 ng/ml to 10 ng/ml), or UBX with S-isomer of a compound of formula A (as indicated), and incubated for 24 hrs at 37° C. and 5% $CO_2$. The cells were then transferred to microfuge tubes to receive 10 μl of freshly prepared FLICA™ reagent and incubated for 1 hour at 37° C. and 5% $CO_2$ away from light. After extensive washes with wash buffer, test samples were adjusted to equalize the number of cells in PBS. 100 μl of each cell suspension was transferred to black 96-well plates in duplicates, and the fluorescence was read at an excitation wavelength of 490 nm and an emission wavelength of 520 nm in a plate reader. The fluorescence intensity for a DMSO control was subtracted from that of test compounds. Data was expressed as caspase-3 activity a combination index (C.I.) calculated. C.I.'s less than one indicate synergism, of one indicate additive effects and greater than one indicate antagonism.

The results are shown in FIG. 11 and Tables 13-15 for DBCL cell line LY1. UBX induced caspase-3 activity in LY1. Caspase-3 activity was synergistically increased in the presence of UBX (all concentrations) and S-isomer of a compound of formula A (1000 nM).

The results are shown in FIG. 12 and Tables 16-18 for the Burkitt lymphoma cell line Raji. UBX induced caspase-3 activity in Raji LY1. Caspase-3 activity was synergistically increased in the presence of UBX (all concentrations) and S-isomer of a compound of formula A (200 nM).

TABLE 13

LY1 Cells Incubated with S-isomer
S-isomer

| Concentration (nM) | Caspase 3 Activity |
| --- | --- |
| 200 | 0.06 |
| 1000 | 0.17 |
| 5000 | 0.61 |

TABLE 14

LY1 Cells Incubated with UBX
UBX

| Concentration (ng/ml) | Caspase 3 Activity |
| --- | --- |
| 10 | 0.23 |
| 100 | 0.32 |

TABLE 14-continued

LY1 Cells Incubated with UBX
UBX

| Concentration (ng/ml) | Caspase 3 Activity |
| --- | --- |
| 1000 | 0.53 |
| 10,000 | 0.59 |

TABLE 15

LY1 Cells Incubated with S-isomer and UBX
COMBINATION

| S-isomer (nM) | UBX (ng/ml) | Caspase 3 Activity | C.I. |
| --- | --- | --- | --- |
| 200 | 10 | 0.2715 | 0.6 |
| 200 | 100 | 0.3404 | 1.2 |
| 200 | 1000 | 0.5902 | 0.2 |
| 200 | 10000 | 0.6317 | 0.8 |
| 1000 | 10 | 0.3811 | 0.5 |
| 1000 | 100 | 0.5523 | 0.2 |
| 1000 | 1000 | 0.743 | 0.1 |
| 1000 | 10000 | 0.8181 | 0.1 |
| 5000 | 10 | 0.7359 | 0.5 |
| 5000 | 100 | 0.8339 | 0.3 |
| 5000 | 1000 | 0.999 | 0.0 |
| 5000 | 10000 | 0.999 | 0.0 |

TABLE 16

Raji Cells Incubated with S-isomer
S-isomer

| Concentration (nM) | Caspase 3 Activity |
| --- | --- |
| 200 | 0.36 |
| 1000 | 0.56 |
| 5000 | 0.80 |

TABLE 17

Raji Cells Incubated with UBX
UBX

| Concentration (ng/ml) | Caspase 3 Activity |
| --- | --- |
| 10 | 0.18 |
| 100 | 0.31 |
| 1000 | 0.51 |
| 10,000 | 0.60 |

TABLE 18

Raji Cells Incubated with S-isomer and UBX
COMBINATION

| S-isomer (nM) | UBX (ng/ml) | Caspase 3 Activity | C.I. |
| --- | --- | --- | --- |
| 200 | 10 | 0.696 | 0.20 |
| 200 | 100 | 0.895 | 0.04 |
| 200 | 1000 | 0.999 | 0.00 |
| 200 | 10000 | 0.993 | 0.00 |
| 1000 | 10 | 0.805 | 0.49 |
| 1000 | 100 | 0.939 | 0.11 |
| 1000 | 1000 | 0.928 | 0.13 |
| 1000 | 10000 | 0.866 | 0.30 |
| 5000 | 10 | 0.901 | 0.97 |
| 5000 | 100 | 0.829 | 2.03 |
| 5000 | 1000 | 0.861 | 1.52 |
| 5000 | 10000 | 0.844 | 1.80 |

Tree additional cell lines, LY10 (DLBCL), Toledo (DLBCL) and Daudi (Burkitt lymphoma) were assessed for the effects of combinations of S-isomer of a compound of formula A and UBX on caspase 3 activity as described above. The results are shown in Tables 19-21. The combinations also demonstrated synergistic activation of caspase 3.

TABLE 19

LY10 Cells Incubated with S-isomer and UBX (DLBCL)

| S-isomer (nM) | UBX (ng/mL) | Caspase 3 Activity | C.I. |
|---|---|---|---|
| 5000 | 50 | 0.999 | 0.021 |
| 1000 | 10 | 0.421 | 0.560 |
| 200 | 2 | 0.119 | 0.440 |

TABLE 20

Toledo Cells Incubated with S-isomer and UBX (DLBCL)

| S-isomer (nM) | UBX (ng/mL) | Caspase 3 Activity | C.I. |
|---|---|---|---|
| 5000 | 50 | 0.988 | 0.336 |
| 1000 | 10 | 0.685 | 0.548 |
| 200 | 2 | 0.136 | 0.576 |

TABLE 21

Daudi Cells Incubated with S-isomer and UBX (Burkitt lymphoma)

| S-isomer (nM) | UBX (ng/mL) | Caspase 3 Activity | C.I. |
|---|---|---|---|
| 5000 | 50 | 0.999 | 0.004 |
| 1000 | 10 | 0.594 | 0.582 |
| 200 | 2 | 0.296 | 0.393 |

Three Mantle cell lymphoma (MCL) cell lines, Jeko, Mayer and Rec-1, were assessed for the effects of combinations of S-isomer of a compound of formula A and UBX on caspase 3 activity as described above. The results are shown in Tables 22-24. The combinations also demonstrated synergistic activation of caspase 3, with synergy optimized at higher S-isomer and UBX concentrations.

TABLE 22

Jeko Cells Incubated with S-isomer and UBX

| S-isomer (nM) | UBX (ng/mL) | Caspase 3 Activity | C.I. |
|---|---|---|---|
| 5000 | 50 | 0.999 | 0.000 |
| 1000 | 10 | 0.655 | 0.274 |
| 200 | 2 | 0.335 | 0.506 |

TABLE 23

Maver Cells Incubated with S-isomer and UBX

| S-isomer (nM) | UBX (ng/mL) | Caspase 3 Activity | C.I. |
|---|---|---|---|
| 5000 | 50 | 0.999 | 0.000 |
| 1000 | 10 | 0.437 | 0.603 |
| 200 | 2 | 0.213 | 0.648 |

TABLE 24

Rec-1 Cells Incubated with S-isomer and UBX

| S-isomer (nM) | UBX (ng/mL) | Caspase 3 Activity | C.I. |
|---|---|---|---|
| 5000 | 50 | 0.999 | 0.000 |
| 1000 | 10 | 0.484 | 0.303 |
| 200 | 2 | 0.403 | 0.132 |

Overall, these results show that the S-isomer of a compound of formula A and UBX potently synergize in the activation of caspase 3, a marker for apoptosis, in B-cell lymphoma models.

The present invention has been described above with the aid of functional building blocks illustrating the implementation of specified functions and relationships thereof. The boundaries of these functional building blocks have been arbitrarily defined herein for the convenience of the description. Alternate boundaries can be defined so long as the specified functions and relationships thereof are appropriately performed.

The foregoing description of the specific embodiments will so fully reveal the general nature of the invention that others can, by applying knowledge within the skill of the art, readily modify and/or adapt for various applications such specific embodiments, without undue experimentation, without departing from the general concept of the present invention. Therefore, such adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance. References cited herein are hereby incorporated herein by reference.

What is claimed is:

1. A method of inhibiting proliferation of a CD20-positive, hematopoietic cell population comprising contacting the population with a combination comprising (i) the compound (S)-2-(1-(4-amino-3-(3-fluoro-4-isopropoxyphenyl)-1H-pyrazolo[3,4-d]pyrimidin-1-yl)ethyl)-6-fluoro-3-(3-fluorophenyl)-4H-chromen-4-one, or a pharmaceutically acceptable salt, solvate, or prodrug thereof, and (ii) an anti-CD20 antibody or antigen-binding fragment thereof, wherein said anti-CD20 antibody or fragment (a) is ublituximab or (b) binds to the same epitope as ublituximab.

2. The method of claim 1, wherein said antibody or fragment comprises the VH CDR1, CDR2 and CDR3 region of sequences SEQ ID NO:1, 2, and 3, and the VL CDR1, CDR2 and CDR3 region of sequences SEQ ID NO:6, 7, and 8.

3. The method of claim 2, wherein the anti-CD20 antibody or antigen-binding fragment thereof comprises the VH of SEQ ID NO:4 and the VL of SEQ ID NO:9.

4. The method of claim 1, wherein said anti-CD20 antibody is ublituximab.

5. The method of claim 1, wherein said compound is (S)-2-(1-(4-amino-3-(3-fluoro-4-isopropoxyphenyl)-1H-pyrazolo[3,4-d]pyrimidin-1-yl)ethyl)-6-fluoro-3-(3-fluorophenyl)-4H-chromen-4-one and said anti-CD20 antibody is ublituximab.

6. The method of claim 1, wherein the population is contacted with (i) a first composition comprising (S)-2-(1-(4-amino-3-(3-fluoro-4-isopropoxyphenyl)-1H-pyrazolo[3,4-d]pyrimidin-1-yl)ethyl)-6-fluoro-3-(3-fluorophenyl)-4H-chromen-4-one and (ii) a second composition comprising the anti-CD20 antibody or fragment.

7. The method of claim 6, wherein the compound is (S)-2-(1-(4-amino-3-(3-fluoro-4-isopropoxyphenyl)-1H-pyrazolo[3,4-d]pyrimidin-1-yl)ethyl)-6-fluoro-3-(3-fluorophenyl)-4H-chromen-4-one and the anti-CD20 antibody is ublituximab.

8. The method of claim 1, wherein the population is in a human subject.

9. The method of claim 8, wherein the subject has a disease or disorder associated with excessive B-cell proliferation, cancer or an autoimmune disease or disorder.

10. The method of claim 9, wherein the cancer is a hematological malignancy.

11. The method of claim 10, wherein the hematological malignancy is lymphoma or leukemia.

12. The method of claim 10, wherein the hematological malignancy is selected from the group consisting of acute lymphocytic leukemia (ALL), acute myeloid leukemia (AML), chronic lymphocytic leukemia (CLL), small lymphocytic lymphoma (SLL), multiple myeloma (MM), non-Hodgkin's lymphoma (NHL), mantle cell lymphoma (MCL), follicular lymphoma, Waldenstrom's macroglobulinemia (WM), B-cell lymphoma and diffuse large B-cell lymphoma (DLBCL).

13. The method of claim 9, wherein the cancer overexpresses CD20.

14. The method claim 9, wherein the cancer is refractory to chemotherapy.

15. The method of claim 8, wherein the subject has previously been treated with chemotherapy, rituximab, or a combination thereof.

16. The method of claim 8, wherein said compound and said anti-CD20 antibody or fragment are administered to the subject sequentially or simultaneously.

17. The method of claim 16, wherein said compound and said anti-CD20 antibody or fragment are contained in the same pharmaceutical composition or in separate pharmaceutical compositions.

18. The method of claim 8, further comprising administering at least one additional therapeutic agent to the subject selected from the group consisting of a proteasome inhibitor, Bortezomib (Velcade®), Carfilzomib (PR-171), PR-047, disulfiram, lactacystin, PS-519, eponemycin, epoxomycin, aclacinomycin, CEP-1612, MG-132, CVT-63417, PS-341, vinyl sulfone tripeptide inhibitors, ritonavir, PI-083, (+/−)-7-methylomuralide, (−)-7-methylomuralide, lenalidomide, and combinations thereof.

19. The method of claim 8, further comprising administering at least two additional therapeutic agents to the subject, wherein the two additional therapeutic agents are selected from the group consisting of:
  a) CHOP (cyclophosphamide, doxorubicin, vincristine, prednisone);
  b) R-CHOP (rituximab-CHOP);
  c) hyperCV AD (hyperfractionated cyclophosphamide, vincristine, doxorubicin, dexamethasone, methotrexate, cytarabine);
  d) R-hyperCV AD (rituximab-hyperCV AD);
  e) FCM (fludarabine, cyclophosphamide, mitoxantrone);
  f) R-FCM (rituximab, fludarabine, cyclophosphamide, mitoxantrone);
  g) bortezomib and rituximab;
  h) temsirolimus and rituximab;
  i) temsirolimus and Velcade®;
  j) Iodine-131 tositumomab (Bexxar®) and CHOP;
  k) CVP (cyclophosphamide, vincristine, prednisone);
  l) R-CVP (rituximab-CVP);
  m) ICE (iphosphamide, carboplatin, etoposide);
  n) R-ICE (rituximab-ICE);
  o) FCR (fludarabine, cyclophosphamide, rituximab);
  p) FR (fludarabine, rituximab); and
  q) D.T. PACE (Dexamethasone, Thalidomide, Cisplatin, Adriamycin, Cyclophosphamide, Etoposide).

20. A kit comprising (i) the compound (S)-2-(1-(4-amino-3-(3-fluoro-4-isopropoxyphenyl)-1H-pyrazolo[3,4-d]pyrimidin-1-yl)ethyl)-6-fluoro-3-(3-fluorophenyl)-4H-chromen-4-one or a pharmaceutically acceptable salt, solvate, or prodrug thereof, and (ii) an anti-CD20 antibody or antigen-binding fragment thereof, wherein said anti-CD20 antibody or fragment (a) is ublituximab or (b) binds to the same epitope as ublituximab.

21. The kit of claim 20, wherein said compound is (S)-2-(1-(4-amino-3-(3-fluoro-4-isopropoxyphenyl)-1H-pyrazolo[3,4-d]pyrimidin-1-yl)ethyl)-6-fluoro-3-(3-fluorophenyl)-4H-chromen-4-one and said anti-CD20 antibody is ublituximab.

22. The kit of claim 20, wherein said anti-CD20 antibody or fragment and said compound are contained within the same composition or are in separate compositions.

23. The kit of any one of claim 20, further comprising one or more additional active agents.

24. A pharmaceutical composition comprising
  (i) (S)-2-(1-(4-amino-3-(3-fluoro-4-isopropoxyphenyl)-1H-pyrazolo[3,4-d]pyrimidin-1-yl)ethyl)-6-fluoro-3-(3-fluorophenyl)-4H-chromen-4-one, and
  (ii) an anti-CD20 antibody or antigen-binding fragment thereof, wherein said anti-CD20 antibody or fragment (a) is ublituximab or (b) binds to the same epitope as ublituximab.

25. The pharmaceutical composition of claim 24, wherein said anti-CD20 antibody is ublituximab.

* * * * *